(12) United States Patent
Mitton-Fry

(10) Patent No.: US 11,352,349 B2
(45) Date of Patent: Jun. 7, 2022

(54) TYPE II TOPOISOMERASE INHIBITORS AND METHODS OF MAKING AND USING THEREOF

(71) Applicant: Ohio State Innovation Foundation, Columbus, OH (US)

(72) Inventor: Mark Mitton-Fry, Granville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 201 days.

(21) Appl. No.: 16/606,044

(22) PCT Filed: Apr. 17, 2018

(86) PCT No.: PCT/US2018/028001
§ 371 (c)(1),
(2) Date: Oct. 17, 2019

(87) PCT Pub. No.: WO2018/195098
PCT Pub. Date: Oct. 25, 2018

(65) Prior Publication Data
US 2020/0131158 A1 Apr. 30, 2020

Related U.S. Application Data

(60) Provisional application No. 62/568,075, filed on Oct. 4, 2017, provisional application No. 62/486,227, filed on Apr. 17, 2017.

(51) Int. Cl.
| | | |
|---|---|---|
| *C07D 405/14* | (2006.01) | |
| *C07D 405/06* | (2006.01) | |
| *C07D 409/14* | (2006.01) | |
| *C07D 491/052* | (2006.01) | |
| *C07D 491/056* | (2006.01) | |
| *C07D 498/04* | (2006.01) | |
| *C07D 513/04* | (2006.01) | |

(52) U.S. Cl.
CPC ......... *C07D 405/14* (2013.01); *C07D 405/06* (2013.01); *C07D 409/14* (2013.01); *C07D 491/052* (2013.01); *C07D 491/056* (2013.01); *C07D 498/04* (2013.01); *C07D 513/04* (2013.01)

(58) Field of Classification Search
CPC .............. C07D 319/06; C07D 405/06; C07D 405/14; A61K 31/357
See application file for complete search history.

(56) References Cited

U.S. PATENT DOCUMENTS

| | | |
|---|---|---|
| 6,002,006 A | 12/1999 | Bonnet et al. |
| 2009/0162478 A1 | 6/2009 | Abend et al. |
| 2012/0183660 A1 | 7/2012 | Tachdjian et al. |
| 2013/0295261 A1 | 11/2013 | Tachdjian et al. |

FOREIGN PATENT DOCUMENTS

| | | |
|---|---|---|
| AU | 704176 B2 | 4/1999 |
| WO | 97/02264 A1 | 1/1997 |
| WO | 2008/128942 | 10/2008 |
| WO | WO 2018/021447 A1 * | 2/2018 |

OTHER PUBLICATIONS

Douglas, Jr., Introduction to Viral Diseases, Cecil Textbook of Medicine, 20th Edition, vol. 2, pp. 1739-1742 (1996).*
Li et al., Synthesis and anti-staphylococcal activity of novel bacterial topoisomerase inhibitors with a 5-amino-1,3-dioxane linker moiety, Biorg. & Med. Chem. Letters, 28 (2018), pp. 2477-2480.*
International Search Report and Written Opinion issued by the International Searching Authority (ISA/US) in PCT Application No. PCT/US2018/028001 dated Jul. 26, 2018. 8 pages.
Bax, Benjamin D., et al. "Type IIA topoisomerase inhibition by a new class of antibacterial agents." Nature 466.7309 (2010): 935.
Lahiri, Sushmita D., et al. "Insights into the mechanism of inhibition of novel bacterial topoisomerase inhibitors from characterization of resistant mutants of *Staphylococcus aureus*." Antimicrobial agents and chemotherapy 59.9 (2015): 5278-5287.
Singh, Sheo B., et al. "Oxabicyclooctane-linked novel bacterial topoisomerase inhibitors as broad spectrum antibacterial agents." ACS medicinal chemistry letters 5.5 (2014): 609-614.
Widdowson, Katherine, and Alan Hennessy. "Advances in structure-based drug design of novel bacterial topoisomerase inhibitors." Future medicinal chemistry 2.11 (2010): 1619-1622.
European Search Report issued by the European Patent Office in Application No. EP 18787285.8 dated Sep. 2, 2020. 7 pages.
Abdel-Magid, Ahmed F., and Steven J. Mehrman. "A review on the use of sodium triacetoxyborohydride in the reductive amination of ketones and aldehydes." Organic process research & development 10.5 (2006): 971-1031.
Alanis, Alfonso J. "Resistance to antibiotics: are we in the post-antibiotic era?" Archives of medical research 36.6 (2005): 697-705.

(Continued)

*Primary Examiner* — Deepak R Rao
(74) *Attorney, Agent, or Firm* — Meunier Carlin & Curfman LLC

(57) ABSTRACT

Disclosed are Type II Topoisomerase Inhibitors, analogs thereof, pharmaceutical compositions thereof and methods of making and using these compounds and compositions. Methods of using the disclosed compounds to treat infections, such as MRSA, MDR *P. aeruginosa*, and other pathogens are also described.

35 Claims, 2 Drawing Sheets

(56) References Cited

OTHER PUBLICATIONS

Aldred, Katie J., Robert J. Kerns, and Neil Osheroff. "Mechanism of quinolone action and resistance." Biochemistry 53.10 (2014): 1565-1574.
Alexander Fleming, Penicillin, Nobel Lecture, Dec. 11, 1945 Accessed Jul. 29, 2016 http://www.nobelprize.org/nobel_prizes/medicine/laureates/1945/fleming-lecture.html.
Bax, Benjamin D., et al. "Type IIA topoisomerase inhibition by a new class of antibacterial agents." Nature 466.7309 (2010): 935-940.
Bisacchi, G. S., et al., "Recent Advances in the Inhibition of Bacterial Type II Topoisomerases", Annual Rep. Med. Chem. 2009, 44, 379.
Black, Michael T., and Kenneth Coleman. "New inhibitors of bacterial topoisomerase GyrA/ParC subunits." Curr. Opin. Invest. Drugs 10.8 (2009): 804-810.
Black, Michael T., et al. "Mechanism of action of the antibiotic NXL101, a novel nonfluoroquinolone inhibitor of bacterial type II topoisomerases." Antimicrobial agents and chemotherapy 52.9 (2008): 3339-3349.
Blumberg, Henry M., et al. "Rapid development of ciprofloxacin resistance in methicillin-susceptible and-resistant *Staphylococcus aureus*." Journal of Infectious Diseases 163.6 (1991): 1279-1285.
Boucher, Helen W., et al. "Bad bugs, no drugs: No. ESKAPE! An update from the Infectious Diseases Society of America." Clinical infectious diseases 48.1 (2009): 1-12.
Bradbury, Barton J., and Michael J. Pucci. "Recent advances in bacterial topoisomerase inhibitors." Current opinion in pharmacology 8.5 (2008): 574-581.
CDC, Biggest Threats and Data http://www.cdc.gov/drugresistance/biggest_threats.html. Accessed Jul. 29, 2016.
Cheng, Jijun, et al. "Dual targeting of DNA gyrase and topoisomerase IV: target interactions of heteroaryl isothiazolones in *Staphylococcus aureus*." Antimicrobial agents and chemotherapy 51.7 (2007): 2445-2453.
Cinquin, Bertrand, et al. "Microspectrometric insights on the uptake of antibiotics at the single bacterial cell level." Scientific reports 5 (2015): 17968.
Clinical Trial NCT02045797 https://clinicaltrials.gov/ct2/show/NCT02045797?term=2140944&rank=6. Accessed Jul. 28, 2016.
Clinical Trial NCT02294682 https://clinicaltrials.gov/ct2/show/NCT02294682?term=2140944&rank=8. Accessed Jul. 28, 2016.
Collin, Frédéric, Shantanu Karkare, and Anthony Maxwell. "Exploiting bacterial DNA gyrase as a drug target: current state and perspectives." Applied microbiology and biotechnology 92.3 (2011): 479-497.
D'Costa, Vanessa M., et al. "Antibiotic resistance is ancient." Nature 477.7365 (2011): 457.
Dougherty, T. J., et al. "NBTI 5463 Is a Novel Bacterial Type II Topoisomerase Inhibitor with Activity against Gram-Negative Bacteria and In Vivo Efficacy" Antimicrob. Agents Chemother. 2014, 58, 4250.
Dougherty, Thomas J., et al. "NBTI 5463 is a novel bacterial type II topoisomerase inhibitor with activity against Gram-negative bacteria and in vivo efficacy." Antimicrobial agents and chemotherapy 58.5 (2014): 2657-2664.
Geng, Bolin, et al. "Exploring Left-Hand-Side substitutions in the benzoxazinone series of 4-amino-piperidine bacterial type IIa topoisomerase inhibitors." Bioorganic & medicinal chemistry letters 21.18 (2011): 5432-5435.
Gleeson, M. Paul. "Generation of a set of simple, interpretable ADMET rules of thumb." Journal of medicinal chemistry 51.4 (2008): 817-834.
Høiby, Niels, Oana Ciofu, and Thomas Bjarnsholt. "Pseudomonas aeruginosa biofilms in cystic fibrosis." Future microbiology 5.11 (2010): 1663-1674.
Hooper, David C. "Emerging mechanisms of fluoroquinolone resistance." Emerging infectious diseases 7.2 (2001): 337.

Hooper, David C. "Mechanisms of action and resistance of older and newer fluoroquinolones." Clinical Infectious Diseases 31. Supplement 2 (2000): S24-S28.
Jacoby, George A. "Mechanisms of resistance to quinolones." Clinical Infectious Diseases 41. Supplement 2 (2005): S120-S126.
Jones, Jesse A., et al. "Recent advances in the rational design and optimization of antibacterial agents." MedChemComm 7.9 (2016): 1694-1715. DOI:10.1039/C6MD00232C.
Kohanski, Michael A., Daniel J. Dwyer, and James J. Collins. "How antibiotics kill bacteria: from targets to networks." Nature Reviews Microbiology 8.6 (2010): 423-435.
Leeson, Paul D., and Brian Springthorpe. "The influence of drug-like concepts on decision-making in medicinal chemistry." Nature Reviews Drug Discovery 6.11 (2007): 881-890.
Lipinski, Christopher A., et al. "Experimental and computational approaches to estimate solubility and permeability in drug discovery and development settings." Advanced drug delivery reviews 23.1-3 (1997): 3-25.
Liu, Yi-Yun, et al. "Emergence of plasmid-mediated colistin resistance mechanism MCR-1 in animals and human beings in China: a microbiological and molecular biological study." The Lancet infectious diseases 16.2 (2016): 161-168.
Mayer, Claudine, and Yves L. Janin. "Non-quinolone inhibitors of bacterial type IIA topoisomerases: a feat of bioisosterism." Chemical reviews 114.4 (2014): 2313-2342.
Miles, Timothy J., et al. "Novel amino-piperidines as potent antibacterials targeting bacterial type IIA topoisomerases." Bioorganic & medicinal chemistry letters 21.24 (2011): 7489-7495.
Miles, Timothy J., et al. "Novel cyclohexyl-amides as potent antibacterials targeting bacterial type IIA topoisomerases." Bioorganic & medicinal chemistry letters 21.24 (2011): 7483-7488.
Miles, Timothy J., et al. "Novel hydroxyl tricyclics (eg, GSK966587) as potent inhibitors of bacterial type IIA topoisomerases." Bioorganic & medicinal chemistry letters 23.19 (2013): 5437-5441.
Mitscher, Lester A. "Bacterial topoisomerase inhibitors: quinolone and pyridone antibacterial agents." Chemical reviews 105.2 (2005): 559-592.
Mitton-Fry, M. J. Novel, Non-quinolone Inhibitors of DNA Gyrase and Topoisomerase IV: Antibacterial Activity and Resistance Mechanisms. Presented at the 243rd National Meeting of the American Chemical Society, San Diego, CA, 2012, Paper MEDI-257.
Mitton-Fry, Mark J., et al. "Novel quinoline derivatives as inhibitors of bacterial DNA gyrase and topoisomerase IV." Bioorganic & medicinal chemistry letters 23.10 (2013): 2955-2961.
Morrill, Haley J., et al. "Treatment options for carbapenem-resistant Enterobacteriaceae infections." Open forum infectious diseases. vol. 2. No. 2. 5;2(2):ofv050 2015.
Morrow, Brian J., et al. "Antistaphylococcal activities of the new fluoroquinolone JNJ-Q2." Antimicrobial agents and chemotherapy 55.12 (2011): 5512-5521.
Nayar, Asha S., et al. "Target-based resistance in Pseudomonas aeruginosa and *Escherichia coli* to NBTI 5463, a novel bacterial type II topoisomerase inhibitor." Antimicrobial agents and chemotherapy 59.1 (2015): 331-337.
Ndubaku, Chudi O., et al. "Design of selective PAK1 inhibitor G-5555: improving properties by employing an unorthodox low-p K a polar moiety." ACS medicinal chemistry letters 6.12 (2015): 1241-1246.
New York Times, Infection Raises Specter of Superbugs Resistant to All Antibiotics. Accessed Jul. 29, 2016 https://www.nytimes.com/2016/05/27/health/infection-raises-specter-of-superbugs-resistant-to-all-antibiotics.html.
O'Shea, Rosemarie, and Heinz E. Moser. "Physicochemical properties of antibacterial compounds: implications for drug discovery." Journal of medicinal chemistry 51.10 (2008): 2871-2878.
Onodera, Yoshikuni, et al. "Dual inhibitory activity of sitafloxacin (DU-6859a) against DNA gyrase and topoisomerase IV of *Streptococcus pneumoniae*." Journal of Antimicrobial Chemotherapy 44.4 (1999): 533-536.
Pasternak, Alexander, et al. "Potent, orally bioavailable somatostatin agonists: good absorption achieved by urea backbone cyclization." Bioorganic & medicinal chemistry letters 9.3 (1999): 491-496.

(56) References Cited

OTHER PUBLICATIONS

Payne, David J., et al. "Drugs for bad bugs: confronting the challenges of antibacterial discovery." Nature reviews Drug discovery 6.1 (2007): 29-40.
Payne, David J., et al. "Time for a change: addressing R&D and commercialization challenges for antibacterials." Philosophical Transactions of the Royal Society B: Biological Sciences 370.1670 (2015): 20140086.
PewTrust, A Scientific Roadmap for Antibiotic Discovery, May 2016. Accessed Jul. 29, 2016. http://www.pewtrusts.org/en/research-and-analysis/reports/2016/05/a-scientific-roadmap-for-antibioticdiscovery.
Phillips, John W., et al. "Discovery of kibdelomycin, a potent new class of bacterial type II topoisomerase inhibitor by chemical-genetic profiling in *Staphylococcus aureus*." Chemistry & biology 18.8 (2011): 955-965.
Piddock, Laura, Sylvie Garneau-Tsodikova, and Colin Garner. "Ask the experts: how to curb antibiotic resistance and plug the antibiotics gap?." Future medicinal chemistry 8.10 (2016): 1027-1032.
Reck, Folkert, et al. "Novel N-linked aminopiperidine inhibitors of bacterial topoisomerase type II: broad-spectrum antibacterial agents with reduced hERG activity." Journal of medicinal chemistry 54.22 (2011): 7834-7847.
Reck, Folkert, et al. "Novel N-linked aminopiperidine inhibitors of bacterial topoisomerase type II with reduced p K a: antibacterial agents with an improved safety profile." Journal of medicinal chemistry 55.15 (2012): 6916-6933.
Reck, Folkert, et al. "Optimization of physicochemical properties and safety profile of novel bacterial topoisomerase type II inhibitors (NBTIs) with activity against Pseudomonas aeruginosa." Bioorganic & Medicinal Chemistry 22.19 (2014): 5392-5409.
Rice, Louis B. "Federal funding for the study of antimicrobial resistance in nosocomial pathogens: no ESKAPE." (2008): 1079-1081.
Ross, James E., et al. "Determination of disk diffusion and MIC quality control guidelines for GSK2140944, a novel bacterial type II topoisomerase inhibitor antimicrobial agent." Journal of Clinical Microbiology 52.7 (2014): 2629-2632.
Ruppé, Étienne, Paul-Louis Woerther, and François Barbier. "Mechanisms of antimicrobial resistance in Gram-negative bacilli." Annals of intensive care 5.1 (2015): 21.
Schwarz, Stefan, and Alan P. Johnson. "Transferable resistance to colistin: a new but old threat." Journal of Antimicrobial Chemotherapy 71.8 (2016): 2066-2070.
Scorciapino, Mariano Andrea, et al. "Exploiting the porin pathway for polar compound delivery into Gram-negative bacteria." Future Medicinal Chemistry 8.10 (2016): 1047-1062.
Servick, Kelly. "The drug push." Science, (2015): 850-853.
Silver, Lynn L. "A Gestalt approach to Gram-negative entry." Bioorganic & medicinal chemistry 24.24 (2016): 6379-6389. http://dx.doi.org/10.1016/j.bmc.2016.06.044.
Singh, Sheo B., et al. "Structure activity relationship of pyridoxazinone substituted RHS analogs of oxabicyclooctane-linked 1, 5-naphthyridinyl novel bacterial topoisomerase inhibitors as broad-spectrum antibacterial agents (Part—6)." Bioorganic & Medicinal Chemistry Letters 25.17 (2015): 3636-3643.
Singh, Sheo B., et al. "C1-C2-linker substituted 1, 5-naphthyridine analogues of oxabicyclooctane-linked NBTIs as broad-spectrum antibacterial agents (part 7)." Medchemcomm 6.10 (2015): 1773-1780.
Singh, Sheo B. "Confronting the challenges of discovery of novel antibacterial agents." Bioorganic & medicinal chemistry letters 24.16 (2014): 3683-3689.
Singh, Sheo B., et al. "Hydroxy tricyclic 1, 5-naphthyridinone oxabicyclooctane-linked novel bacterial topoisomerase inhibitors as broad-spectrum antibacterial agents—SAR of RHS moiety (Part—3)." Bioorganic & Medicinal Chemistry Letters 25.12 (2015): 2473-2478.
Singh, Sheo B., et al. "Structure activity relationship of substituted 1, 5-naphthyridine analogs of oxabicyclooctane-linked novel bacterial topoisomerase inhibitors as broad-spectrum antibacterial agents (Part—4)." Bioorganic & Medicinal Chemistry Letters 25.11 (2015): 2409-2415.
Singh, Sheo B., et al. "Tricyclic 1, 5-naphthyridinone oxabicyclooctane-linked novel bacterial topoisomerase inhibitors as broad-spectrum antibacterial agents—SAR of left-hand-side moiety (Part—2)." Bioorganic & Medicinal Chemistry Letters 25.9 (2015): 1831-1835.
So, Wonhee, Jared L. Crandon, and David P. Nicolau. "Pharmacodynamic profile of GSK2140944 against methicillin-resistant *Staphylococcus aureus* in a murine lung infection model." Antimicrobial Agents and Chemotherapy 59.8 (2015): 4956-4961.
Spellberg, Brad, John G. Bartlett, and David N. Gilbert. "The future of antibiotics and resistance." New England Journal of Medicine 368.4 (2013): 299-302.
Surivet, Jean-Philippe, et al. "Design, synthesis, and characterization of novel tetrahydropyran-based bacterial topoisomerase inhibitors with potent anti-gram-positive activity." Journal of medicinal chemistry 56.18 (2013): 7396-7415.
Surivet, Jean-Philippe, et al. "Novel tetrahydropyran-based bacterial topoisomerase inhibitors with potent anti-gram positive activity and improved safety profile." Journal of medicinal chemistry 58.2 (2015): 927-942.
Tan, Christopher M., et al. "In vitro and in vivo characterization of the novel oxabicyclooctane-linked bacterial topoisomerase inhibitor AM-8722, a selective, potent inhibitor of bacterial DNA gyrase." Antimicrobial agents and chemotherapy 60.8 (2016): 4830-4839.
Tommasi, Ruben, et al. "ESKAPEing the labyrinth of antibacterial discovery." Nature reviews Drug discovery 14.8 (2015): 529-542.
Tse-Dinh, Yuk-Ching. "Targeting bacterial topoisomerases: how to counter mechanisms of resistance." Future Medicinal Chemistry 8.10 (2016): 1085-1100.
Van Bambeke, Françoise, et al. "Antibiotic efflux pumps in prokaryotic cells: occurrence, impact on resistance and strategies for the future of antimicrobial therapy." Journal of Antimicrobial Chemotherapy 51.5 (2003): 1055-1065.
Veber, Daniel F., et al. "Molecular properties that influence the oral bioavailability of drug candidates." Journal of medicinal chemistry 45.12 (2002): 2615-2623.
Wagner, Stefanie, et al. "Novel strategies for the treatment of Pseudomonas aeruginosa infections." Journal of medicinal chemistry 59.13 (2016): 5929-5969.
WHO, The top 10 causes of death. http://www.who.int/mediacentre/factsheets/fs310/en/. Accessed Jul. 29, 2016.
Wiles, Jason A., et al. "Selenophene-containing inhibitors of type IIA bacterial topoisomerases." Journal of medicinal chemistry 54.9 (2011): 3418-3425.
Wise, Richard, et al. "The urgent need for new antibacterial agents." Journal of antimicrobial chemotherapy 66.9 (2011): 1939-1940.
Wohlkonig, Alexandre, et al. "Structural basis of quinolone inhibition of type IIA topoisomerases and target-mediated resistance." Nature structural & molecular biology 17.9 (2010): 1152-1153.
Zgurskaya, Helen I., Cesar A. Lopez, and Sandrasegaram Gnanakaran. "Permeability barrier of Gram-negative cell envelopes and approaches to bypass it." ACS infectious diseases 1.11 (2015): 512-522.
Zhou, Ying, et al. "Thinking outside the "bug": a unique assay to measure intracellular drug penetration in gram-negative bacteria." Analytical chemistry 87.7 (2015): 3579-3584.
International Preliminary Report on Patentability issued for Application No. PCT/US2018/028001, dated Oct. 31, 2019.
International Search Report and Written Opinion. Issued by the International Searching Authority (US/ISA) in PCT Application No. PCT/US2021/014708 dated Apr. 15, 2021. 8 pages.
Okumu, Antony, et al. "Novel bacterial topoisomerase inhibitors derived from isomannide." European journal of medicinal chemistry. Apr. 28, 2020. 199, 1-17.
Australian Intellectual Property Office. Examination Report. Issued in Australian Application No. 2018255283 dated May 11, 2021. 2 pages.

* cited by examiner

TYPE II TOPOISOMERASE INHIBITORS AND METHODS OF MAKING AND USING THEREOF

CROSS REFERENCE TO RELATED APPLICATIONS

This application is a national stage application filed under 35 U.S.C. § 371 of PCT/US2018/028001 filed Apr. 17, 2018, which claims the benefit of priority to U.S. Provisional Application Nos. 62/486,227, filed Apr. 17, 2017, and 62/568,075, filed Oct. 4, 2017, which are incorporated by reference herein in their entireties.

BACKGROUND

It has been estimated that 10 million people per year will die from drug-resistant infections by the year 2050 (Jones, J. A., et al. *Med. Chem. Commun.* 2016, DOI: 10. 1039/ C6MD00232C). Thus, infections caused by multidrug-resistant pathogens such as methicillin-resistant *Staphylococcus aureus* (MRSA) and *Pseudomonas aeruginosa* present a critical threat to human health. Surveillance of antibacterial susceptibility among clinical isolates continues to reveal new mechanisms of resistance, including to antibiotics traditionally considered the last lines of defense, such as carbapenems (Morrill, H. J., et al. *Open For. Infect. Dis.* 2015, 2. ofv050) and even colistin (Liu, Y-Y., et al. *Lancet Infect. Dis.* 2016, 16, 161; Schwarz, S., et al. *J. Antimicrob. Chemother.* 2016, 71, 2066).

Despite tremendous advances in genetics and high-throughput screening, the development of antibiotics against novel biological targets has proven exceptionally difficult. The advancement of next-generation inhibitors from established classes of antibiotics such as fluoroquinolones likewise presents difficulties, e.g., preexisting resistance and clinical efficacy/safety differentiation. In light of these and other challenges, antibacterial research in the pharmaceutical industry, long a source of new medicines, has dwindled substantially. Advances in other areas of medicine, including cancer therapy, surgery, and organ transplantation, critically require the availability of effective antibiotics. The confluence of diminished private investment and rising resistance to life-saving medications thus presents an extraordinary threat, to individual patients and to modern medicine. In order to avoid a post-antibiotic era (Alanis, A. *J. Arch. Med. Res.* 2005, 36, 697), new antibacterial therapies and new approaches to preventing, diagnosing, and treating infections are desperately needed.

Bacteria are historically grouped into two categories based on their cellular structure, and this distinction helps to guide the diagnosis and treatment of bacterial infections. Gram-positive (G-pos.) bacteria possess a comparatively thick peptidoglycan cell wall, and Gram-negative (G-neg.) bacteria possess a thinner peptidoglycan layer further surrounded by an outer membrane. Both categories give rise to life-threatening infections, and both have been associated with the emergence of multidrug resistance. *Enterococcus faecium* and Methicillin Resistant *Staphylococcus aureus* (MRSA) represent important examples of G-pos. pathogens. The Centers for Disease Control (CDC) estimates that MRSA alone causes >11,000 fatalities per year in the United States. G-neg. pathogens include *Klebsiella pneumoniae, Acinetobacter baumannii, Pseudomonas aeruginosa,* and various *Enterobacter* species among many others. Together, these six types of G-pos. and G-neg. bacteria, known by the acronym ESKAPE pathogens, comprise some of the most significant causes of multidrug-resistant (MDR) infections today. Effective antibacterial therapy typically abrogates a process that bacteria require to survive (an "essential" target).

Such processes include the synthesis and maintenance of proteins, DNA, and the bacterial cell wall (Kohanski, M. A., et al. *Nature Rev. Microbiol.* 2010, 8, 423). These targets are largely intracellular, meaning that most antibiotics need to penetrate the bacterial cell in order to exert their effect. The outer membrane of G-neg. bacteria constitutes a particularly significant barrier to cell entry, and scientists currently lack a sufficient understanding of the molecular features that govern G-neg. cell penetration (vide infra) (Scorciapino, M. A., et al. *Future Med. Chem.* 2016, 8, 1047). This fact, coupled with the robust set of resistance mechanisms employed by G-neg. microorganisms (Ruppe, E., et al. *Ann. Intensive Care* 2015, 5, 21), renders the cure of infections caused by these bacteria particularly challenging.

DNA replication is essential for the survival of bacteria, and the heterotetrameric (A2B2) bacterial type II topoisomerases DNA gyrase and Topoisomerase IV (TopoIV) are important to this process (Mayer, C., et al. *Chem. Rev.* 2014, 114, 2313; Collin, F., et al. *Appl. Microbiol. Biotechnol.* 2011, 92, 479; Bisacchi, G. S., et al. *Annual Rep. Med. Chem.* 2009, 44, 379; Black, M. T., et al. *Curr. Opin. Invest. Drugs* 2009, 10, 804; Bradbury, B. J., et al. *Curr. Opin. Pharmacol.* 2008, 8, 574; Mitscher, L. A. *Chem. Rev.* 2005, 105, 559; Hooper, D. C. *Clin. Inf. Dis.* 2000, 31 (Suppl. 2), S24). The widely used fluoroquinolone (FQ) class of antibiotics targets this mechanism. The commercially successful and medically important FQ class of antibacterial agents exemplifies the enormous potential of disrupting these targets and reveals the possibility of achieving both Gram-positive and Gram-negative spectrum (Bax, B. D., et al. *Nature* 2010, 466, 935). However, FQ resistance has emerged via a number of mechanisms (Blumberg, H. M., et al. *J. Inf. Dis.* 1991, 163, 1279; Hooper, D. C. *Emerging Inf. Dis.* 2001, 7, 337; Jacoby, G. A. *Clin. Infect. Dis.* 2005, 41 (Suppl. 2), S120). The history of the FQs has also informed more recent drug discovery strategies, notably a focus on minimization of hERG inhibition (a cardiotoxicity liability) and the design of dual-targeting (gyrase and TopoIV) inhibitors to slow clinical resistance emergence (Id.; Blumberg, H. M., et al. *J. Inf. Dis.* 1991, 163, 1279; Wohlkonig, A.; Chan, P. F., et al. *Nat. Strnct. Mol. Biol.* 2010, 17, 1152; Aldred, K. J., et al. *Biochem.* 2014, 53, 1565; Onodera, Y., et al. *J. Antimicrob. Chemother.* 1999, 44, 533; Cheng, J., et al. *Antimicrob. Agents Chemother.* 2007, 51, 2445; Morrow, B. J., et al. *Antimicrob. Agents Chemother.* 2011, 55, 5512). Given exhaustive efforts directed toward FQs over several decades, as well as multiple mechanisms of resistance in the clinic (Hooper, D. C. *Emerging Inf. Dis.* 2001, 7, 337; Jacoby, G. A. *Clin. Infect. Dis.* 2005, 41 (Suppl. 2), S120), the design and synthesis of type II topoisomerase inhibitors with non-FQ chemotypes presents a compelling need. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to Non-FQ Bacterial Type II Topoisomerase Inhibitors (NBTIs), analogs thereof, pharmaceutical compositions thereof, and methods of making and using these compounds and compositions. In further aspects, the disclosed subject matter relates to NBTIs with both gyrase and TopoIV activity, analogs thereof, pharmaceutical compositions thereof, and methods of making and using these compounds and compositions. The disclosed compounds can have potent and balanced inhibition of gyrase and TopoIV (to maximize bacterial killing and slow resistance emergence), minimal hERG inhibition (to reduce cardiotoxicity liabilities), and physicochemical properties consistent with desirable pharmacokinetic (PK) properties. Methods of using the disclosed compounds to treat infections, such as MRSA, MDR *P. aeruginosa*, and other pathogens are also described herein.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
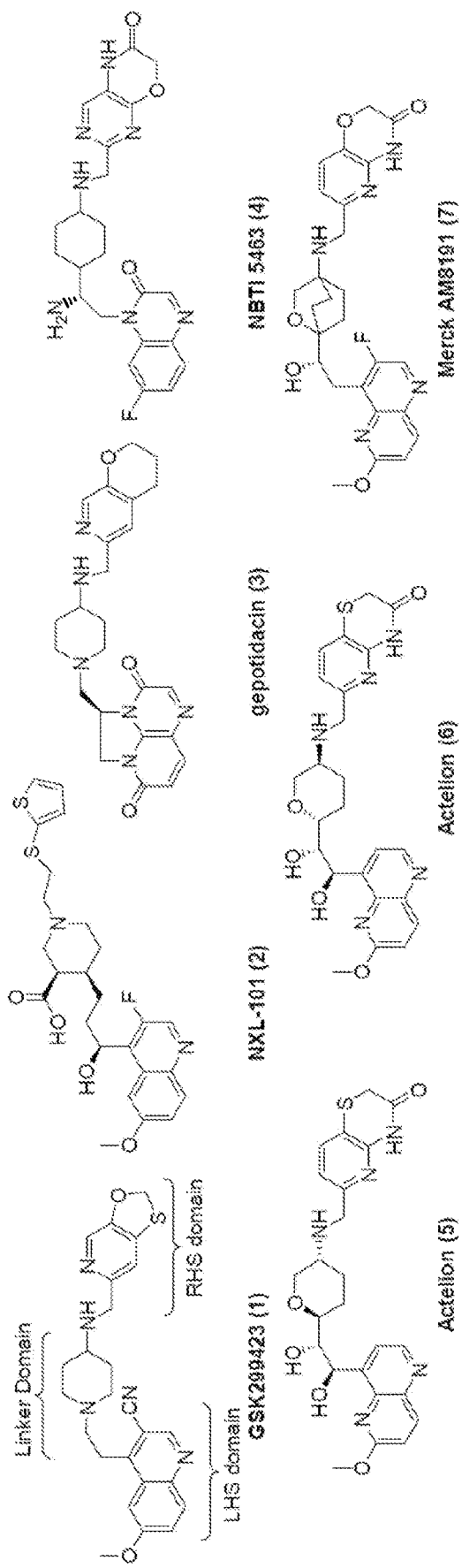
FIG. 1 shows examples of some NBTIs.

The materials, compounds, compositions, and methods described herein may be understood more readily by reference to the following detailed description of specific aspects of the disclosed subject matter, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinases, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., bacterial growth or infection). It is understood that this is typically in relation to some standard or expected value, in other words it is relative, but that it is not always necessary for the standard or relative value to be referred to. For example, "reduces bacterial growth" means decreasing the amount of bacteria cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as bacterial growth or infection), diminishment of extent of infection, stabilized (i.e., not worsening) state of infection, preventing or delaying spread of the infection, preventing or delaying occurrence or recurrence of infection, delay or slowing of infection progression, and amelioration of the infected state.

The term "patient" preferably refers to a human in need of treatment for any purpose, and more preferably a human in need of a treatment to treat infection. However, the term "patient" can also refer to non-human animals, preferably mammals such as dogs, cats, horses, cows, pigs, sheep and non-human primates, among others, that are in need of treatment with a compound as disclosed herein.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H.

Throughout this specification "C(O)" is a short hand notation for C=O, which is also referred to as oxo.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. The term "sulfoxide" is used herein to refer to the sulfo-oxo group represented by the formula —$OS(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

As used herein, the symbol

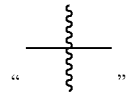

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example

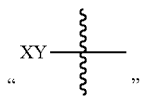

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

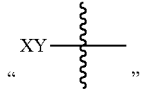

infers that when $R^3$ is "XY", the point of attachment bond is the same bond as the bond by which $R^3$ is depicted as being bonded to $CH_3$.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to infection, an effective amount comprises an amount sufficient to cause a bacterial cell to shrink and/or to decrease the growth rate of the bacterial cells or to prevent or delay other unwanted infection. In some embodiments, an effective amount is an amount sufficient to delay development. In some embodiments, an effective amount is an amount sufficient to prevent or delay occurrence and/or recurrence. An effective amount can be administered in one or more doses. In the case of bacterial infection, the effective amount of the drug or composition may: (i) reduce the number of bacterial cells; (ii) reduce bacterial cell size; (iii) inhibit, retard, slow to some extent and preferably stop bacterial cell infiltration into peripheral organs; (iv) inhibit bacterial growth; (vi) prevent or delay occurrence and/or recurrence of bacterial infection; and/or (vii) relieve to some extent one or more of the symptoms associated with the infection.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Examples of some NBTIs in the literature are provided in FIG. 1. As illustrated by GSK299423 (1) (Bax, B. D., et al. *Nature* 2010, 466, 935) and summarized by Singh (Singh, S. B., et al. *ACS Med. Chem. Lett.* 2014, 5, 609), NBTIs share three common structural domains: a) a left-hand side (LHS) usually comprising a fused bicyclic or tricyclic ring system, b) a linker domain with an amine positioned to interact with D83 of gyrase, and c) a right-hand side (RHS) comprising an aromatic or heteroaromatic ring. X-ray crystallography has been used to study the binding of these compounds to a complex of gyrase and DNA. This research has provided insight at the molecular level into compound binding (Widdowson, K., et al. *Future Med. Chem.* 2010, 2, 1619; Lahiri, S. D., et al. *Antimicrob. Agents Chemother.* 2015, 59, 5278), and this understanding has been enhanced through the study of target mutations conferring resistance to NBTIs.

The LHS binds with uncleaved DNA, and the RHS, generally containing an aromatic or heteroaromatic ring, binds to a dimeric interface of gyrase. Commonly observed gyrase mutations conferring resistance to NBTIs, such as substitutions at D83 and M121, occur at this interface. Extensive previous efforts have optimized the LHS and RHS moieties and illustrated the tolerance for structural variety and innovation in the linker (Mitton-Fry, M. *J. Med. Chem. Rev.* 2017, 52, 281; Tan, C. M., et al. *Antimicrob. Agents Chemother.* 2016, 60, 4830; Black, M. T., et al. *Antimicrob. Agents Chemother.* 2008, 52, 3339; Mitton-Fry, M. J., et al. *Bioorg. Med Chem. Lett.* 2013, 23, 2955; Dougherty, T. J., et al. *Antimicrob. Agents Chemother.* 2014, 58, 2657; Dougherty, T. J., et al. *Antimicrob. Agents Chemother.* 2014, 58, 4250; Nayar, A. S., et al. *Antimicrob. Agents Chemother.* 2015, 59, 331; Reck, F., et al. *Bioorg. Med. Chem.* 2014, 22, 5392; Surivet, J-P., et al. *J. Med Chem.* 2013, 56, 7396; Surivet, J-P., et al. *J. Med. Chem.* 2015, 58, 927; Miles, T. J., et al. *Bioorg. Med. Chem. Lett.* 2011, 21, 7489; Wiles, J. A., et al. *J. Med. Chem.* 2011, 54, 3418; Mitton-Fry, M. J. Novel, Nonquinolone Inhibitors of DNA Gyrase and Topoisomerase IV: Antibacterial Activity and Resistance Mechanisms. Presented at the 243rd National Meeting of the American Chemical Society, San Diego, Calif., 2012, Paper MEDI-257; Singh, S. B., et al. *Bioorg. Med. Chem. Lett.* 2015, 25, 2409; Singh, S. B., et al. *Bioorg. Med Chem. Lett.* 2015, 25, 3636; Singh, S. B., et al. *Med. Chem. Commun.* 2015, 6, 1773; So, W., et al. *Antimicrob. Agents Chemother.* 2015, 59, 4956; Miles, T. J., et al. *Bioorg. Med. Chem. Lett.* 2013, 23, 5437).

The largely solvent-exposed linker domain serves to bridge the LHS and RHS and does not itself play a critical role in binding, evidenced by the linker diversity tolerated in compounds 1-7. In the compounds disclosed herein, a new linker moiety is introduced, which has been found to modulate the physicochemical properties. The structural simplicity and synthetic accessibility of the linker moiety disclosed herein can also result in improved synthetic efficiency and cost effectiveness. Specifically, the disclosed compounds have a 5-amino-1,3-dioxane linker moiety, shown below.

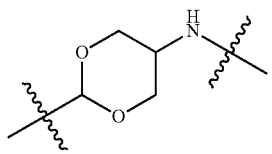 [SMILES: *NC1COC(*)OC1]

The 1,3-dioxane represents a rather uncommon design feature, owing to concerns about potential hydrolytic instability of the acetal. However, in the disclosed compounds, this linker moiety can reduce lipophilicity and amine basicity, improving pharmacokinetic and cardiac safety properties (Pasternak, A., et al. *Bioorg. Med. Chem. Lett.* 1999, 9, 491; Ndubaku, C. O., et al. *ACS Med. Chem. Lett.* 2015, 6, 1241).

In some aspects, disclosed herein are compounds that are Type II Topoisomerase Inhibitors having Formula

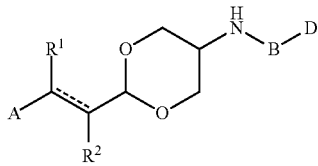

wherein
the dashed line represents a bond that is present or absent, and when the bond is present, $R^1$ and $R^2$ can be cis or trans;
A is a fused bicyclic aryl or bicyclic heteroaryl ring optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol; or A and $R^1$ together form a tricyclic ring optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
B is $C_1$-$C_6$ alkyl or $C_4$-$C_6$ cycloalkyl optionally substituted with one or more oxo, alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
D is a mono or bicyclic aryl or heteroaryl ring optionally substituted with alkyl, heteroalkyl, alkoxy, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

$R^1$ and $R^2$ are, independently, chosen from H, OH, Cl, F, Br, I, CN, $NO_2$, $NH_2$, $CF_3$, $CO_2H$, $CO_2NH_2$, $CO_2NHR^3$, $CO_2R_3$, $C(O)R^3$, $C(O)NH_2$, $C(O)NHR^3$, oxo (i.e., =O), and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol; or $R^1$ is a $C_1$-$C_3$ alkyl or $C_2$-$C_3$ alkenyl, optionally substituted with $R^9$, also bound to A;

each $R^3$ is, independently, chosen from $C_1$-$C_6$ alkyl, $C_1$-$C_6$ cycloalkyl, aryl, heteroaryl, heterocycloalkyl, and heteroalkyl, any of which are optionally substituted with $C_1$-$C_6$ alkyl, $C_1$-$C_6$ alkoxyl, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol; and $R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;

or a pharmaceutically acceptable salt thereof.

In specific examples of Formula I, the dashed line represents a bond and Formula I can thus be represented as Formula IA ($R^1$ and $R^2$ are trans) or IB ($R^1$ and $R^2$ are cis).

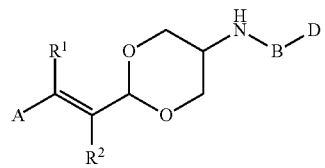

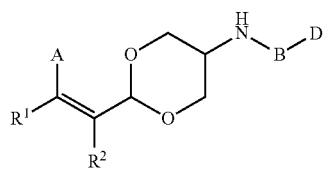

In still other examples, the dashed line in Formula I is absent and Formula I can thus be represented as Formula IC.

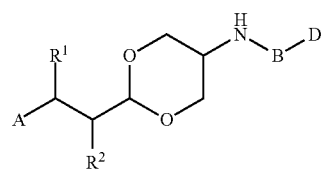

In additional examples, the stereochemistry of the dioxane moiety can be trans, which is shown in Formula ID.

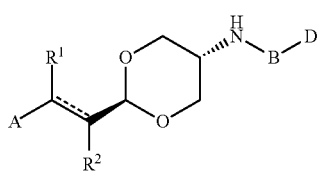

In still other examples, the stereochemistry of the dioxane moiety can be cis. In each of these formulas, the variables R$^1$, R$^2$, R$^3$, A, B, D are as defined herein. Further, unless specifically stated, reference to Formula I herein includes individual references to each of Formulas IA-ID.

The disclosed compounds can have potent and balanced inhibition of gyrase and TopoIV (to maximize bacterial killing and slow resistance emergence), minimal hERG inhibition (to reduce cardiotoxicity liabilities), and physicochemical properties consistent with desirable pharmacokinetic (PK) properties (Lipinski, C. A., et al. *Adv. Drug Delivery Rev.* 1997, 23, 3; Veber, D. F., et al. *J. Med. Chem.* 2002, 45, 2615; Gleeson, M. P. *J. Med. Chem.* 2008, 51, 817; Leeson, P. D., et al. *Nature Rev. Drug Disc.* 2007, 6, 881), and ease of synthesis. Further, these compounds can utilize a mechanistically distinct form of topoisomerase inhibition resulting in antibacterial activity even against highly FQ-resistant strains.

Previous work with NBTIs has helped to clarify their advantages and remaining challenges. The interactions with the target, distinct from those of FQs, lead to a lack of cross-resistance between these two classes of topoisomerase inhibitors (Black, M. T., et al. *Antimicrob. Agents Chemother.* 2008, 52, 3339; Mitton-Fry, M. J.; Brickner, S. J., et al. *Bioorg. Med. Chem. Lett.* 2013, 23, 2955). As such, NBTIs do not face the issue of widespread preexisting resistance in the clinic that would be encountered with a novel FQ. Excellent efficacy against Gram-positive pathogens such as MRSA, both in vitro (Minimum Inhibitory Concentrations, MICs) and in vivo (murine models of infection) has been demonstrated for structurally diverse NBTIs. More recent work has also suggested that an appropriately situated primary amine in the linker domain, such as that found in NBTI 5463 (4, FIG. 1) may be sufficient for antibacterial activity against critically important Gram-negative pathogens such as *P. aeruginosa* (Dougherty, T. J., et al. *Antimicrob. Agents Chemother.* 2014, 58, 2657; Dougherty, T. J., et al. *Antimicrob. Agents Chemother.* 2014, 58, 4250; c) Nayar, A. S., et al. *Antimicrob. Agents Chemother.* 2015, 59, 331) potentially as a result of improved porin penetration. Such effects have also been observed with amine incorporation in other antibacterial drug classes such as cephalosporins.

Among the challenges associated with NBTIs, two deserve special attention. hERG inhibition, with attendant concern about QT-prolongation and cardiovascular safety, must be closely monitored (Reck, F., et al. *Bioorg. Med. Chem.* 2014, 22, 5392; Miles, T. J., et al. *Bioorg. Med. Chem. Lett.* 2011, 21, 7483; Geng, B., et al. *Bioorg. Med Chem. Lett.* 2011, 21, 5432; Reck, F., et al. *J. Med. Chem.* 2011, 54, 7834; Reck, F., et al. *J. Med. Chem.* 2012, 55, 6916; Wiles, J. A., et al. *J. Med. Chem.* 2011, 54, 3418; Singh, S. B., et al. *Bioorg. Med. Chem. Lett.* 2015, 25, 1831; Singh, S. B., et al. *Bioorg. Med. Chem. Lett.* 2015, 25, 2473). At least one clinical candidate, NXL-101 (2, FIG. 1) (Black, M. T., et al. *Antimicrob. Agents Chemother.* 2008, 52, 3339) was withdrawn from clinical studies as a result of QT-prolongation. Historically, NBTIs demonstrate superior inhibition of gyrase as compared to TopoIV, at least in *S. aureus*, permitting resistance by means of single-step mutations to the gyrase target. Improved inhibition of TopoIV has been associated with diminished resistance (Surivet, J-P., et al. *J. Med. Chem.* 2013, 56, 7396; Surivet, J-P., et al. *J. Med. Chem.* 2015, 58, 927).

It has been demonstrated that hERG inhibition from NBTIs often correlates strongly with lipophilicity and amine basicity. While not wishing to be bound by theory, the disclosed 5-amino-1,3-dioxane linker moiety can minimize hERG inhibition via reduced amine basicity and lipophilicity (Pasternak, A., et al. *Bioorg. Med. Chem. Lett.* 1999, 9, 491; Ndubaku, C. O., et al. *ACS Med. Chem. Lett.* 2015, 6, 1241) and provide ready synthetic accessibility across a wide range of derivatives.

Aside from reducing amine basicity and lipophilicity, the readily accessible achiral dioxane linker also enhances synthetic efficiency compared to tetrahydropyran (THP) and oxabicyclooctane linkers (FIG. 1). THPs 5, 6, and oxabicyclooctane 7 all display excellent antibacterial activity, reinforcing the tolerance for structural changes to the linker, provided that the overall molecular topology is maintained. However, synthesis of the linker alone for 7 required 14 steps, and 5 and 6 suffer from synthetic and stereochemical complexity.

In addition to structural diversity, the disclosed compounds can be used to explore a breadth of physicochemical properties, including C Log P and topological polar surface area (TPSA). Variations in LHS, linker substitution, and RHS can be explored systematically. The LHS plays a key role in interacting with DNA. Quinoline LHS A (FIG. 2) has been used successfully by several teams (Wiles, J. A., et al. *J. Med. Chem.* 2011, 54, 3418; Mitton-Fry, M. J. Novel, Non-quinolone Inhibitors of DNA Gyrase and Topoisomerase IV: Antibacterial Activity and Resistance Mechanisms. Presented at the 243rd National Meeting of the American Chemical Society, San Diego, Calif., 2012, Paper MEDI-257), and 1,5-naphthyridine B (FIG. 2) has likewise seen extensive usage (Singh, S. B., et al. *Bioorg. Med. Chem. Lett.* 2015, 25, 2409; Singh, S. B., et al. *Bioorg. Med. Chem. Lett.* 2015, 25, 3636; Singh, S. B., et al. *Med Chem. Commun.* 2015, 6, 1773). LHS C (FIG. 2) dramatically reduces the lipophilicity of the planned analogs (ca. 2C Log P units versus A) and has been shown to provide potent analogs in several reports. Substitution of the methoxy group of LHS C with fluorine, as in LHS D (FIG. 2), has been shown previously to reduce the undesired inhibition of cardiac ion channels, and D is the core for the promising Gram-negative lead NBTI 5463. Additionally, tricyclic LHS moieties such as LHS E-H (FIG. 2) have also shown promise (Miles, T. J., et al. *Bioorg. Med. Chem. Lett.* 2013, 23, 5437; Singh, S. B., et al. *Bioorg. Med. Chem. Lett.* 2015, 25, 1831; Singh, S. B., et al. *Bioorg. Med Chem. Lett.* 2015, 25, 2473; Miles, T. J., et al. *Bioorg. Med. Chem. Lett.* 2016, 26, 2464; Biedenbach, D. J., et al. *Antimicrob. Agents Chemother.* 2016, 60, 1918). Similar evidence for potency has been sought in choosing RHS moieties. The RHS binds to the dimeric gyrase interface and has also been observed to impact target potency against TopoIV. Consequently, variations of the RHS are can be used to improved TopoIV potency and diminished resistance. Moreover, the choice of RHS also appears to impact the degree of inhibition of the hERG and other ion channels. Whereas all of these moieties have been used in potent inhibitors, RHS 2-4, especially RHS 4, have shown reduced hERG inhibition as compared to RHS 5 and RHS 6 (Surivet, J-P., et al. *J. Med. Chem.*

2015, 58, 927). Notably, RHS 1 is a key feature of Phase 2 clinical candidate GSK2140944, RHS 2 was used for an earlier candidate GSK966587, and RHS 7 constitutes the RHS of the analog used in breakthrough crystallographic studies. The choice of RHS also enables variation in lipophilicity, hydrogen bond donor/acceptor number, and TPSA. For example, RHS 8 is isosteric to but more lipophilic than RHS 2.

In view of the above, specific examples disclosed herein are compounds of Formula L wherein A is a fused bicyclic aryl or bicyclic heteroaryl ring having Formula II.

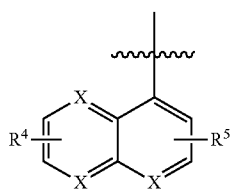

wherein
each X is, independently, CH or N; and
$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can have Formula II, wherein $R^4$ and $R^5$ are, independently, chosen from H, Cl, F, Br, I, CN, OH, and unsubstituted $C_1$-$C_6$ alkyl or $C_1$-$C_6$ alkoxyl. In further examples, $R^4$ and $R^5$ are, independently, chosen from H, Cl, F, CN, OH, and methoxyl. In further examples, $R^4$ and $R^5$ are, independently, chosen from F and methoxyl.

In still further examples, all X's are CH. In yet further examples, one X is CH and the other two X's are N. In yet further examples, two X's are CH and the other X is N. In still further examples, all X's are N.

In further examples, disclosed herein are compounds of Formula I, wherein A is a fused bicyclic aryl or bicyclic heteroaryl ring having Formula III.

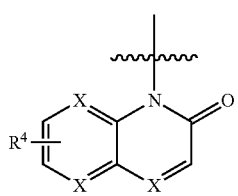

wherein
each X is, independently, CH or N;
$R^4$ is chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can have Formula III, wherein $R^4$ is chosen from H, Cl, F, Br, I, CN, OH, and unsubstituted $C_1$-$C_6$ alkyl or $C_1$-$C_6$ alkoxyl. In further examples, $R^4$ is chosen from H, Cl, F, CN, OH, and methoxyl. In further examples, $R^4$ is chosen from F and methoxyl. In specific examples of Formula III, each X is N. In other examples, two X's are CH and the other X is N. In other examples, two X's are N and the other X is CH.

In still further examples, disclosed herein are compounds of Formula I, wherein A is a bicyclic aryl or bicyclic heteroaryl that together with $R^L$ forms a tricyclic ring. When $R^1$ is a $CH_2$, this can be shown by Formula IX, X, XI, or XII.

In specific examples, A can be Formula IX:

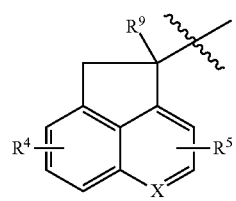

wherein
X is CH, N, or $CR^8$;
$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
$R^8$ is Cl, F, CN, OH, $OCH_3$, $CH_3$, or $NH_2$; and
$R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can be Formula X:

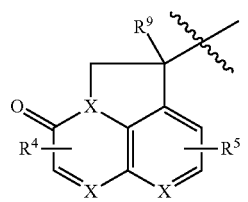

wherein
each X is, independently, CH, N, or CRS;
$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
each $R^8$ is, independently, Cl, F, CN, OH, $OCH_3$, $CH_3$, or $NH_2$; and $R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can be Formula XI:

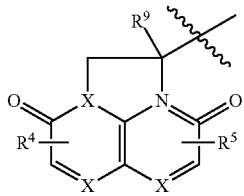
XI wherein
each X is, independently, CH, N, or $CR^8$;
$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
each $R^8$ is, independently, Cl, F, CN, OH, $OCH_3$, $CH_3$, or $NH_2$ and
$R^9$ is H or $C_1$-$C_6$ alkyl.

In specific examples, A can be Formula XII:

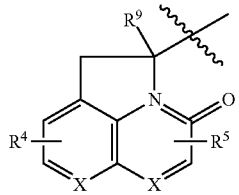
XII wherein
each X is, independently, CH, N, or $CR^8$;
$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol; and
each $R^8$ is Cl, F, CN, OH, $OCH_3$, $CH_3$, or $NH_2$; and
$R^9$ is H or $C_1$-$C_6$ alkyl.

In specific examples, of Formula I, A can be

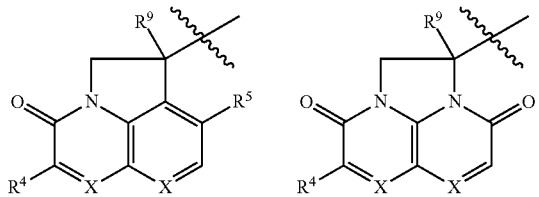

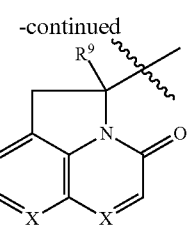

wherein each of $R^4$, $R_5$, and $R^9$ can be independently, chosen from Cl, F, CN, OH, $OCH_3$, $CH_3$, or $NH_2$.

In specific examples, of Formula IX, X, XI, and XII, $R^5$ can be F.

In further examples, disclosed herein are compounds of Formula I, wherein B is a $C_1$-$C_6$ alkyl or $C_4$-$C_6$ cycloalkyl chosen from unsubstituted methyl, ethyl, propyl, butyl, cyclobutyl, or cyclopentyl. In specific examples, B is $CH_2$, —C(=O)—, or cyclobutyl. B can also be CONH or $CH_2NH$—.

In still further examples, disclosed herein are compounds of Formula I, wherein D is aryl or heteroaryl ring having Formula IV-VIII or XIII.

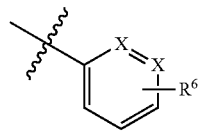
IV

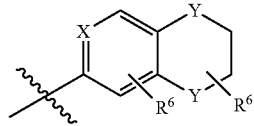
V

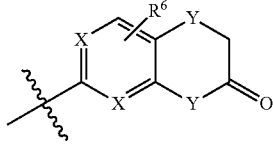
VI

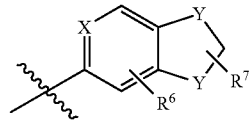
VII

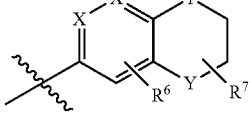
VIII

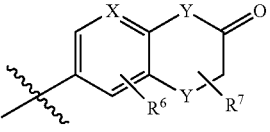
XIII wherein
each X is, independently, chosen from CH or N;
each Y is, independently, chosen from O, S, NH, or $CH_2$; and
$R^6$ and $R^7$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, D can have Formula IV-VIII or XIII, wherein $R^6$ and $R^7$ are, independently, chosen from H, Cl, F, Br, I, CN, OH, and unsubstituted $C_1$-$C_6$ alkyl or $C_1$-$C_6$ alkoxyl. In further examples, $R^6$ and $R^7$ are, independently, chosen from H, Cl, F, CN, OH, or methoxyl. In further examples, $R^6$ and $R^7$ are, independently, chosen from F or methoxyl. In further examples, $R^6$ and $R^7$ are both H. In still further examples, both Y are O. In other examples, one Y is S and the other is O. In still other examples, one Y is NH and the other is O.

In yet further examples, disclosed herein are compounds of Formula I, wherein $R^1$ and $R^2$ are, independently, chosen from H, F, OH, or $NH_2$. In specific examples, $R^2$ is $NH_2$. In other examples, $R^2$ is H or OH. In further examples, $R^1$ is H or OH. In specific examples, $R^2$ is oxo (i.e., =O). In other examples, $R^1$ is oxo (i.e., =O). Incorporation of a hydroxyl substituent (at $R^1$ or $R^2$) reduces lipophilicity by ca. 1.5 C Log P units and has been shown in some cases to impact hERG inhibition and other properties.

Figure 2:
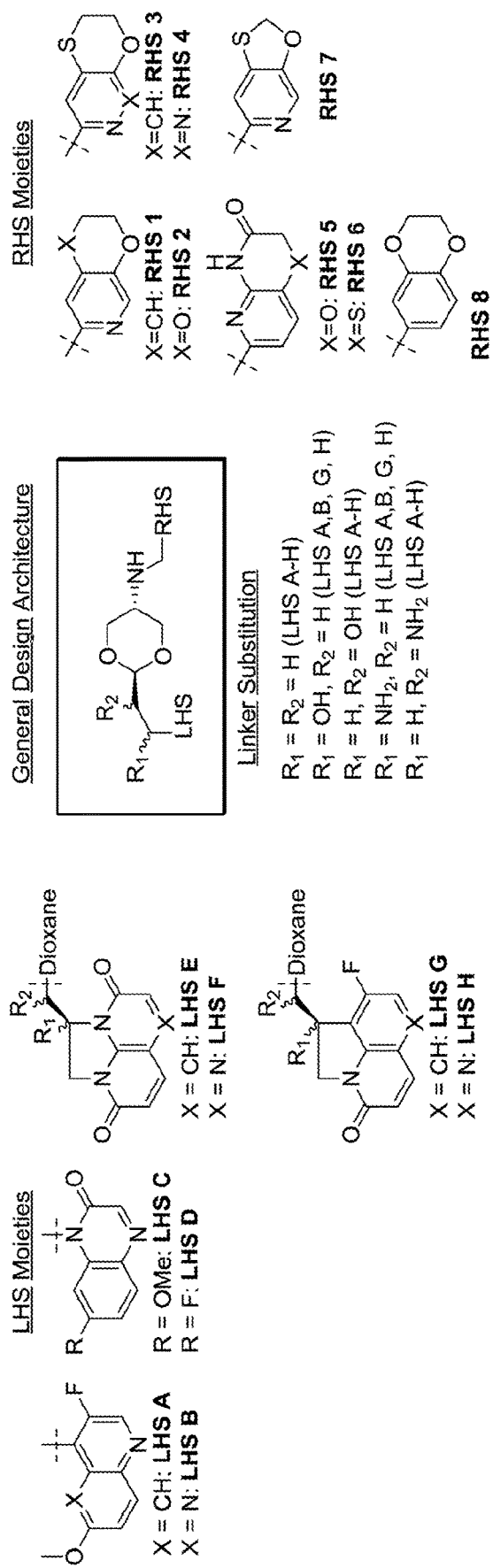
FIG. 2 shows an exemplary architecture of compounds disclosed herein with examples of different LHS, RHS, and linker substitutions.

Some specific examples of compounds disclosed herein are shown in the examples and in FIG. 2.

Additional examples of compounds disclosed herein are shown below.

15

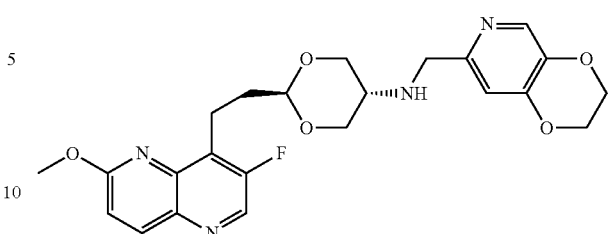

60

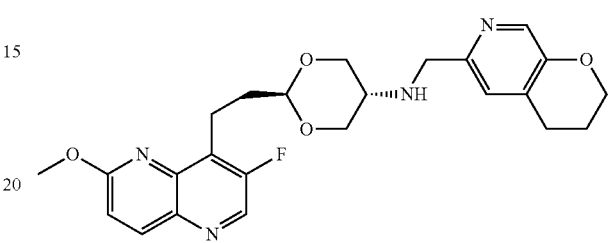

17

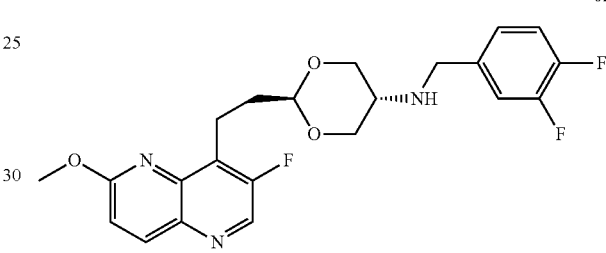

61

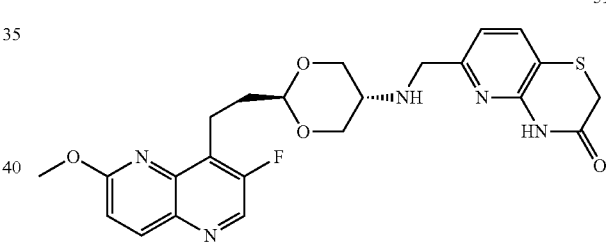

18

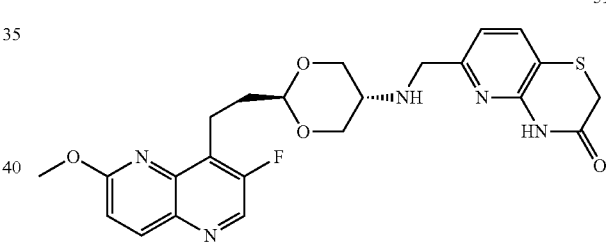

62

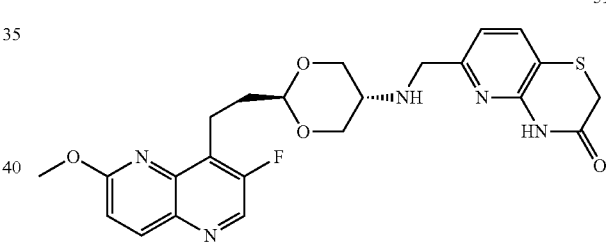

59

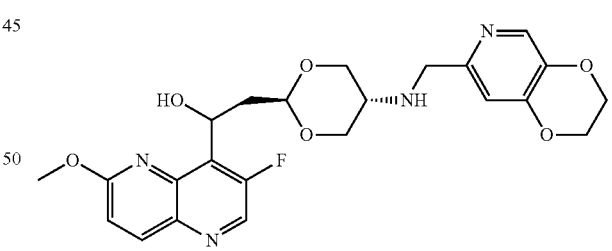

83

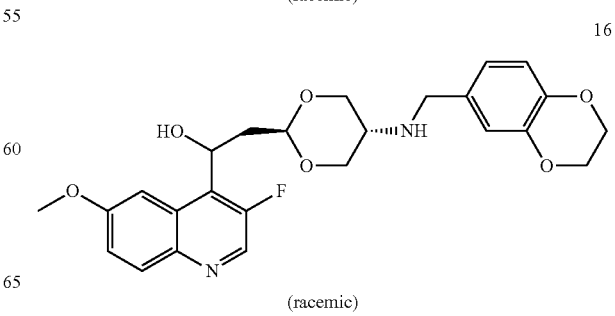

(racemic)

16

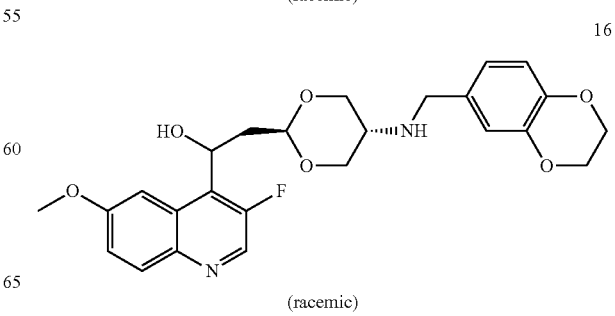

(racemic)

20
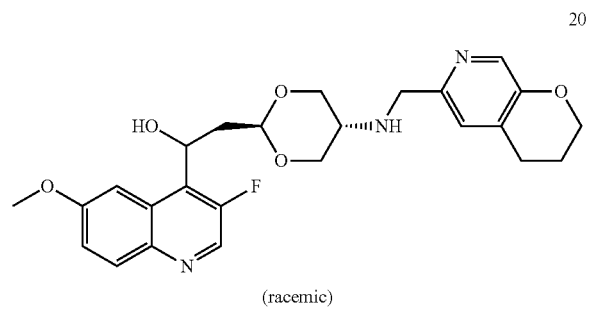
(racemic)
19
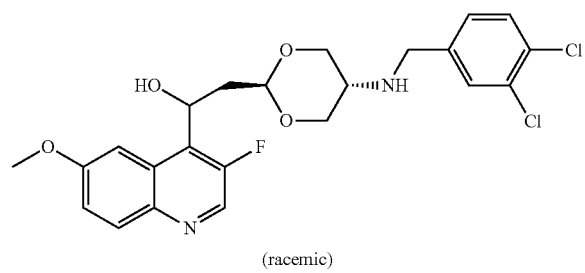
(racemic)
46
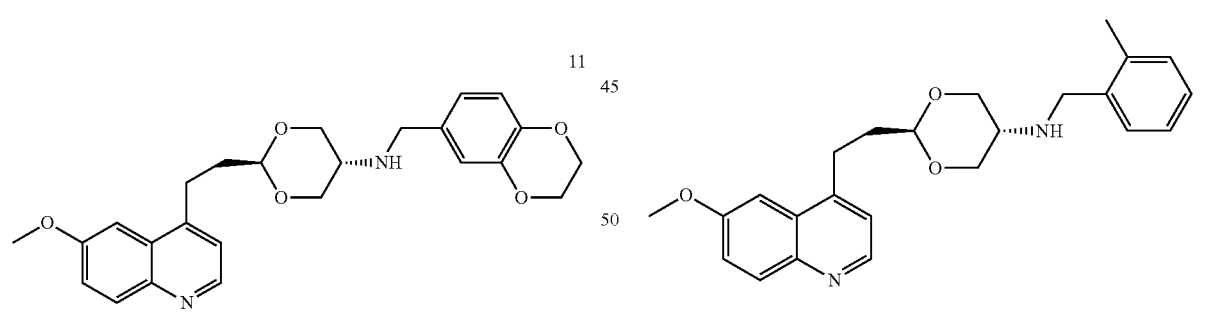
(racemic)
11
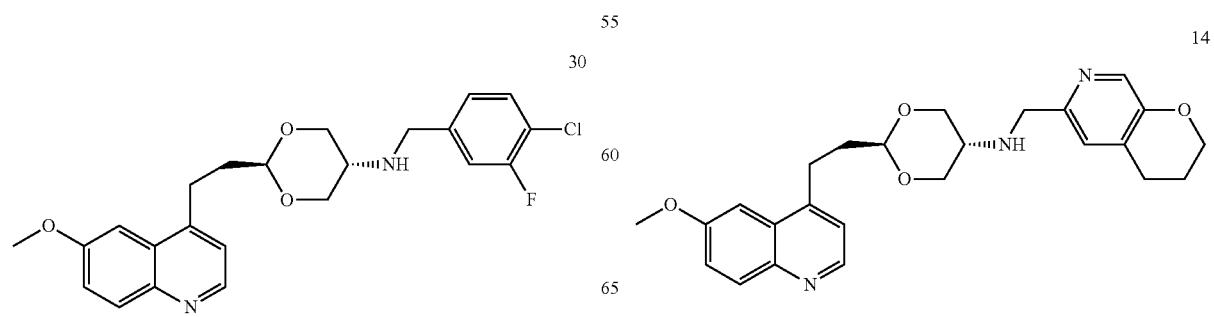
30
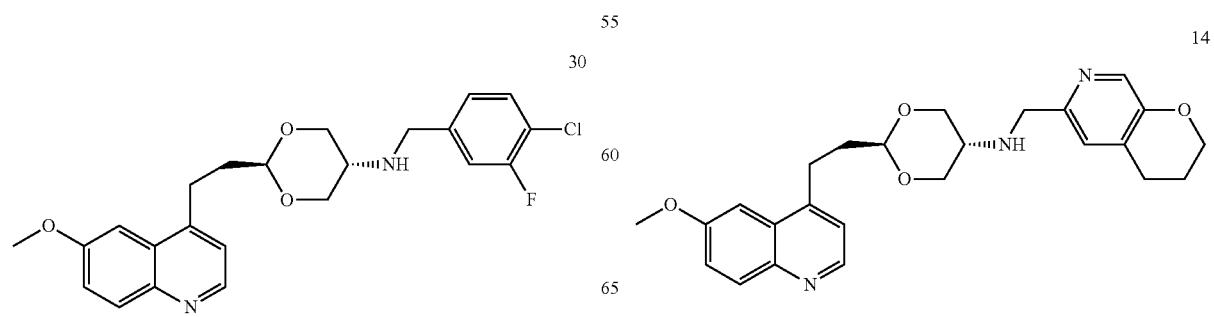
12
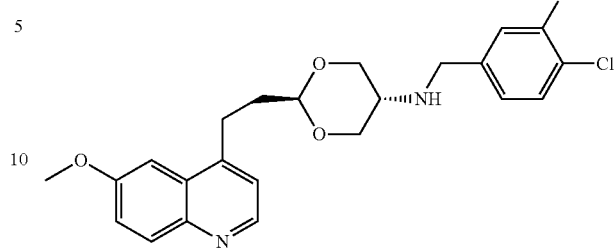
31
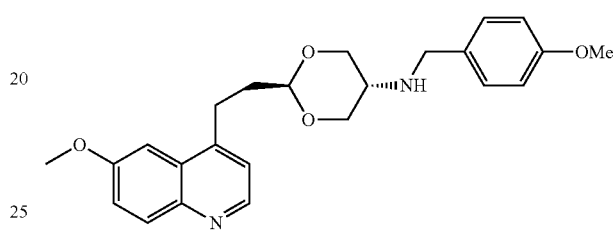
13
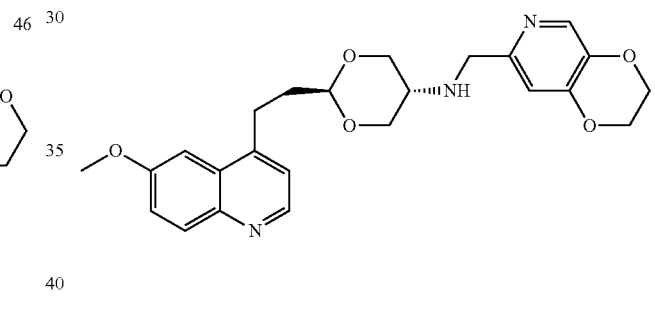
32
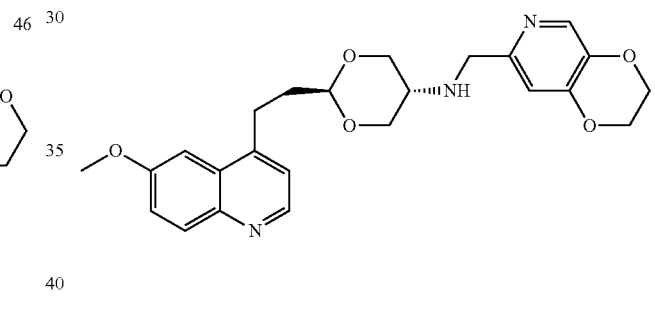
14
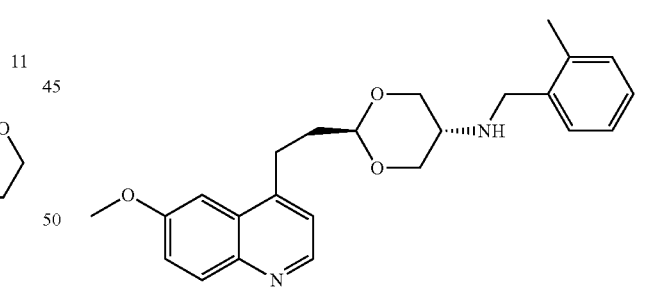

33
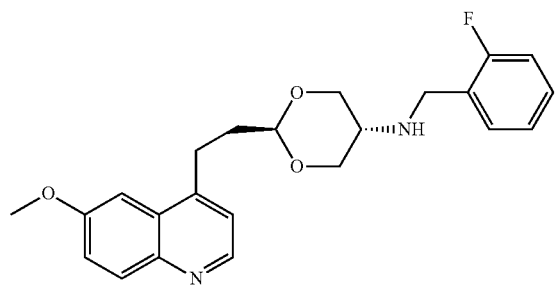
21
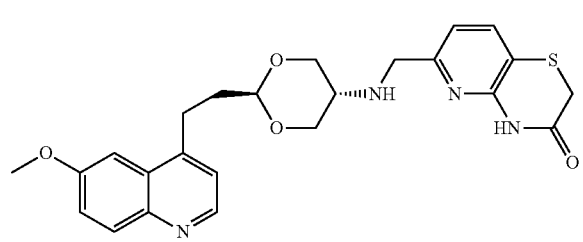
34
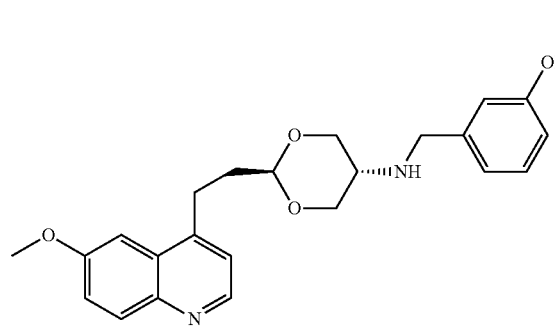
22
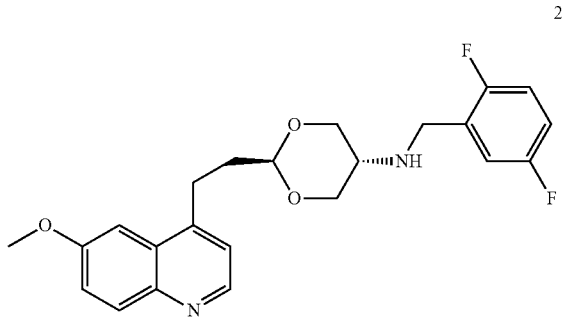
35
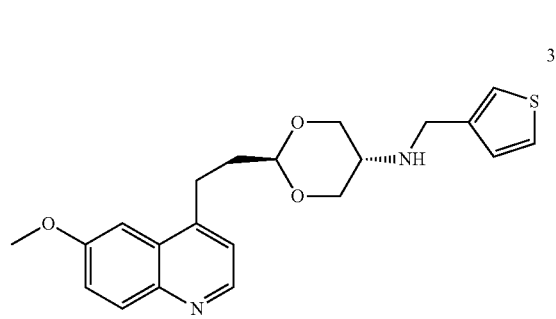
23
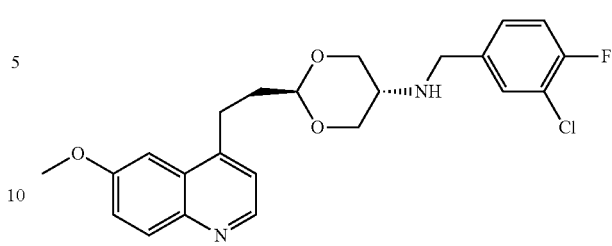
36
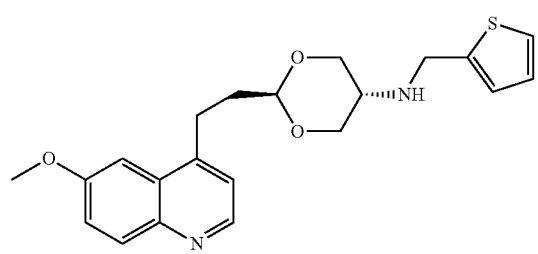
24
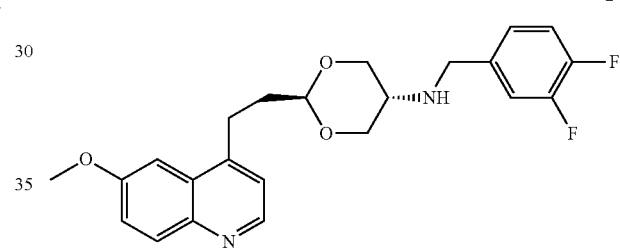
37
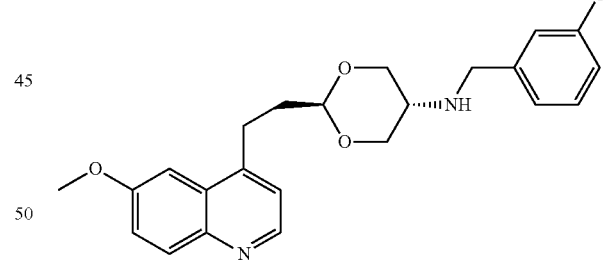
25
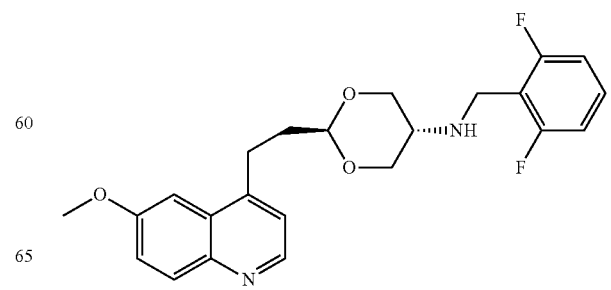

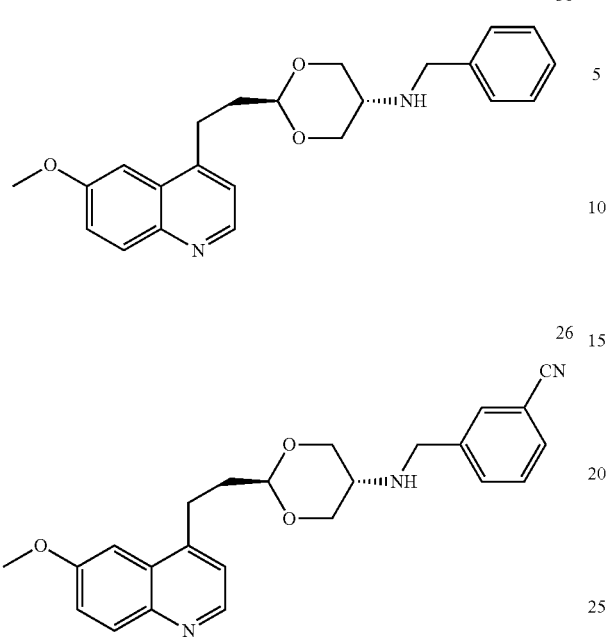
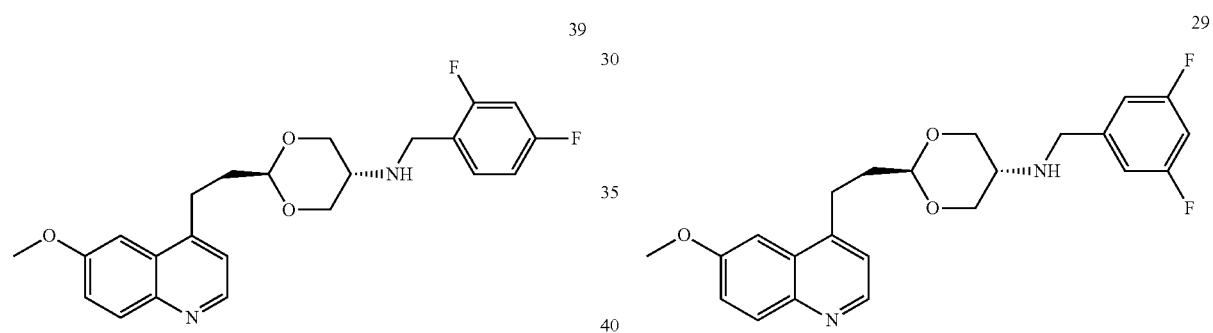
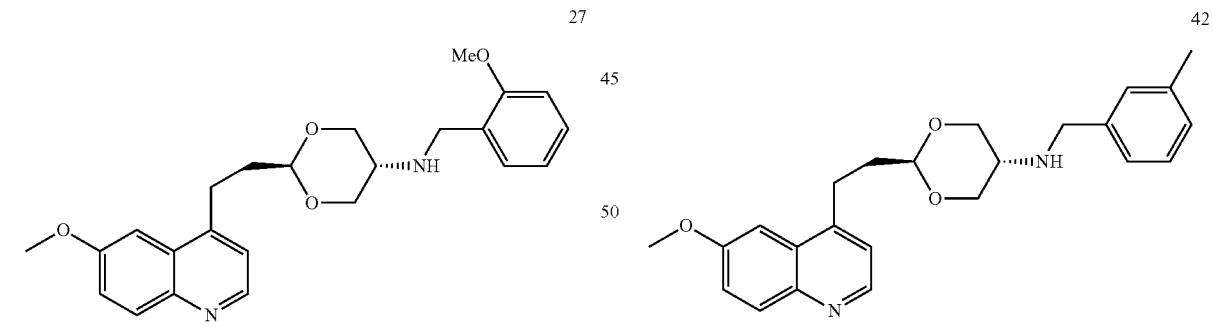
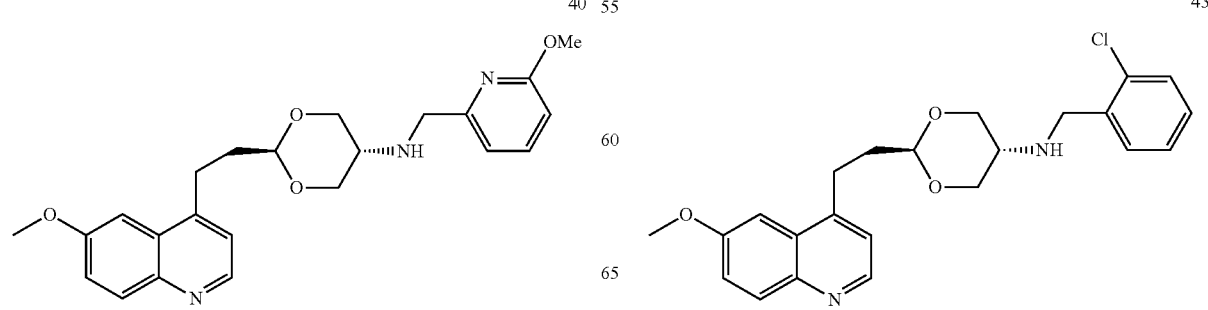

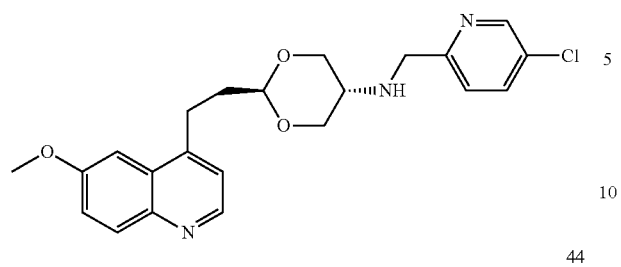
69
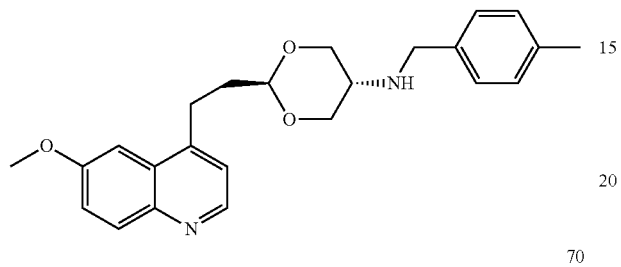
44
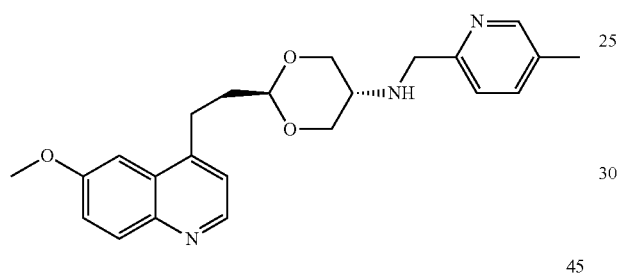
70
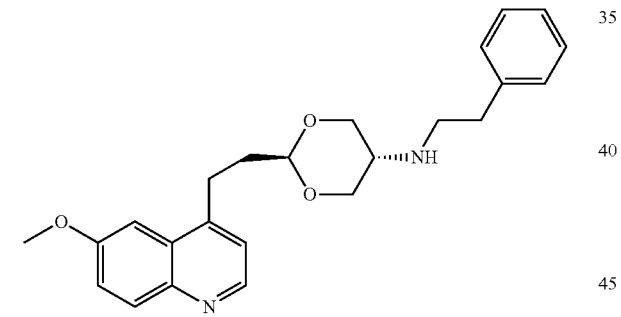
45
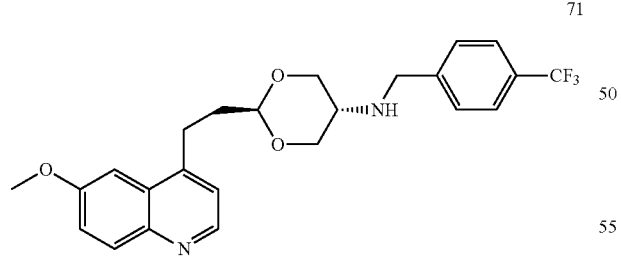
71
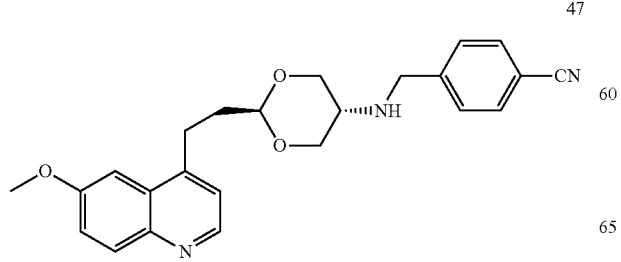
47
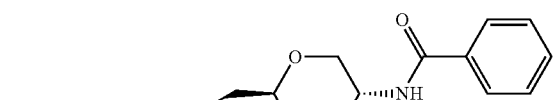
75
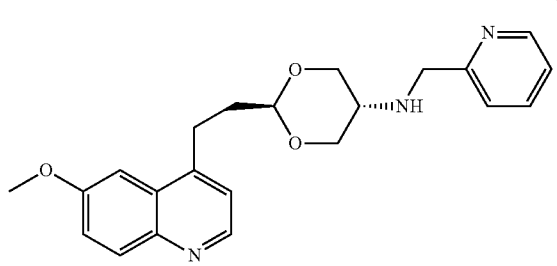
48
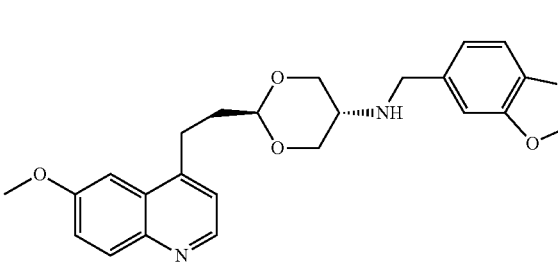
79
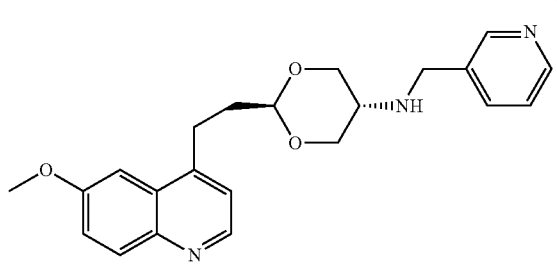
49
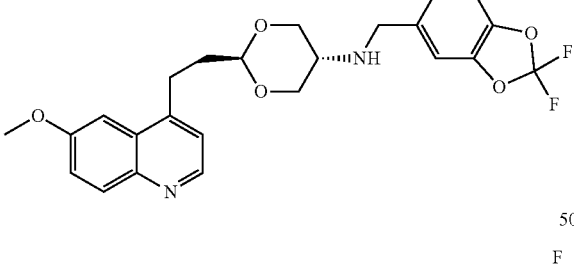
80
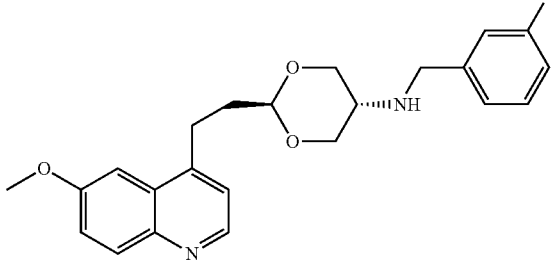
50

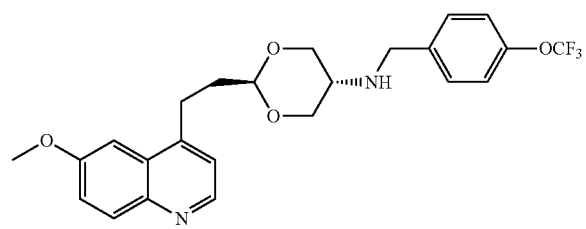
81
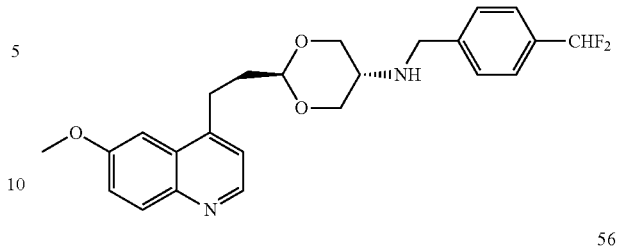
85
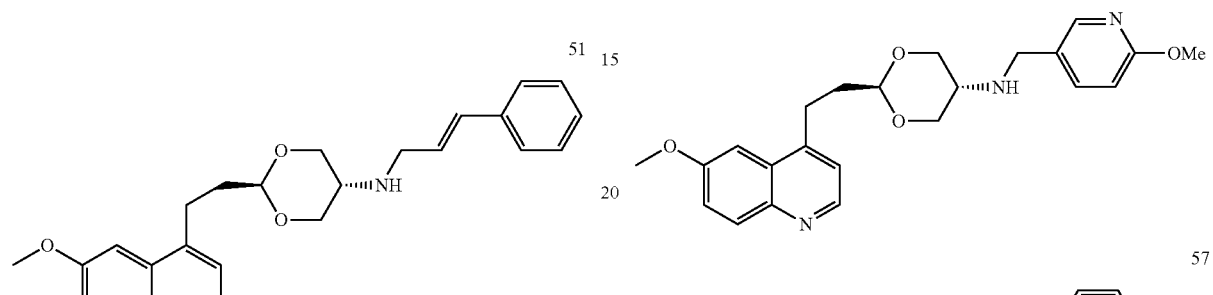
51
56
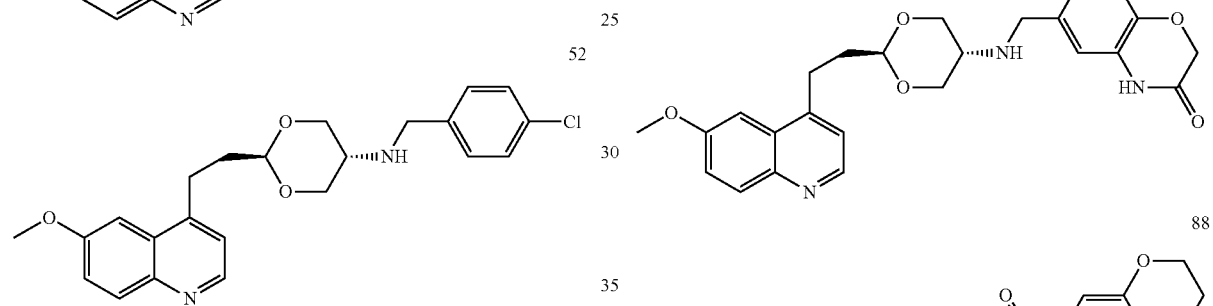
52
57
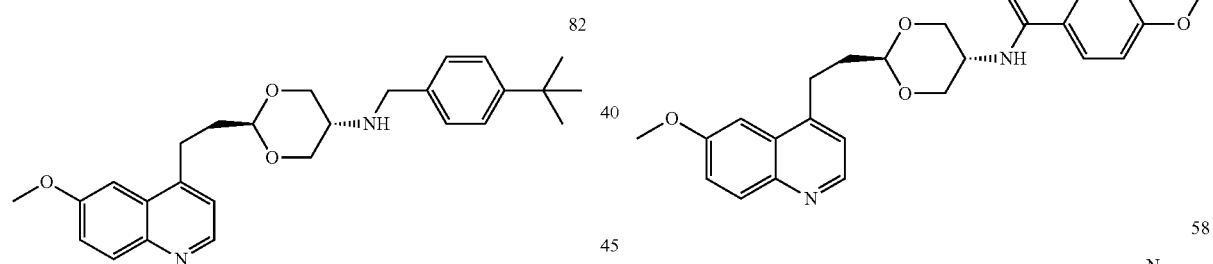
82
88
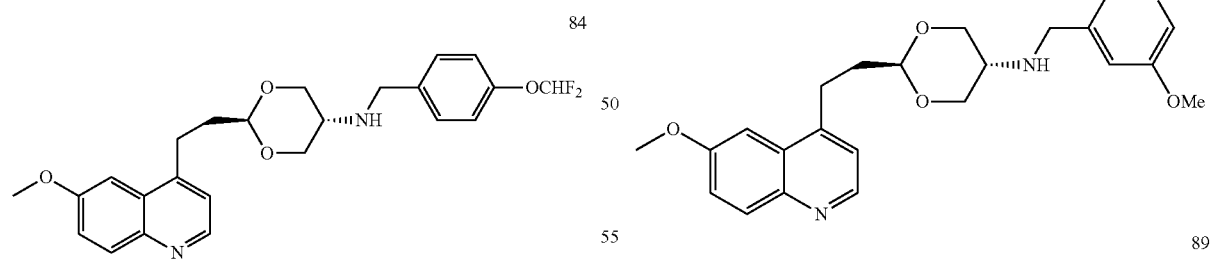
84
58
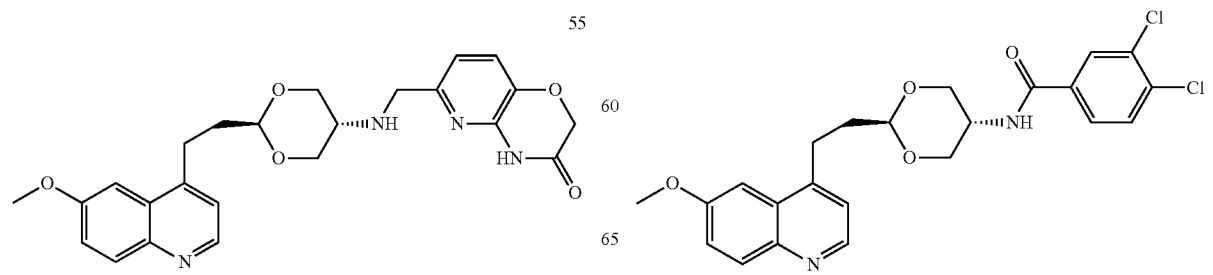
55
89

-continued

2

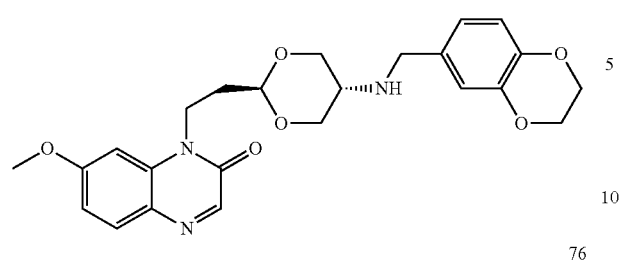

76

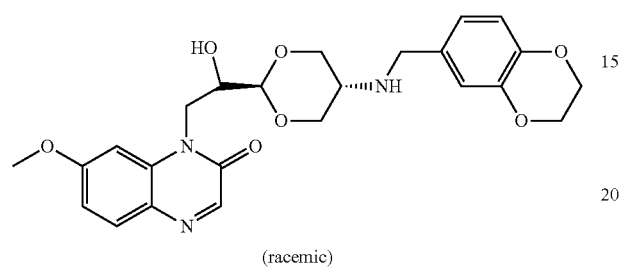

(racemic)

3

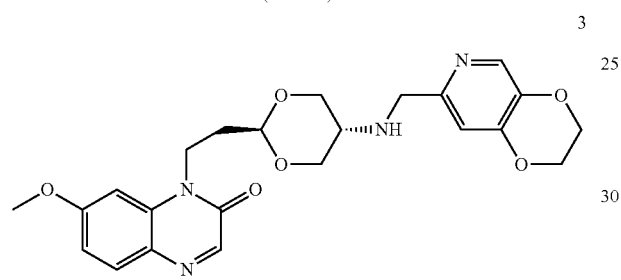

77

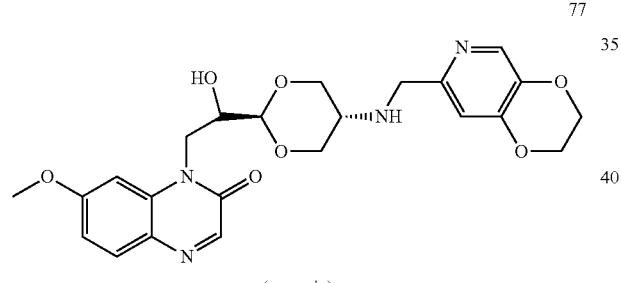

(racemic)

6

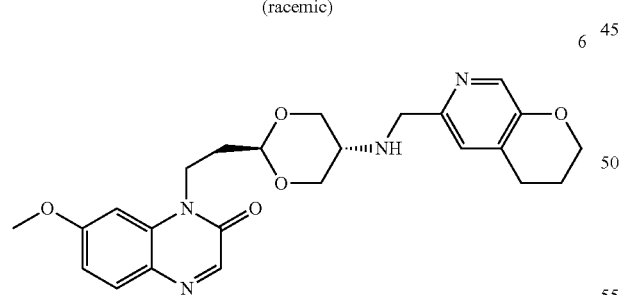

78

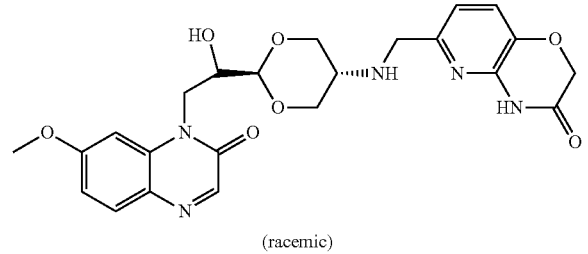

(racemic)

-continued

7

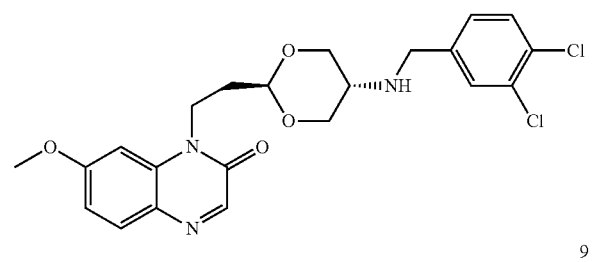

9

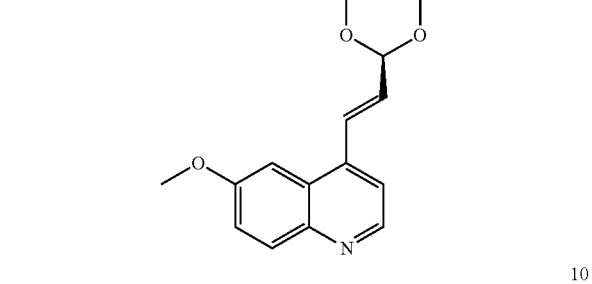

10

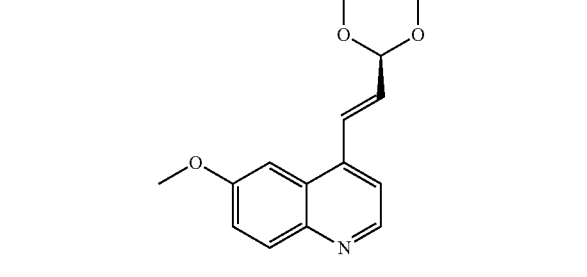

Method of Use

The compounds disclosed herein can be used to treat infections and inhibit the growth of bacteria. In certain examples, disclosed are methods of treating an infection in a patient, comprising administering to the patient a therapeutically effective amount of any of the compounds disclosed herein. Specific examples of infections that can be treated include, but are not limited to, *Actinobacter, Actinomycetes, Bacilli, Bortedellen, Clostridia, Corynebacteria, Enterobacter, Enterococci, Helicobacter, Haemophilus,*

*Klebsiella, Listeria, Alycobacteria, Neisseria, Shigella, Salmonella*, tuberculosis bacteria, and *Yersinia*.

In some examples, the disclosed compounds can be used to treat infections caused by resistant G-pos. bacteria such as Methicillin Resistant *Staphylococcus aureus* (MRSA). Despite newly launched drugs and others in clinical development, the CDC characterizes MRSA as a serious threat, its second highest level of concern. These disclosed methods can involve administering a compound disclosed herein to the infected human or animal or the human or animal at risk of being infected. In some specific examples, the infected individual has cyctic fibrosis.

In some examples, the disclosed compounds can be used to treat infections caused by resistant G-neg. pathogens such as *P. aeruginosa*. Infections caused by G-neg. bacteria in general, and MDR *P. aeruginosa* in particular (Wagner, S., et al. *J. Med. Chem.* 2016, 59, 5929), represent a key need in antibacterial drug discovery that is currently underrepresented by approaches in clinical development. The additional permeability barrier imposed by the outer membrane of G-neg. organisms (Zgurskaya, H. I., et al. *ACS Infect. Dis.* 2015, 1, 512), as well as other resistance mechanisms such as robust multidrug efflux transporters, make the identification of potential new therapies particularly challenging. These disclosed methods can involve administering a compound disclosed herein to the infected human or animal or the human or animal at risk of being infected.

In some examples, the disclosed compounds can be used to treat infections caused by *Enterococcus faecium, Klebsiella pneumoniae, Acinetobacter baumannii*, various *Enterobacter*, and *Neisseria gonorrhoeae*. Further examples include the following diseases include: tuberculosis; Pneumonia; Typhoid; Paratyphoid; Syphilis, Gastritis; Gastroenteritis; Ruhr; Pestilence; Enteritis; extraintestinal infections, peritonitis and appendicitis with *E. coli* and intestinal infections with EHEC, EPEC, ETEC and EIEC; Cholera, Legionnaires' disease, whooping cough, brucellosis, Lyme disease, leptospirosis, typhus, trachoma, gonorrhea, meningitis, septicemia, leprosy etc. These methods can involve administering a compound disclosed herein to the infected human or animal or the human or animal at risk of being infected.

In other examples, disclosed herein are methods of treating an infection in a patient, comprising administering to the patient a therapeutically effective amount of any of the compounds disclosed herein.

In these disclosed methods, one can treat humans with infections, but also can treat livestock (horses, cows, pigs, sheep, goats etc.), poultry, and companion animals (dogs, cats, rabbits, etc.). The compositions or organisms can be administered alone or in combination with other therapeutics or nutritional supplements, for example the composition can be combined into a feed.

Combinations

The disclosed compounds can also be combined with additional antimicrobial agents. For example, the disclosed compounds can be combined with one or more of Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium, Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Cefforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodiumr; Nafcillin Sodium; Nalidixate Sodium; Nalidixic Acid; Natainycin; Nebramycin; Neomycin Palmitate; Neomycin Sulfate; Neomycin Undecylenate; Netilmicin Sulfate; Neutramycin;

Nifuiradene; Nifuraldezone; Nifuratel; Nifuratrone; Nifurdazil; Nifurimide; Nifiupirinol; Nifurquinazol; Nifurthiazole; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride, Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisboxazole Diolamine; Sulfomyxin; Sulopenem; Sultamricillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin.

The disclosed compounds can also be combined with foaming agents such as sodium laureth ether sulfate (SLES), sodium lauryl dodecyl sulfate (SDS), disodium laureth sulfosuccinate, ammonium lauryl sulfate (ALS), sodium pareth sulfate, and sodium coceth sulfate. Foaming agents can be present at from about 1% to about 70%, about 5% to about 50%, about 10% to about 30%, or about 1% to about 5% by weight.

The disclosed compounds can, in some examples, further comprise one or more antibiotics. Examples of antibiotics include amikacin, gentamicin, kanamycin, neomycin, streptomycin, tobramycin, bacitracin, clindamycin, daptomycin, lincomycin, linezolid, metronidazole, polymyxin, rifaximin, vancomycin, penicillin, cephalosporin, cephazolin, cephalexin, erythromycin, azithromycin, ciprofloxacin, levofloxacin, sulfadiazine, minocycline, tetracycline, and rifampin. The proportion of antibiotics can be about 0.001% to about 10%, about 0.01% to about 5%, about 0.1% to about 10%, or about 1% to about 5% by weight.

The disclosed compounds can, in some examples, further comprise additional agents such as acyclovir, cephradine, malphalen, procaine, ephedrine, adriamycin, dauno, mycin, plumbagin, atropine, quinine, digoxin, and quinidine, cephradine, cephalothin, cishydroxy-L-proline, melphalan, nicotinic acid, nitric oxide, nitroglycerin, chemodeoxycholic acid, chlorambucil, paclitaxel, sirolimus, 5-flurouracil, paclitaxel, mercaptoethanesulfonate, verapamil, or antifungal agents. The proportion of these additional agents can be about 0.001% to about 10%, about 0.01% to about 5%, about 0.1% to about 10%, or about 1% to about 5% by weight.

In some examples, the disclosed compounds can further comprise anti-inflammatory agents. Examples of such agents include acetaminophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin, trolamine. The proportion of these anti-inflammatory agents can be present in the formulation at from about 1% to about 70%, about 5% to about 50%, about 10% to about 30%, or about 1% to about 5% by weight.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S.

Application Publication No. 20020035243 also describes compositions for transporting biological moieties across cell membranes for intracellular delivery. Compounds can also be incorporated into polymers, examples of which include poly (D-L lactide-co-glycolide) polymer, poly[bis(p-carboxyphenoxy) propane:sebacic acid] in a 20:80 molar ratio (as used in GLIADEL); chondroitin; chitin; and chitosan.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

General Synthesis

Examples AB-0002, 0003, 0006, and 0007 can be prepared from compound 13 and the requisite aldehyde according to Scheme 1.

Scheme 1

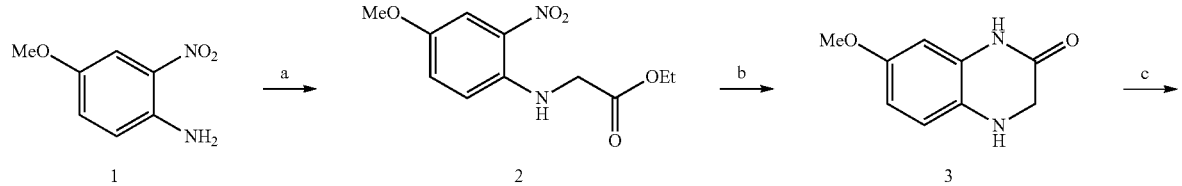

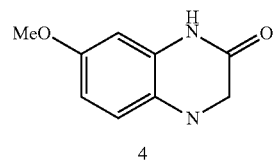

Reagents: (a) ethyl bromoacetate, K₂CO₃, 150° C., 79%; (b) H₂, Pd/C, MeOH/AcOH, room temp, used directly; (c) NaOH, H₂O₂, water, 80° C., then AcOH, room temp, 51% (2 steps).

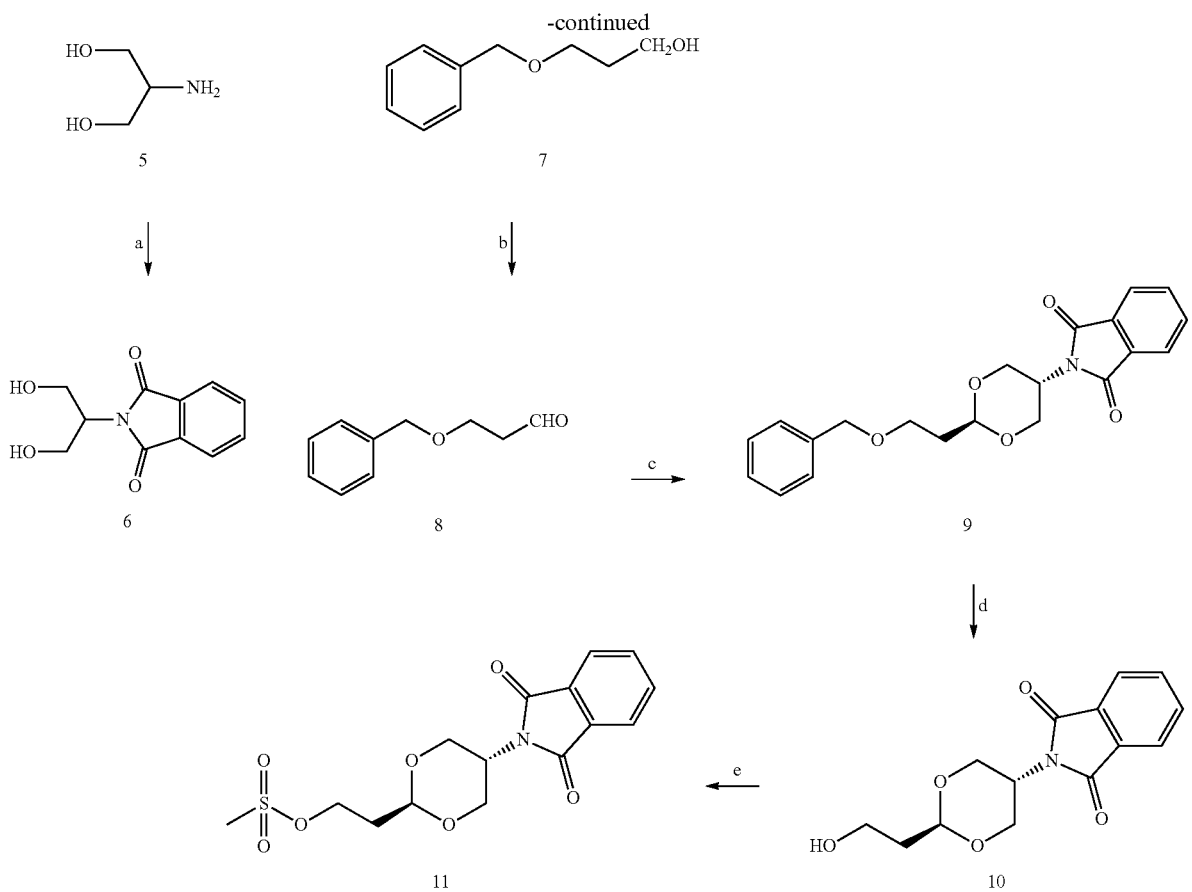
Reagents: (a) phthalic anhydride, toluene, 105° C., 91%; (b) Dess-Martin periodinane, dichloromethane, room temp, 95%; (c) p-toluenesulfonic acid (cat.), toluene, 110° C., 66%; (d) H₂, Pd/C, MeOH, room temp, 89%; (e) methanesulfonic anhydride, pyridine, room temp, 81%.
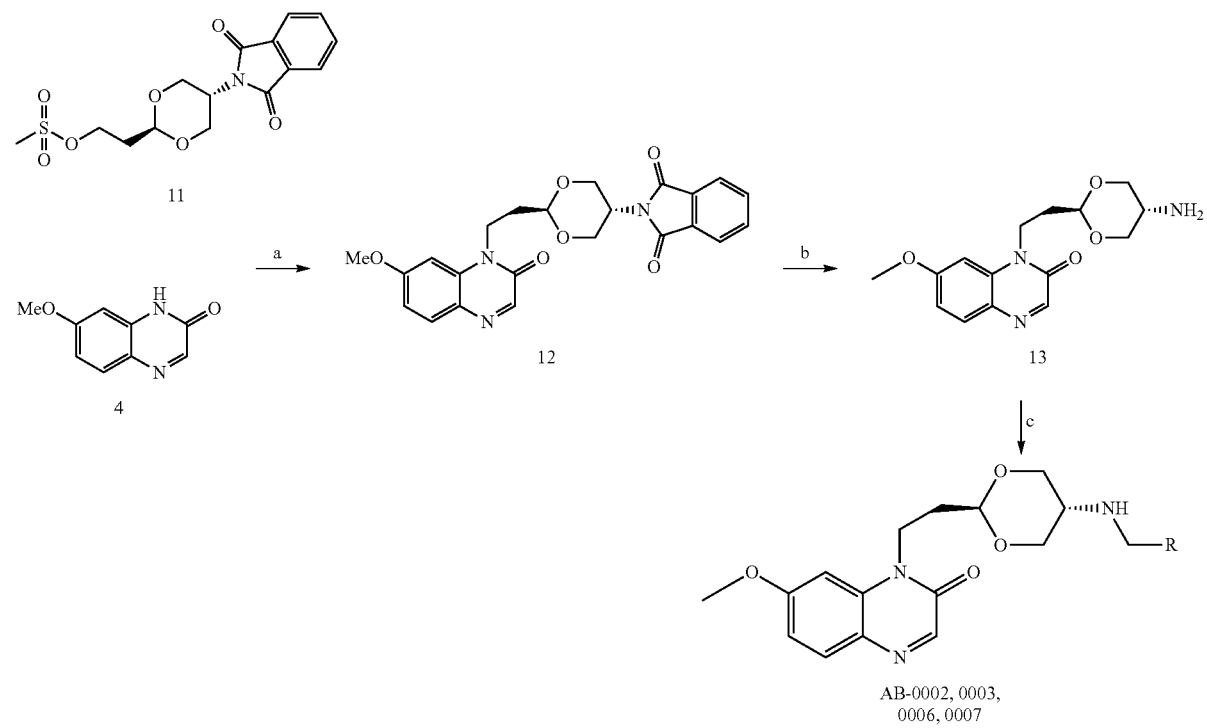
Reagents: (a) Cs₂CO₃, DMSO, 30 min at 0° C., overnight at room temp, 36%; (b) ethanolamine, ethyl acetate, 70° C., 76%. (c) RCHO, ZnCl₂, methanol, NaBH₃CN, room temp, overnight.

Ethyl N-(4-methoxy-2-nitrophenyl)glycinate (2)

A mixture of 4-methoxy-2-nitroaniline (1, 500 mg, 2.91 mmol), ethyl bromoacetate (4 mL, 35.35 mmol), and potassium carbonate (804 mg, 5.92 mmol) was heated at 150° C. for 4.5 h. The mixture was cooled to room temperature, and aqueous sodium hydroxide solution (1M, 12 mL) was added. This mixture was extracted with dichloromethane. The combined organic phases were dried over magnesium sulfate and concentrated under reduced pressure. Chromatography on silica gel with hexanes/ethyl acetate (5:1) afforded compound 2 as a red solid (588 mg). $^1$H NMR (DMSO-d$_6$) δ: 1.18-1.23 (t, 3H); 3.75 (s, 3H); 4.13-4.18 (q, 2H); 4.23-4.25 (d, 2H); 6.91-6.94 (d, 1H); 7.26-7.29 (dd, 1H); 7.52-7.53 (d, 1H); 8.22-8.26 (t, 1H).

7-methoxy-3,4-dihydroquinoxalin-2(1H)-one (3)

Compound 2 (588 mg) was taken up in 7.5 mL of 1:1 methanol/acetic acid, treated with 10% palladium on carbon (75 mg), and stirred under an atmosphere of hydrogen overnight. The reaction mixture was filtered through celite and the filtrate was concentrated to provide 3 as a tan solid (340 mg), used without further purification.

7-methoxyquinoxalin-2(1H)-one (4)

To a solution of 8% aqueous sodium hydroxide (4.5 mL) was added 3 (340 mg) followed by a solution of 30 wt % hydrogen peroxide in water (1.97 mL). The reaction mixture was slowly heated to 80° C. and maintained at this temperature for 4 h. The mixture was cooled down to room temperature, and acetic acid (510 μL) was added dropwise. The suspension was stirred overnight at room temperature and the precipitated solid was collected by filtration to afford 4 as a tan solid (208 mg, 51% for two steps). $^1$H NMR (DMSO-d) δ: 3.83 (s, 3H); 6.76 (d, 1H); 6.89-6.93 (dd, 1H); 7.67-7.70 (d, 1H); 7.97 (s, 1H); 12.30 (brs, 1H). (See Reck, F.; et al., *J. Med. Chem.* 2011, 54, 7834.)

2-(1,3-dihydroxypropan-2-yl)isoindoline-1,3-dione (6)

Serinol (35.10 g, 38.52 mmol, 1.0 equiv) and phthalic anhydride (58.18 g, 39.28 mmol, 1.0 equiv) were suspended in anhydrous toluene (500 mL), stirred, and heated at 105° C. (internal temperature) for 24 h. The heat was then removed, and a precipitate rapidly formed when the temperature reached 80° C. After the temperature had reached 62° C., MTBE was added, and the mixture was mechanically stirred for 1 h. Vacuum filtration on a Buchner funnel afforded an off-white powder with light yellow solid clumps that were ground using a mortar and pestle. The combined solids were then suspended in MTBE and stirred for 2 h, then re-isolated by vacuum filtration and dried to afford the title compound in ca. 95% purity as an off-white powder (77.84 g, 35.19 mmol, 91%). $^1$H NMR (300 MHz, DMSO-d$_6$) δ: 7.88-7.80 (m, 4H); 4.85 (br t, J=6.0, 2H); 4.24 (dddd, J=5.7, 5.7, 8.7, 8.7, 1H); 3.80 (ddd, J=5.4, 8.8, 11.2, 2H); 3.71-3.61 (ddd, J=6.0, 6.0, 11.2, 2H).

3-(benzyloxy)propanal (8)

To a solution of 3-(benzyloxy)propan-1-ol (7, 857 mg, 5 mmol) in dichloromethane (10 mL) was added Dess-Martin periodinane (2.4 g, 5.5 mmol) at 0° C. The reaction mixture was stirred at room temperature for 3 hours. Saturated aqueous sodium thiosulfate (10 mL) and saturated aqueous sodium bicarbonate (10 mL) were added, and the mixture was stirred for 30 minutes. The reaction mixture was filtered through celite and the phases separated. The organic layer was washed twice with brine, then concentrated to give compound 8 as a colorless oil (780 mg), used without further purification.

2-(2-(2-(benzyloxy)ethyl)-trans-1,3-dioxan-5-yl)isoindoline-1,3-dione (9)

A mixture of compound 6 (110 mg, 0.5 mmol), compound 8 (83.7 mg, 0.5 mmol), p-toluenesulfonic acid (2 mg), 4 Å molecular sieve (20 mg) and toluene (4 mL) was stirred and heated at 110° C. under N$_2$ atmosphere overnight. The mixture was filtered and washed with saturated aqueous sodium bicarbonate. Phases were separated and the aqueous layer was extracted with dichloromethane. The organic layers were combined and concentrated. The crude product was purified by chromatography on silica gel with hexane/ethyl acetate (4:1) to give compound 9 as a white solid (122 mg). $^1$H NMR (CDCl$_3$) δ: 1.96-2.02 (q, 2H); 3.61 (t, 2H); 3.99-4.04 (dd, 2H); 4.41-4.48 (t, 2H); 4.55 (s, 2H); 4.58-4.71 (m, 1H); 4.85 (t, 1H); 7.28-7.36 (m, 5H); 7.74-7.77 (m, 2H); 7.83-7.87 (m, 2H).

2-(2-(2-hydroxyethyl)-trans-1,3-dioxan-5-yl)isoindoline-1,3-dione (10)

Compound 9 (183.7 mg, 0.5 mmol) was dissolved in methanol (3 mL), treated with 10% palladium on carbon (15 mg), and stirred under an atmosphere of hydrogen overnight. The reaction mixture was filtered through celite and the filtrate was concentrated to afford compound 10 as a white solid (123.4 mg). $^1$H NMR (CDCl$_3$) δ: 1.92-1.97 (q, 2H); 2.33 (brs, 1H); 3.79-3.82 (t, 2H); 4.01-4.06 (dd, 2H); 4.40-4.47 (t, 2H); 4.56-4.67 (m, 1H); 4.89 (t, 1H); 7.71-7.75 (m, 2H); 7.80-7.84 (m, 2H). $^{13}$C NMR (CDCl$_3$) δ: 167.79, 134.35, 131.54, 123.47, 101.36, 66.28, 58.53, 44.04, 36.63.

2-(5-(1,3-dioxoisoindolin-2-yl)-trans-1,3-dioxan-2-yl)ethyl methanesulfonate (11)

Compound 10 (138.7 mg, 0.5 mmol) was dissolved in pyridine (1 mL), methanesulfonic anhydride (143.7 mg, 0.8 mmol) was added at 0° C., and the mixture was stirred at room temperature for 4 hours. Ethyl acetate (10 mL, twice) and Brine (5 mL) were added, and the organic layer was combined and concentrated. Chromatography on silica gel with dichloromethane/methanol (100:1) gave 11 as a white solid (144 mg). $^1$H NMR (CDCl$_3$) δ: 2.09-2.15 (q, 2H); 3.03 (s, 3H); 4.00-4.05 (dd, 2H); 4.36-4.46 (m, 4H); 4.56-4.65 (m, 1H); 4.84 (t, 1H); 7.72-7.77 (m, 2H); 7.81-7.85 (m, 2H). $^{13}$C NMR (CDCl$_3$) δ: 167.77, 134.36, 131.54, 123.49, 98.30, 66.26, 65.65, 44.04, 37.30, 34.12. HRMS (ESI) m/z calc'd for C$_{15}$H$_{17}$NO$_7$SNa [M+Na]$^+$: 378.0623; found: 378.0608.

2-(2-(2-(7-methoxy-2-oxoquinoxalin-1(2H)-yl)ethyl)-trans-1,3-dioxan-5-yl)isoindoline-1,3-dione (12)

Referring to Scheme 1, to a solution of compound 4 (88.1 mg, 0.5 mmol) in DMSO (2 mL) was added cesium carbonate (325.8 mg, 1.0 mmol) at 0° C. After 30 minutes, compound 11 (177.7 mg, 0.5 mmol) was added and stirred overnight. The reaction mixture was treated with brine (20 mL) and extracted by dichloromethane. Then the organic layer was combined and concentrated, and the crude product was purified by chromatography on silica gel with hexane/ethyl acetate (3:1) to give compound 12 as a white solid (78.4 mg). $^1$H NMR (CDCl$_3$) δ: 2.21-2.27 (q, 2H); 3.94 (s, 3H); 4.03-4.08 (dd, 2H); 4.42-4.49 (t, 2H); 4.60-4.72 (m, 3H); 4.96 (t, 1H); 7.17 (s, 1H); 7.19-7.22 (t, 1H); 7.71-7.75 (m, 2H); 7.80-7.89 (m, 3H); 8.33 (s, 1H). $^{13}$C NMR (CDCl$_3$) δ: 167.80, 161.07, 157.70, 142.12, 136.49, 134.52, 134.29, 131.57, 129.83, 123.43, 118.58, 106.07, 99.38, 66.31, 61.93, 55.70, 44.20, 33.98.

1-(2-(5-amino-trans-1,3-dioxan-2-yl)ethyl)-7-methoxyquinoxalin-2(1H)-one (13)

A mixture of compound 12 (217.8 mg, 0.5 mmol), ethanolamine (46 μL, 7.5 mmol) and ethyl acetate (4 mL) was stirred and heated at 70° C. overnight. The solvent was removed, and the mixture was extracted with dichloromethane and washed with brine. Then the organic layer was combined and concentrated, the crude product was purified by chromatography on silica gel with dichloromethane/methanol (15:1) to give compound 13 as an oil (116 mg). $^1$H NMR (CDCl$_3$) δ: 2.14-2.20 (q, 2H); 3.03-3.10 (m, 1H); 3.25 (t, 2H); 3.92 (s, 3H); 4.10-4.14 (dd, 2H); 4.55 (t, 2H); 4.67 (t, 1H); 7.14-7.19 (m, 2H); 7.84-7.87 (d, 1H); 8.29 (s, 1H). 13C NMR (CDCl$_3$) δ: 161.09, 157.71, 142.12, 136.45, 134.48, 129.81, 118.56, 106.08, 99.06, 73.47, 62.05, 55.69, 44.19, 34.02. HRMS (ESI) m/z calc'd for C$_{15}$H$_9$N$_3$O$_4$Na [M+Na]$^+$: 328.1273; found: 328.1272.

General Reductive Amination Method

To a solution of the appropriate primary amine (0.2 mmol) in methanol (2 mL) was added the requisite aldehyde (0.2 mmol) and zinc chloride (2 mg). The mixture was stirred at room temperature for 30 minutes, then sodium cyanoborohydride (40 mg, 0.6 mmol) was added. The reaction mixture was stirred at room temperature overnight and then purified by chromatography on silica gel with dichloromethane/methanol (50:1).

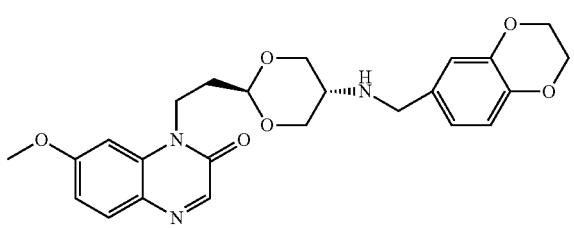 [SMILES: COc1ccc2ncc(=O)n(CC[C@H]3OC[C@H](NCc4ccc5c(c4)OCCO5)CO3)c2c1]

Example 1. [AB-0002] 1-(2-(5-(((2,3-dihydrobenzo[b][1,4]dioxin-6-yl)methyl)amino)-1,3-trans-dioxan-2-yl)ethyl)-7-methoxyquinoxalin-2(1H)-one The title compound was prepared from amine 13 and 2,3-dihydrobenzo[b][1,4]dioxine-6-carbaldehyde in 44% yield following the general method. $^1$H NMR (300 MHz, CDCl$_3$) δ: 8.29 (s, 1H); 7.86 (d, J=8.9 Hz, 1H); 7.18-7.14 (m, 2H); 6.81-6.72 (m, 3H); 4.68 (t, J=5.2 Hz, 1H); 4.55 (t, J=6.5 Hz, 2H); 4.23 (s, 4H); 4.18 (dd, J=11.3, 4.7 Hz, 2H); 3.93 (s, 3H); 3.68 (s, 2H); 3.31 (t, J=10.9 Hz, 2H); 2.99-2.94 (m, 1H); 2.16 (dd, J=11.8, 6.4 Hz, 2H). $^{13}$C NMR (75 MHz, CDCl$_3$) δ: 161.08, 157.72, 143.50, 142.74, 142.13, 136.48, 134.49, 133.50, 129.82, 120.89, 118.55, 117.24, 116.75, 106.08, 99.38, 71.62, 64.36, 62.05, 55.70, 50.78, 49.64, 34.09. HRMS (ESI) m/z calc'd for C$_{24}$H$_{28}$N$_3$O$_6$[M+H]$^+$: 454.1978; found: 454.1972.

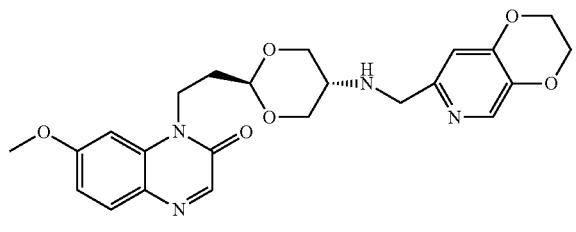 [SMILES: COc1ccc2ncc(=O)n(CC[C@H]3OC[C@H](NCc4cc5c(cn4)OCCO5)CO3)c2c1]

Example 2. [AB-0003] 1-(2-(5-(((2,3-dihydro-[1,4]dioxino[2,3-c]pyridin-7-yl)methyl)amino)-1,3-trans-dioxan-2-yl)ethyl)-7-methoxyquinoxalin-2(1H)-one The title compound was prepared from amine 13 and 2,3-dihydro-[1,4]dioxino[2,3-c]pyridine-7-carbaldehyde in 29% yield following the general method. $^1$H NMR (300 MHz, CDCl$_3$) δ: 8.29 (s, 1H); 8.09 (s, 1H); 7.86 (d, J=8.7 Hz, 1H); 7.19-7.15 (m, 2H); 6.77 (s, 1H); 4.69 (t, J=5.2 Hz, 1H); 4.55 (t, J=6.5 Hz, 2H); 4.33-4.25 (m, 4H); 4.19 (dd, J=11.3, 4.7 Hz, 2H); 3.93 (s, 3H); 3.77 (s, 2H); 3.36 (t, J=10.9 Hz, 2H); 3.00-2.91 (m, 1H); 2.16 (dd, J=11.8, 6.5 Hz, 2H). $^{13}$C NMR (75 MHz, CDCl$_3$) δ: 161.08, 157.73, 152.97, 150.22, 142.13, 140.20, 138.95, 136.49, 134.50, 129.82, 118.55, 110.61, 106.08, 99.39, 71.58, 64.97, 64.03, 62.04, 55.70, 52.06, 50.01, 34.10. HRMS (ESI) m/z calc'd for C$_{23}$H$_{26}$N$_4$O$_6$Na [M+Na]$^+$: 477.1750; found: 477.1740.

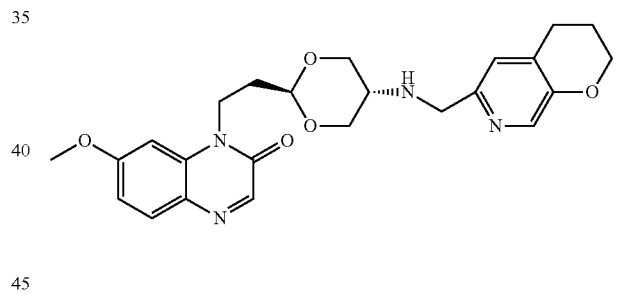

Example 3. [AB-0006] 1-(2-(5-(((3,4-dihydro-2H-pyrano[2,3-c]pyridin-6-yl)methyl)amino)-trans-1,3-dioxan-2-yl)ethyl)-7-methoxyquinoxalin-2(1H)-one The title compound was prepared from amine 13 and 3,4-dihydro-2H-pyrano[2,3-c]pyridine-6-carbaldehyde in 80% yield following the general method. $^1$H NMR (300 MHz, CDCl$_3$) δ: 8.30 (s, 1H); 8.08 (s, 1H); 7.86 (d, J=9.1 Hz, 1H); 7.20-7.15 (m, 2H); 6.92 (s, 1H); 4.70 (t, J=5.2 Hz, 1H); 4.55 (t, J=6.5 Hz, 2H); 4.24-4.18 (m, 4H); 3.93 (s, 3H); 3.79 (s, 2H); 3.38 (t, J=10.9 Hz, 2H); 3.01-2.97 (m, 1H); 2.75 (t, J=6.6 Hz, 2H); 2.16 (dd, J=11.8, 6.5 Hz, 2H); 2.07-1.96 (m, 2H). $^{13}$C NMR (75 MHz, CDCl$_3$) δ: 162.33, 161.09, 157.73, 151.05, 149.93, 142.13, 138.85, 136.50, 134.52, 131.01, 129.84, 122.59, 118.55, 106.09, 99.42, 71.51, 66.56, 62.03, 55.70, 51.92, 50.04, 34.11, 24.23, 21.64. HRMS (ESI) m/z calc'd for C$_{24}$H$_{28}$N$_4$O$_5$Na [M+Na]$^+$: 475.1957; found: 475.1953.

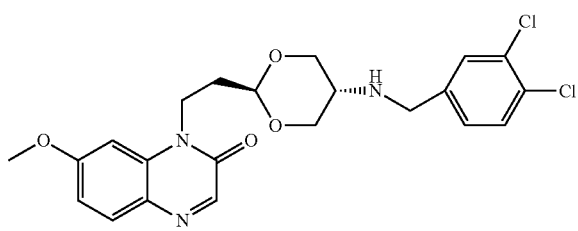 [SMILES: COc1ccc2ncc(=O)n(CC[C@H]3OC[C@H](NCc4ccc(Cl)c(Cl)c4)CO3)c2c1]

Example 4. [AB-0007] 1-(2-(5-((3,4-dichlorobenzyl)amino)-trans-1,3-dioxan-2-yl)ethyl)-7-methoxyquinoxalin-2(1H)-one The title compound was prepared from amine 13 and 3,4-dichlorobenzaldehyde in 53% yield following the general method. $^1$H NMR (300 MHz, CDCl$_3$) δ: 8.30 (s, 1H); 7.87 (d, J=8.8 Hz, 1H); 7.43-7.37 (m, 2H); 7.21-7.13 (m, 3H); 4.70 (t, J=5.2 Hz, 1H); 4.55 (t, J=6.5 Hz, 2H); 4.20 (dd, J=11.2, 4.7 Hz, 2H); 3.94 (s, 3H); 3.78 (s, 2H); 3.33 (t, J=10.8 Hz, 2H); 3.00-2.91 (m, 1H); 2.17 (dd, J=11.8, 6.4 Hz, 2H). $^{13}$C NMR (75 MHz, CDCl$_3$) δ: 161.09, 157.69, 142.11, 136.44, 134.51, 132.58, 130.41, 129.83, 127.20, 118.57, 106.07, 99.44, 71.35, 61.97, 55.70, 50.09, 49.86, 34.04. HRMS (ESI) m/z calc'd for $C_{22}H_{24}C_2N_3O_4$ [M+H]$^+$: 464.1144; found: 464.1146.

Examples AB-0009 and 0010 can be prepared from compound 20 and the requisite aldehyde according to Scheme 2.

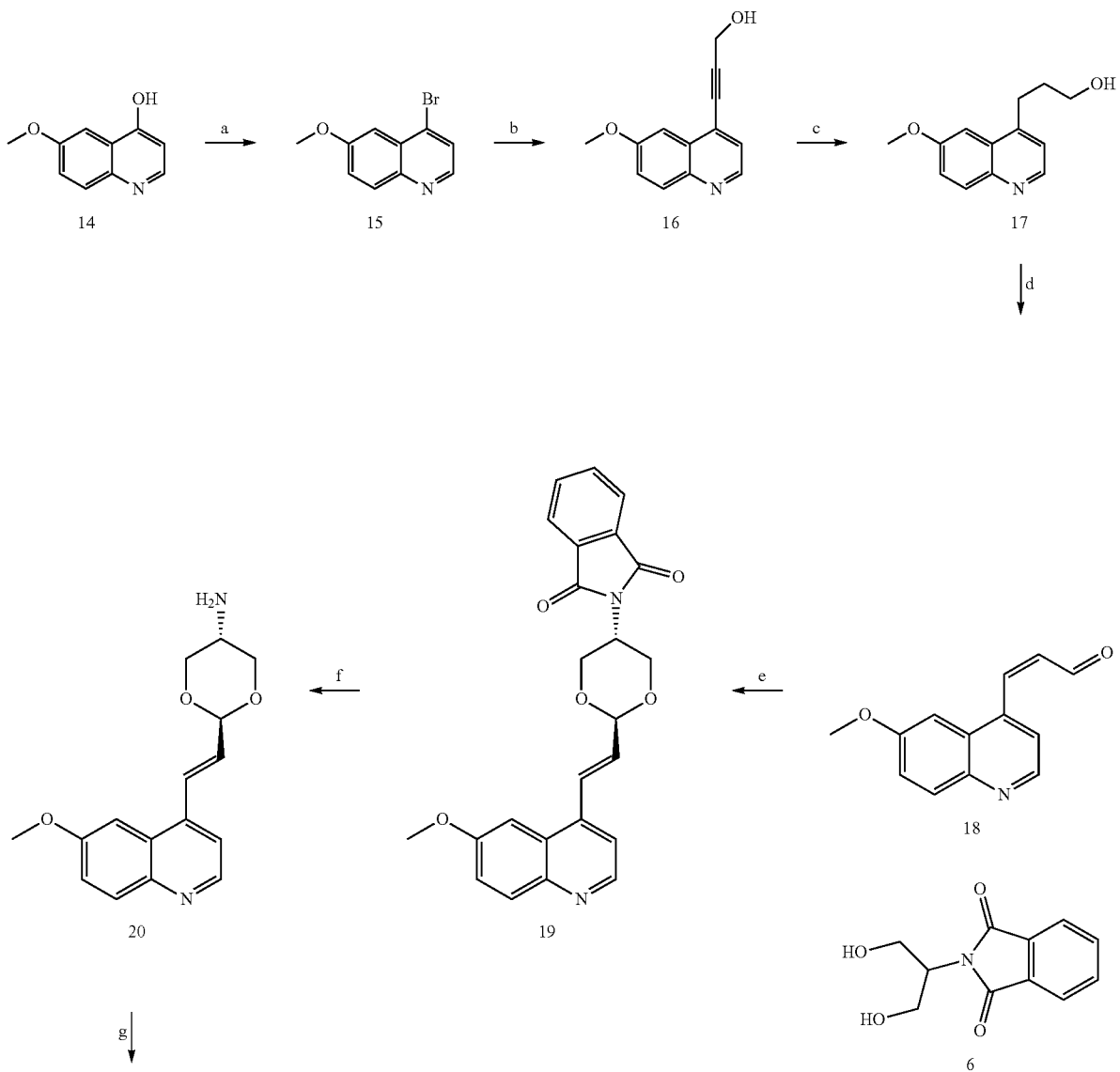

Scheme 2

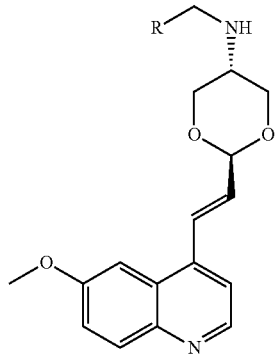

AB-0009, 0010

Reagents: (a) PBr$_3$, DMF, room temp, 93%; (b) propargyl alcohol, CuI$_2$, PdCl$_2$(PPh$_3$)$_2$, Et$_3$N, CH$_3$CN, 50° C., 76%; (c) H$_2$, Pd/C, MeOH, room temp, 95%; (d) Dess-Martin periodinane dichloromethane, room temp, 61%; (e) p-toluenesulfonic acid (cat.), toluene, 110° C., 46%; (f) ethanolamine, ethyl acetate, 70° C., (g) RCHO, ZnCl$_2$, methanol NaBH$_3$CN, room temp, overnight.

4-bromo-6-methoxyquinoline (15)

A three-necked round bottom flask vented to a 1M NaOH (aq) gas trap was charged with 14 (12.07 g, 68.90 mmol, 1.0 equiv) and anhydrous N,N-dimethylformamide (75 mL) and stirred magnetically. To the heterogeneous mixture was added PBr$_3$ (8.0 mL, 85 mmol, 1.2 equiv) drop/portionwise over several minutes by syringe. During the addition, the internal temperature rose to 75° C., and gas was evolved. A copious precipitate formed toward the end of the addition. The vent to the gas trap was 15 min after the completion of addition, and the reaction was stirred vigorously for an additional h 45 min, then quenched by pouring onto 150 g ice in 150 mL water. After brief stirring, Na$_2$CO$_3$ (20 g) was added in small portions (bubbling!), and the mixture was stirred for 15 min, whereupon the pH was approximately 7. The taupe-colored product was isolated by vacuum filtration on a Buchner funnel, washing extensively with water. After drying for several days in a vacuum desiccator, the title compound was obtained in ca. 95% purity as a light tan, powdery solid (15.58 g, 65.44 mmol, 95%). $^1$H NMR (300 MHz, DMSO-d$_6$) δ: 8.57 (d, J=4.7, 1H); 8.00 (d, J=9.2, 1H); 7.89 (d, J=4.7, 1H); 7.51 (dd, J=2.8, 9.2, 1H); 7.39 (d, J=2.8, 1H); 3.96 (s, 3H). (See WO2006/0002047, which is incorporated by reference herein in its entirety.)

3-(6-methoxyquinolin-4-yl)prop-2-yn-1-ol (16)

A mixture of compound 15 (238.1 mg, 1.0 mmol), propargyl alcohol (176 μL, 3.0 mmol), copper (II) iodide (19.1 mg, 0.1 mmol), bis(triphenylphosphine)palladium(II) dichloride (35.9 mg, 0.05 mmol), triethylamine (697 μL, 5 mmol) and acetonitrile (8 mL) was stirred and heated at 50° C. under N$_2$ atmosphere overnight. The solvent was removed, and the mixture was extracted with dichloromethane and washed with brine. The organic layers were combined and concentrated, the crude product was purified by chromatography on silica gel with hexane/ethyl acetate (1:1) to afford 16 as a solid (162 mg) solid that was used directly in the next step.

3-(6-methoxyquinolin-4-yl)propan-1-ol (17)

Compound 16 (106.6 mg, 0.5 mmol) was dissolved in methanol (3 mL), treated with 10%, palladium on carbon (15 mg), and stirred under an atmosphere of hydrogen overnight. The reaction mixture was filtered through celite, and the filtrate was concentrated and purified by chromatography on silica gel with dichloromethane/methanol (30:1) to provide 17 as a yellow solid (103.2 mg). $^1$H NMR (CDCl$_3$) δ: 1.97-2.07 (q, 2H); 2.90 (brs, 1H); 3.12 (t, 2H); 3.76 (t, 2H); 3.90 (t, 3H); 7.16-7.16 (d, 1H); 7.27-7.28 (d, 1H); 7.31-7.35 (dd, 1H); 7.97-8.00 (d, 1H); 8.59-8.60 (d, 1H).

(Z)-3-(6-methoxyquinolin-4-yl)acrylaldehyde (18)

To a solution of compound 17 (108.6 mg, 0.5 mmol) in dichloromethane (3 mL) was added Dess-Martin periodinane (240.5 mg, 0.55 mmol) at 0° C. The reaction mixture was stirred at room temperature for 4 hours. Saturated aqueous sodium thiosulfate (2 mL) and saturated aqueous sodium bicarbonate (2 mL) was added and stirred for 30 minutes. The reaction mixture was filtered through celite and the organic layer was combined and washed by brine twice. The mixture was concentrated and purified by chromatography on silica gel with dichloromethane/methanol (50:1) to afford 18 as a solid (65 mg). $^1$H NMR (CDCl$_3$) δ: 3.94 (s, 3H); 5.47-5.54 (q, 1H); 7.08-7.09 (d, 1H); 7.29-7.30 (d, 1H); 7.41-7.45 (dd, 1H); 8.02-8.09 (t, 2H); 8.79-8.80 (d, 1H); 9.75-9.78 (d, 1H).

2-(2-((E)-2-(6-methoxyquinolin-4-yl)vinyl)-trans-1, 3-dioxan-5-yl)isoindoline-1,3-dione (19)

A mixture of compound 18 (106.6 mg, 0.5 mmol), compound 6 (132.7 mg, 0.6 mmol), p-toluenesulfonic acid (2 mg), 4 Å molecular sieve (20 mg) and toluene (4 mL) was stirred and heated at 110° C. under N$_2$ atmosphere overnight. The mixture was filtered and washed with saturated aqueous sodium bicarbonate and extracted with dichloromethane. The organic layer was combined and concentrated. Then the crude product was purified by chromatography on silica gel with dichloromethane/methanol (50:1) to give 19 as a solid (95.8 mg). $^1$H NMR (CDCl$_3$) δ: 3.98 (s, 3H); 4.16-4.21 (dd, 2H); 4.58-4.66 (t, 2H); 4.71-4.82 (m, 1H); 5.41-5.42 (d, 1H); 6.39-6.46 (dd, 1H); 7.32-7.33 (d, 1H); 7.39-7.42 (dd, 1H); 7.47-7.53 (m, 2H); 7.77-7.79 (m, 2H); 7.87-7.90 (m, 2H); 8.03-8.06 (d, 1H); 8.73-8.75 (d, 1H). $^{13}$C NMR (CDCl$_3$) δ: 167.82, 157.94, 147.58, 144.66, 140.49, 134.40, 131.57, 131.45, 130.81, 128.79, 127.29, 123.51, 122.00, 118.28, 101.56, 99.71, 66.52, 55.67, 44.04. HRMS (ESI) m/z calc'd for C$_{24}$H$_{21}$N$_2$O$_5$ [M+H]$^+$: 417.1450; found: 417.1438.

2-((E)-2-(6-methoxyquinolin-4-yl)vinyl)-trans-1,3-dioxan-5-amine (20)

A mixture of compound 19 (208.2 mg, 0.5 mmol), ethanolamine (46 μL, 7.5 mmol) and ethyl acetate (4 mL) was stirred and heated at 70° C. overnight. The solvent was removed, and the mixture was extracted with dichloromethane and washed with brine. Then the organic layer was combined and concentrated, the crude product was purified by chromatography on silica gel with dichloromethane/methanol (15:1) to give 20 as an oil (111.7 mg). $^1$H NMR (CDCl$_3$) δ: 1.07 (brs, 2H); 3.13-3.23 (m, 1H); 3.37-3.44 (t, 2H); 3.95 (t, 3H); 4.23-4.28 (dd, 2H); 5.13-5.15 (d, 1H); 6.34-6.41 (dd, 1H); 7.28-7.29 (d, 1H); 7.35-7.44 (m, 3H); 7.98-8.01 (d, 1H); 8.70-8.72 (d, 1H). $^{13}$C NMR (CDCl$_3$) δ: 157.86, 147.67, 144.74, 140.49, 131.50, 131.15, 128.41, 127.27, 121.81, 118.23, 101.70, 99.40, 73.57, 55.63, 44.15. HRMS (ESI) m/z calc'd for C$_6$H$_{19}$N$_2$O$_3$[M+H]$^+$: 287.1396; found: 287.1374 [M+H]$^+$.

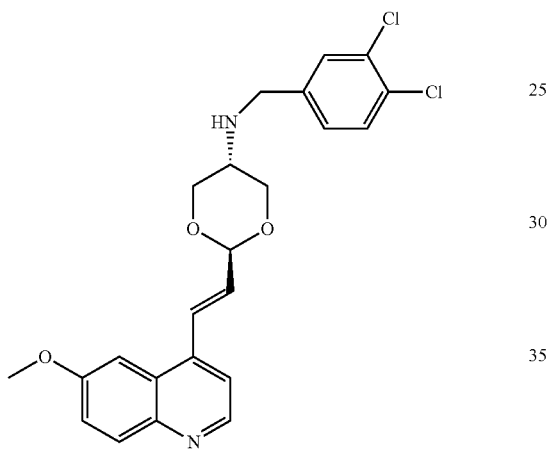

Example 5. [AB-0009] N-(3,4-dichlorobenzyl)2-((E)-2-(6-methoxyquinolin-4-yl)vinyl)-trans-1,3-dioxan-5-amine The title compound was prepared from amine 20 and 3,4-dichlorobenzaldehyde in 35% yield following the general method. $^1$H NMR (300 MHz, CDCl$_3$) δ: 8.71 (d, J=4.6 Hz, 1H); 8.01 (d, J=9.2 Hz, 1H); 7.35-7.45 (m, 5H); 7.27 (d, J=2.7 Hz, 1H); 7.16 (dd, 0.1=8.2, 2.0 Hz, 1H); 6.36 (dd, J=16.0, 4.1 Hz, 1H); 5.16 (d, J=4.1 Hz, 1H); 4.31 (dd, J=11.3, 4.7 Hz, 2H); 3.94 (s, 3H); 3.81 (s, 2H); 3.48 (t, J=10.9 Hz, 2H); 3.00-3.10 (m, 1H). $^{13}$C NMR (75 MHz, CDCl$_3$) δ: 157.89, 147.59, 144.66, 140.52, 140.40, 132.61, 131.44, 131.22, 131.11, 130.44, 129.81, 128.45, 127.27, 127.19, 121.85, 118.23, 101.70, 99.69, 71.53, 55.64, 50.20, 49.87. HRMS (ESI) m/z calc'd for C$_{23}$H$_{23}$Cl$_2$N$_2$O$_3$ [M+H]$^+$: 445.1086; found: 445.1043.

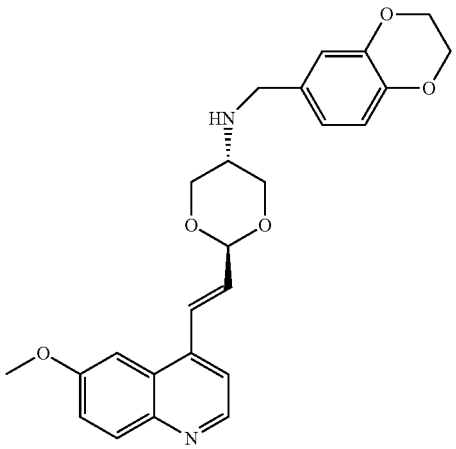 [SMILES: COc1ccc2nccc(/C=C/[C@H]3OC[C@H](NCc4ccc5c(c4)OCCO5)CO3)c2c1]

Example 6. [AB-0010] N-((2,3-dihydrobenzo[b][1,4]dioxin-6-yl)methyl)-2-((E)-2-(6-methoxyquinolin-4-yl)vinyl)-trans-1,3-dioxan-5-amine The title compound was prepared from amine 20 and 2,3-dihydrobenzo[b][1,4]dioxine-6-carbaldehyde in 73% yield following the general method. $^1$H NMR (300 MHz, CDCl$_3$) δ: 8.70 (d, J=4.6 Hz, 1H); 7.99 (d, J=9.2 Hz, 1H); 7.38-7.34 (m, 3H); 7.27 (d, J=2.7 Hz, 1H); 6.81-6.75 (m, 3H); 6.35 (dd, J=16.0, 4.1 Hz, 1H); 5.14 (d, J=4.1 Hz, 1H); 4.29 (dd, J=11.2, 4.1 Hz, 2H): 4.23 (s, 4H); 3.94 (s, 3H); 3.72 (s, 2H); 3.46 (t, J=10.8 Hz, 2H); 3.12-3.02 (m, 1H). $^{13}$C NMR (75 MHz, CDCl) δ: 157.86, 147.65, 144.72, 143.53, 142.80, 140.51, 133.36, 131.47, 131.24, 128.33, 127.27, 121.86, 120.93, 118.22, 117.29, 116.80, 101.64, 99.68, 71.70, 64.38, 64.34, 55.64, 50.82, 49.54. HRMS (ESI) m/z calc'd for C$_{25}$H$_{27}$N$_2$O [M+H]$^+$: 435.1920; found: 435.1908.

Examples AB-0011 to 0014, 0021 to 0045, 0047-0052, 0055-0058, 0069-0071, 0079-0082, 0084, and 0085 can be prepared from compound 24 and the requisite aldehyde according to Scheme 3.

Scheme 3

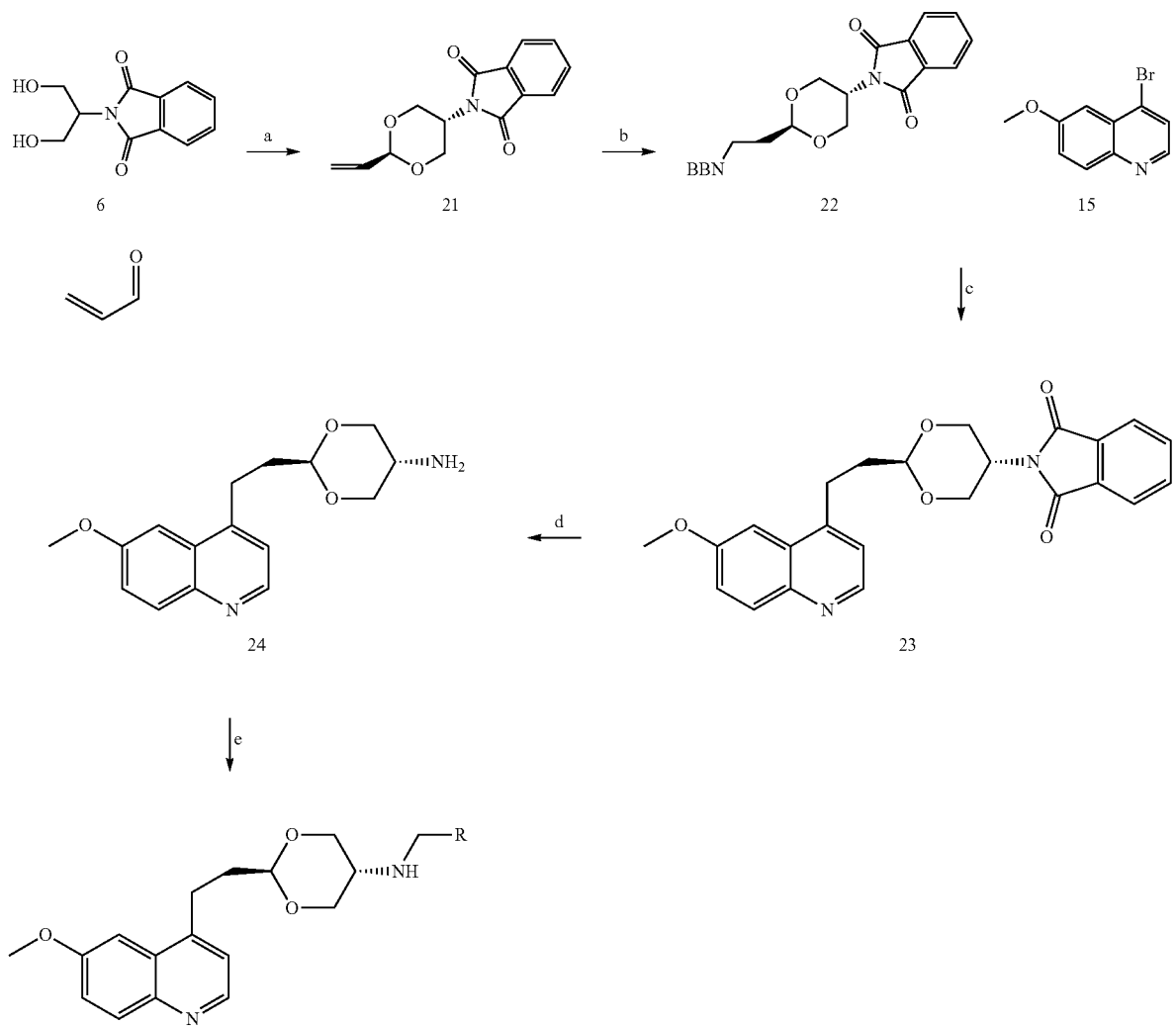

AB-0011 to 0014, 0021 to 0045, 0047-0052, 0055-0058, 0069-0071, 0079-0082, 0084, and 0085

Reagents: (a) acrolein, p-toluenesulfonic acid (cat.), CuSO4 (anhydrous), dichloromethane, room temp, 79%; (b) 9-borabicyclo[3.3.1]nonane, THF, room temp, used directly; (C) Cs2CO3, Pd/Cl2(PPh3)2, THF, room temp, 53%; (d) ethanolamine, ethyl acetate, 70° C., 78%. (e) RCHO, ZnCl₂, methanol, NaBH₃CN, room temp, overnight.

2-(2-vinyl-trans-1,3-dioxan-5-yl)isoindoline-1,3-dione (21)

A mixture of acrolein (4.16 mL, 62.3 mmol, 3.1 equiv), diol 6 (4.426 g, 20.01 mmol, 1.0 equiv), p-toluenesulfonic acid (0.12 g, 0.63 mmol, 0.03 equiv), anhydrous cupric sulfate (1.6 g, 10. mmol, 0.5 equiv) and anhydrous dichloromethane (60 mL) was stirred at room temperature under N₂ atmosphere for 36 h. The mixture was then washed with brine, and the aqueous phase was extracted with dichloromethane. The combined organic layers were concentrated, and the crude product was purified by chromatography on silica gel with dichloromethane/methanol (50:1) to give the title compound as a white solid (3.948 g. 15.23 mmol, 76%). $^1$H NMR (300 MHz, CDCl₃) δ: 7.88-7.81 (m, 2H); 7.77-7.70 (m, 2H) 5.90 (ddd, J=4.5, 10.7, 17.4, 1H); 5.53 (d apparent t, J=1.2, 17.4, 1H); 5.36 (d apparent t, J=1.1, 10.7, 1H); 5.10 (br d, J=4.5, 1H); 4.73-4.61 (m, 1H); 4.55-4.46 (m, 2H); 4.09 (dd, J=4.7, 10.6, 2H).

2-(2-(2-(6-methoxyquinolin-4-yl)ethyl)-trans-1,3-dioxan-5-yl)isoindoline-1,3-dione (23)

To a solution of alkene 21 (2.312 g, 8.918 mmol, 1.1 equiv) in THF (18 mL) was added 9-borabicyclo[3.3.1]nonane (0.5 M in THF, 16.6 mL, 8.3 mmol, 1.0 equiv) dropwise at room temperature under N₂ atmosphere. The mixture was stirred for 3 hours to form 22 and used directly in the next step.

To a mixture of 15 (1.666 g, 6.998 mmol, 1.0 equiv), cesium carbonate (5.700 g, 17.49 mmol, 2.5 equiv), bis (triphenylphosphine)palladium(II) dichloride (0.2315 g, 0.3298 mmol, 0.05 equiv) and THF (40 mL), the solution containing 22 from above was added dropwise at room temperature under N₂ atmosphere. The reaction mixture was stirred overnight. Purification by chromatography on silica gel with dichloromethane/methanol (50:1) afforded the title compound as a white solid (1.660 g, 3.8 mmol, 54%). $^1$H NMR (300 MHz, CDCl$_3$) δ: 8.69 (d, J=4.5, 1H); 8.05 (d, J=9.0, 1H); 7.89-7.81 (m, 2H); 7.78-7.71 (m, 2H); 7.38 (dd, J=2.7, 9.1, 1H); 7.34 (d, J=2.6, 1H); 7.24 (d, partially obscured by solvent, 1H); 4.78 (t, J=4.7, 1H); 4.74-4.61 (m, 1H); 4.46 (t, J=11.1, 2H); 4.08 (dd, J=4.8, 10.7, 2H); 3.97 (s, 3H); 3.24-3.16 (m, 2H), 2.19-2.10 (m, 2H).

2-(2-(6-methoxyquinolin-4-yl)ethyl)-trans-1,3-dioxan-5-amine (24)

A mixture of compound 23 (1.312 g, 3.135 mmol, 1.0 equiv), ethanolamine (2.73 mL, 45.2 mmol, 14 equiv) and ethyl acetate (40 mL) was stirred and heated at 70° C. overnight. The solvent was removed, and the mixture was dissolved in dichloromethane and washed with brine. The organic layer was combined and concentrated, and the crude product was purified by chromatography on silica gel with dichloromethane/methanol (15:1) to give the title compound as an oil (0.679 g oil, 2.35 mmol, 75%). $^1$H NMR (300 MHz, CDCl$_3$) δ: 8.65 (d, J=4.5, 1H); 7.99 (d, J=9.1, 1H); 7.35 (dd, J=2.8, 9.1, 1H); 7.30 (d, J=2.7, 1H); 7.19 (d, J=4.5, 1H); 4.44 (t, J=4.9, 1H); 4.15 (dd, J=4.5, 10.8, 2H); 3.94 (s, 3H); 3.27-3.03 (m, 5H); 2.11-2.01 (m, 2H), 1.24 (br s, 2H). $^{13}$C NMR (75 MHz, CDCl$_3$) δ: 157.8, 147.8, 146.2, 144.4, 131.7, 128.5, 121.6, 121.1, 101.9, 100.7, 73.5, 55.6, 44.3, 34.2, 26.5. HRMS (ESI) m/z calc'd for C$_{16}$H$_{21}$N$_2$O$_3$ [M+H]$^+$: 289.1552; found: 289.1551.

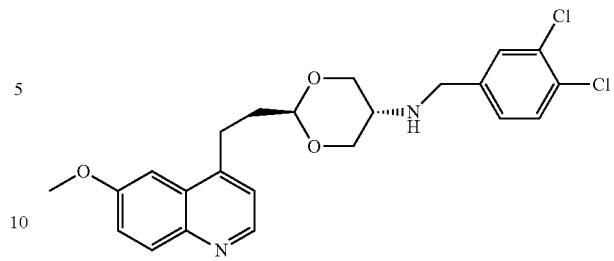

Example 8. [AB-0012] N-(3,4-dichlorobenzyl)-2-(2-(6-methoxyquinolin-4-yl)ethyl)-trans-1,3-dioxan-5-amine The title compound was prepared from amine 24 and 3,4-dichlorobenzaldehyde in 58% yield following the general method. $^1$H NMR (300 MHz, CDCl$_3$) δ: 8.66 (brs, 1H); 8.02 (d, J=9.1 Hz, 1H); 7.42-7.34 (m, 3H); 7.29 (d, J=2.4 Hz, 1H); 7.18-7.11 (m, 2H); 4.47 (t, J=4.8 Hz, 1H); 4.19 (dd, J=11.2, 4.6 Hz, 2H); 3.94 (s, 3H); 3.78 (s, 2H); 3.28 (t, J=10.9 Hz, 2H); 3.13 (t, J=8.0 Hz, 2H); 3.00-2.93 (m, 1H); 2.10-2.03 (m, 2H). $^{13}$C NMR (75 MHz, CDCl$_3$) δ: 157.71, 147.66, 146.07, 144.37, 140.54, 132.54, 131.62, 131.11, 130.40, 129.75, 128.41, 127.16, 121.40, 120.96, 101.82, 100.92, 71.46, 55.52, 50.13, 49.91, 34.12, 26.30. HRMS (ESI) m/z calc'd for C$_{23}$H$_{25}$Cl$_2$N$_2$O$_3$ [M+H]$^+$: 447.1242; found: 447.1235.

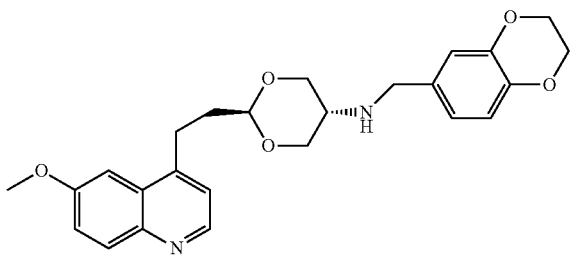 [SMILES: COc1ccc2nccc(CC[C@H]3OC[C@H](NCc4ccc5c(c4)OCCO5)CO3)c2c1]

Example 7. [AB-0011] N-((2,3-dihydrobenzo[b][1,4]dioxin-6-yl)methyl)-2-(2-(6-methoxyquinolin-4-yl)ethyl)-trans-1,3-dioxan-5-amine The title compound was prepared from amine 24 and 2,3-dihydrobenzo[b][1,4]dioxine-6-carbaldehyde in 60% yield following the general method. $^1$H NMR (300 MHz, CDCl$_3$) δ: 8.65 (d, J=4.4, 1H); 8.00 (d, J=9.1, 1H); 7.35 (dd, J=2.7, 9.1, 1H); 7.30 (d, J=2.7, 1H); 7.18 (d, J=4.4, 1H); 6.81 (d, J=8.2, 1H); 6.81 (d, J=1.8, 1H); 6.75 (dd, J=1.9, 8.2, 1H); 4.46 (t, J=4.8, 1H); 4.23 (s, 4H); 4.19 (dd, J=4.7, 11.2, 2H); 3.93 (s, 3H); 3.69 (s, 2H); 3.28 (t, J=10.8, 2H); 3.17-3.07 (m, 2H); 3.05-2.93 (m, 1H); 2.11-2.00 (m, 2H); 1.03 (br s, 1H). $^{13}$C NMR (75 MHz, CDCl$_3$) δ: 157.8, 147.8, 146.2, 144.5, 143.6, 142.9, 133.6, 131.8, 128.5, 121.5, 121.1, 121.0, 117.4, 116.9, 101.9, 101.0, 71.7, 64.49, 64.46, 55.7, 50.9, 49.8, 34.3, 26.4. HRMS (ESI) m/z calc'd for C$_{25}$H$_{29}$N$_2$O$_5$ [M+H]$^+$: 437.2076; found: 437.2039.

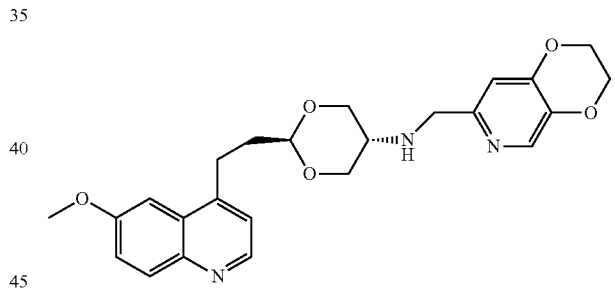

Example 9. [AB-0013] N-((2,3-dihydro-[1,4]dioxino[2,3-c]pyridin-7-yl)methyl)-2-(2-(6-methoxyquinolin-4-yl)ethyl)-trans-1,3-dioxan-5-amine The title compound was prepared from amine 24 and 2,3-dihydro-[1,4]dioxino[2,3-c]pyridine-7-carbaldehyde in 70% yield following the general method. $^1$H NMR (300 MHz, CDCl$_3$) δ: 8.63 (d, J=4.4, 1H); 8.08 (s, 1H); 7.98 (d, J=9.1, 1H); 7.33 (dd, J=2.7, 9.1, 1H); 7.28 (d, J=2.6, 1H); 7.17 (d, J=4.3, 1H); 6.77 (s, 1H); 4.47 (t, J=4.8, 1H); 4.33-4.16 (m, 6H); 3.92 (s, 3H); 3.77 (s, 2H); 3.33 (t, J=10.6, 2H); 3.15-3.06 (m, 2H); 3.04-2.90 (m, 1H); 2.11-1.98 (m, 2H); 1.95 (br s, 1H). $^{13}$C NMR (75 MHz, CDCl$_3$): 157.8, 152.9, 150.4, 147.8, 146.3, 144.4, 140.4, 139.0, 131.7, 128.5, 121.5, 121.0, 110.7, 101.9, 101.0, 71.6, 65.1, 64.1, 55.6, 52.0, 50.1, 34.3, 26.4. HRMS (ESI) m/z calc'd for C$_{24}$H$_{28}$N$_3$O$_5$ [M+H]$^+$: 438.2029; found: 438.1992.

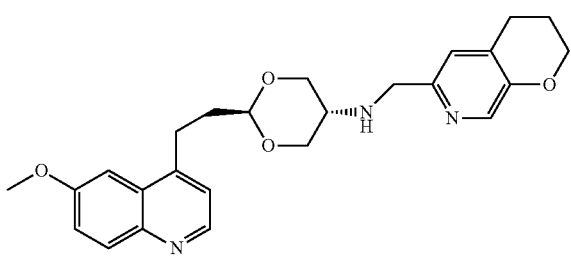 [SMILES: COc1ccc2nccc(CC[C@H]3OC[C@H](NCc4cc5c(cn4)OCCC5)CO3)c2c1]

Example 10. [AB-0014] N-((3,4-dihydro-2H-pyrano[2,3-c]pyridin-6-yl)methyl)-2-(2-(6-methoxyquinolin-4-yl)ethyl)-trans-1,3-dioxan-5-amine The title compound was prepared from amine 24 and 3,4-dihydro-2H-pyrano[2,3-c]pyridine-6-carbaldehyde in 54% yield following the general method. $^1$H NMR (300 MHz, CDCl$_3$) δ: 8.63 (d, J=4.5, 1H); 8.06 (s, 1H); 7.99 (d, J=9.2, 1H); 7.36 (dd, J=2.7, 9.2, 1H); 7.29 (d, J=2.6, 1H); 7.21 (d, J=4.5, 1H); 6.95 (s, 1H); 4.50 (t, J=4.8, 1H); 4.27-4.17 (m, 4H); 3.93 (s, 3H); 3.83 (s, 2H); 3.41 (t, J=10.8, 2H); 3.17-3.08 (m, 2H); 3.08-2.97 (m, 1H); 2.75 (t, J=6.4, 2H); 2.10-1.95 (m, 4H). $^{13}$C NMR (75 MHz, CDCl$_3$) δ: 158.0, 151.4, 148.9, 147.2 (two overlapping signals), 143.6, 138.7, 131.7, 131.0, 128.6, 123.1, 122.0, 121.1, 101.9, 101.0, 71.1, 66.7, 55.7, 51.5, 50.1, 34.1, 26.5, 24.3, 21.6. HRMS (ESI) m/z calc'd for C$_{25}$H$_{30}$N$_3$O$_4$[M+H]$^+$: 436.2236; found: 436.2210.

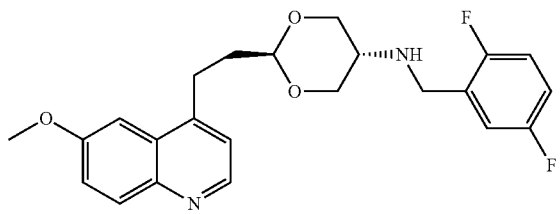 [SMILES: COc1ccc2nccc(CC[C@H]3OC[C@H](NCc4cc(F)ccc4F)CO3)c2c1]

Example 12. [AB-0022] N-(2,5-difluorobenzyl)-2-(2-(6-methoxyquinolin-4-yl)ethyl)-trans-1,3-dioxan-5-amine The title compound was prepared from amine 24 and 2,5-difluorobenzaldehyde in 56% yield following the general method. $^1$H NMR (300 MHz, CDCl$_3$) δ: 8.66 (d, J=4.5 Hz, 1H); 8.01 (d, J=9.1 Hz, 1H); 7.35 (dd, J=9.1, 2.8 Hz, 1H); 7.29 (d, J=2.8 Hz, 1H); 7.18 (d, J=4.6 Hz, 1H); 7.10-7.05 (m, 1H); 7.03-6.88 (m, 2H); 4.47 (t, J=4.8 Hz, 1H); 4.21 (dd, J=11.0, 4.8 Hz, 2H); 3.94 (s, 3H); 3.84 (s, 2H); 3.30 (t, J=10.9 Hz, 2H); 3.12 (t, J=7.9 Hz, 2H); 3.03-2.93 (m, 1H); 2.09-2.03 (m, 2H). $^{13}$C NMR (75 MHz, CDCl$_3$) δ: 160.36, 158.44, 157.72, 157.14, 155.27, 147.67, 146.10, 144.36, 131.60, 129.07, 128.98, 128.84, 128.75, 128.42, 121.42, 120.96, 116.60, 116.48, 116.45, 116.38, 116.27, 116.15, 116.13, 116.06, 115.34, 115.23, 115.02, 114.91 101.80, 100.93, 71.46, 55.53, 49.78, 44.46, 34.14, 26.32. HRMS (ESI) m/z calc'd for C$_{23}$H$_{25}$F$_2$N$_2$O$_3$[M+H]$^+$: 415.1833; found: 415.1799.

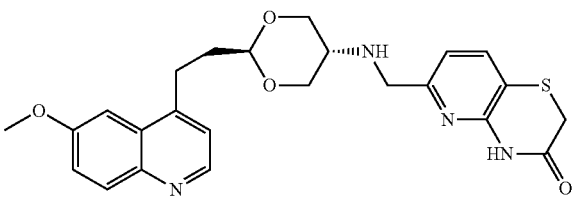

Example 11. [AB-0021] 6-(((2-(2-(6-methoxyquinolin-4-yl)ethyl)-trans-1,3-dioxan-5-yl)amino)methyl)-2H-pyrido[3,2-b][1,4]thiazin-3(4H)-one The title compound was prepared from amine 24 in and 3-oxo-3,4-dihydro-2H-pyrido[3,2-b][1,4]thiazine-6-carbaldehyde in 46% yield following the general method. $^1$H NMR (300 MHz, CDCl$_3$) δ: 8.66 (d, J=4.5, 1H); 8.57 (br s, 1H); 8.02 (d, J=9.2, 1H); 7.58 (d, J=7.8, 1H); 7.35 (dd, J=2.8, 9.2, 1H); 7.29 (d, J=2.7, 1H); 7.19 (d, J=4.5, 1H); 6.95 (d, J=7.8, 1H); 4.47 (t, J=4.9, 1H); 4.22 (dd, J=4.7, 11.2, 2H); 3.94 (s, 3H); 3.84 (s, 2H); 3.47 (s, 2H); 3.34 (t, J=10.9, 2H); 3.17-3.08 (m, 2H); 3.04-2.92 (m, 1H); 2.11-2.01 (m, 2H). $^{13}$C NMR (75 MHz, CDCl$_3$) δ: 165.7, 157.9, 156.7, 148.4, 147.8, 146.3, 144.5, 136.4, 131.7, 128.6, 121.5, 121.1, 117.9, 114.0, 102.0, 101.1, 71.6, 55.7, 51.7, 50.2, 34.3, 29.8, 26.5. HRMS (ESI) m/z calc'd for C$_{24}$H$_{27}$N$_4$O$_4$S [M+H]$^+$: 467.1753; found: 467.1727.

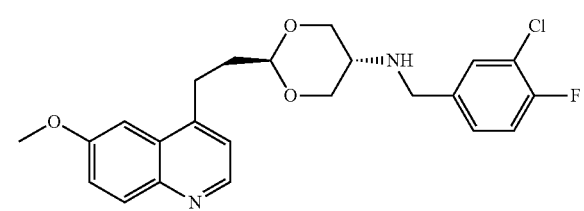 [SMILES: COc1ccc2nccc(CC[C@H]3OC[C@H](NCc4ccc(F)c(F)c4)CO3)c2c1]

Example 13. [AB-0023] N-(3-chloro-4-fluorobenzyl)-2-(2-(6-methoxyquinolin-4-yl)ethyl)-trans-1,3-dioxan-5-amine The title compound was prepared from amine 24 and 3-chloro-4-fluorobenzaldehyde in 55% yield following the general method. $^1$H NMR (300 MHz, CDCl$_3$) δ: 8.66 (d, J=4.4 Hz, 1H); 8.01 (d, J=9.1 Hz, 1H); 7.39-7.33 (m, 2H); 7.29 (d, J=2.7 Hz, 1H); 7.19-7.13 (m, 2H); 7.07 (t, J=8.6 Hz, 1H); 4.46 (t, J=4.9 Hz, 1H); 4.20 (dd, J=11.0, 4.9 Hz, 2H); 3.93 (s, 3H); 3.76 (s, 2H); 3.28 (t, J=10.9 Hz, 2H); 3.12 (t, J=7.9 Hz, 2H); 3.02-2.91 (m, 1H); 2.08-2.02 (m, 2H). $^{13}$C NMR (75 MHz, CDCl$_3$) δ: 158.93, 157.71, 155.64, 147.69, 146.06, 144.38, 137.28, 137.23, 131.62, 129.96, 128.42, 127.50, 127.41, 121.39, 121.08, 120.96, 120.84, 116.62, 116.34, 101.82, 100.93, 71.49, 55.53, 50.16, 49.88, 34.13, 26.31. HRMS (ESI) m/z calc'd for C$_{23}$H$_{25}$ClFN$_2$O$_3$ [M+H]$^+$: 431.1538; found: 431.1515.

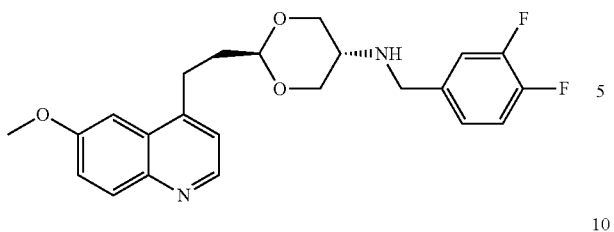
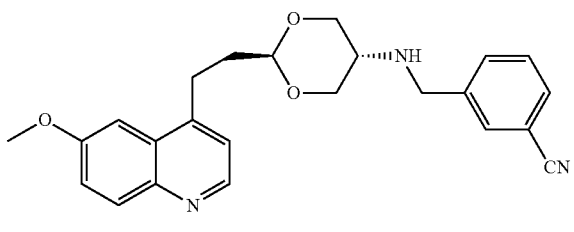 [SMILES: COc1ccc2nccc(CC[C@H]3OC[C@H](NCc4cccc(C#N)c4)CO3)c2c1]

Example 14. [AB-0024] N-(3,4-difluorobenzyl)-2-(2-(6-methoxyquinolin-4-yl)ethyl)-trans-1,3-dioxan-5-amine The title compound was prepared from amine 24 and 3,4-difluorobenzaldehyde in 44% yield following the general method. $^1$H NMR (300 MHz, CDCl$_3$) δ: 8.66 (d, J=4.5 Hz, 1H); 8.01 (d, J=9.1 Hz, 1H); 7.35 (dd, J=9.1, 2.7 Hz, 1H); 7.29 (d, J=2.6 Hz, 1H); 7.19-7.01 (m, 4H); 4.46 (t, J=4.7 Hz, 1H); 4.20 (dd, J=11.0, 4.6 Hz, 2H); 3.93 (s, 3H); 3.77 (s, 2H); 3.28 (t, J=10.9 Hz, 2H); 3.12 (t, J=7.9 Hz, 2H); 3.01-2.91 (m, 1H); 2.09-2.02 (m, 2H). $^{13}$C NMR (75 MHz, CDCl$_3$) δ: 157.72, 153.14, 152.11, 151.94, 151.25, 151.08, 148.82, 148.65, 147.97, 147.81, 147.62, 146.15, 144.29, 137.32, 137.25, 137.20, 131.54, 128.43, 123.64, 123.60, 123.56, 123.52, 121.42, 120.96, 117.24, 117.01, 116.78, 116.55, 101.82, 100.91, 71.49, 55.52, 50.27, 49.85, 34.12, 26.31. HRMS (ESI) m/z calc'd for C$_{23}$H$_{25}$F$_2$N$_2$O$_3$ [M+H]$^+$: 415.1833; found: 415.1814.

Example 16. [AB-0026] 3-(((2-(2-(6-methoxyquinolin-4-yl)ethyl)-trans-1,3-dioxan-5-yl)amino)methyl)benzonitrile The title compound was prepared from amine 24 and 3-formylbenzonitrile in 58% yield following the general method. $^1$H NMR (300 MHz, CDCl$_3$) δ: 8.66 (d, J=4.5 Hz, 1H); 8.00 (d, J=9.1 Hz, 1H); 7.65 (s, 1H); 7.56-7.53 (m, 2H); 7.45-7.40 (m, 1H); 7.35 (dd, J=9.1, 2.7 Hz, 1H); 7.29 (d, J=2.7 Hz, 1H); 7.19 (d, J=4.5 Hz, 1H); 4.47 (t, J=4.9 Hz, 1H); 4.21 (dd, J=11.1, 4.9 Hz, 2H); 3.94 (s, 3H); 3.86 (s, 2H); 3.30 (t, J=10.9 Hz, 2H); 3.12 (t, J=7.9 Hz, 2H); 3.02-2.92 (m, 1H); 2.09-2.02 (m, 2H). $^{13}$C NMR (75 MHz, CDCl$_3$) δ: 157.71, 147.67, 146.08, 144.33, 141.76, 132.29, 131.59, 131.39, 130.97, 129.27, 128.42, 121.43, 120.97, 118.80, 112.59, 101.78, 100.94, 71.45, 55.55, 50.41, 49.96, 34.10, 26.31. HRMS (ESI) m/z calc'd for C$_{24}$H$_{26}$N$_3$O$_3$ [M+H]$^+$: 404.1974; found: 404.1966.

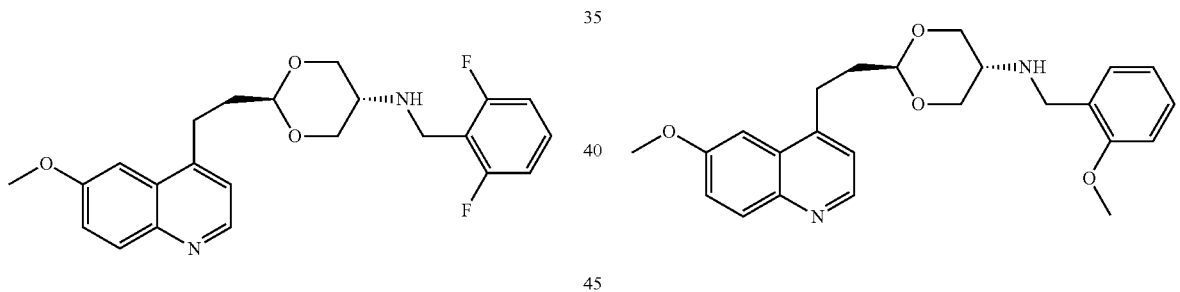

Example 15. [AB-0025] N-(2,6-difluorobenzyl)-2-(2-(6-methoxyquinolin-4-yl)ethyl)-trans-1,3-dioxan-5-amine The title compound was prepared from amine 24 and 2,6-difluorobenzaldehyde in 76% yield following the general method. $^1$H NMR (300 MHz, CDCl$_3$) δ: 8.65 (d, J=4.5 Hz, 1H); 8.01 (d, J=9.1 Hz, 1H); 7.37-7.29 (m, 2H); 7.26-7.17 (m, 2H); 6.89 (t, J=7.8 Hz, 2H); 4.46 (t, J=4.8 Hz, 1H); 4.19 (dd, J=11.0, 4.7 Hz, 2H); 3.94 (s, 3H); 3.90 (s, 2H); 3.30 (t, J=10.8 Hz, 2H); 3.12 (t, J=7.9 Hz, 2H); 3.01-2.91 (m, 1H); 2.09-2.02 (m, 2H). $^{13}$C NMR (75 MHz, CDCl$_3$) δ: 163.32, 163.20, 160.04, 159.92, 157.71, 147.68, 146.12, 144.37, 131.60, 129.35, 129.22, 129.08, 128.42, 121.43, 120.94, 116.05, 115.79, 115.53, 111.59, 111.48, 111.35, 111.25, 101.79, 100.94, 71.43, 55.52, 49.41, 38.37, 34.15, 26.35. HRMS (ESI) m/z calc'd for C$_{23}$H$_{25}$F$_2$N$_2$O$_3$ [M+H]$^+$: 415.1833; found: 415.1819.

Example 17. [AB-0027] N-(2-methoxybenzyl)-2-(2-(6-methoxyquinolin-4-yl)ethyl)-trans-1,3-dioxan-5-amine The title compound was prepared from amine 24 and 2-methoxybenzaldehyde in 77% yield following the general method. $^1$H NMR (300 MHz, CDCl$_3$) δ: 8.65 (d, J=4.4 Hz, 1H); 8.00 (d, J=9.0 Hz, 1H); 7.35 (dd, J=9.0, 2.8 Hz, 1H); 7.30 (d, J=2.8 Hz, 1H); 7.28-7.21 (m, 2H); 7.18 (d, J=4.3 Hz, 1H); 6.95-6.85 (m, 2H); 4.46 (t, J=4.9 Hz, 1H); 4.18 (dd, J=11.0, 4.8 Hz, 2H); 3.93 (s, 3H); 3.84 (s, 3H); 3.80 (s, 2H); 3.29 (t, J=10.8 Hz, 2H); 3.12 (t, J=7.8 Hz, 2H); 3.03-2.93 (m, 1H); 2.08-2.02 (m, 2H). $^{13}$C NMR (75 MHz, CDCl$_3$) δ: 157.69, 157.57, 147.72, 146.13, 144.41, 131.62, 129.74, 128.63, 128.43, 128.14, 121.41, 120.95, 120.66, 110.40, 101.80, 100.87, 71.67, 55.53, 55.26, 49.70, 47.15, 34.20, 26.34. HRMS (ESI) m/z calc'd for C$_{24}$H$_{29}$N$_2$O$_4$ [M+H]$^+$: 409.2127; found: 409.2122.

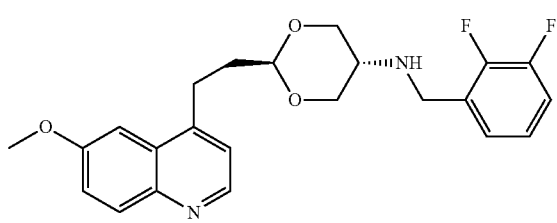 [SMILES: COc1ccc2nccc(CC[C@H]3OC[C@H](NCc4cccc(F)c4F)CO3)c2c1]

Example 18. [AB-0028] N-(2,3-difluorobenzyl)-2-(2-(6-methoxyquinolin-4-yl)ethyl)-trans-1,3-dioxan-5-amine The title compound was prepared from amine 24 and 2,3-difluorobenzaldehyde in 65% yield following the general method. $^1$H NMR (300 MHz, CDCl$_3$) δ: 8.65 (d, J=4.4 Hz, 1H); 8.01 (d, J=9.0 Hz, 1H); 7.35 (dd, J=9.0, 2.7 Hz, 1H); 7.29 (d, J=2.7 Hz, 1H); 7.18 (d, J=4.4 Hz, 1H); 7.13-7.00 (m, 3H); 4.46 (t, J=4.9 Hz, 1H); 4.20 (dd, J=11.0, 4.8 Hz, 2H); 3.94 (s, 3H); 3.88 (s, 2H); 3.30 (t, J=10.8 Hz, 2H); 3.12 (t, J=7.8 Hz, 2H); 3.03-2.93 (m, 1H); 2.09-2.02 (m, 2H). $^{13}$C NMR (75 MHz, CDCl$_3$) δ: 157.71, 152.26, 152.08, 150.70, 150.54, 148.96, 148.79, 147.68, 147.43, 146.09, 144.37, 131.61, 129.67, 129.52, 128.42, 124.70, 124.66, 124.24, 124.18, 124.09, 121.41, 120.95, 116.38, 116.16, 101.80, 100.93, 71.44, 55.52, 49.73, 44.54, 34.14, 26.32. C$_{23}$H$_{25}$F$_2$N$_2$O$_3$[M+H]$^+$: 415.1833; found: 415.1828.

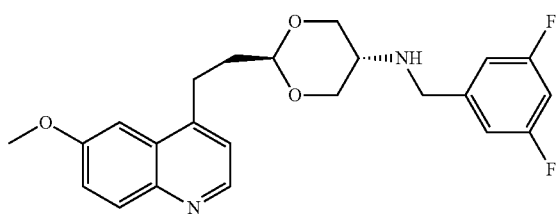 [SMILES: COc1ccc2nccc(CC[C@H]3OC[C@H](NCc4cc(F)cc(F)c4)CO3)c2c1]

Example 19. [AB-0029] N-(3,5-difluorobenzyl)-2-(2-(6-methoxyquinolin-4-yl)ethyl)-trans-1,3-dioxan-5-amine The title compound was prepared from amine 24 and 3,5-difluorobenzaldehyde in 54% yield following the general method. $^1$H NMR (300 MHz, CDCl$_3$) δ: 8.66 (d, J=4.4 Hz, 1H); 8.01 (d, J=9.1 Hz, 1H); 7.35 (dd, J=9.1, 2.7 Hz, 1H); 7.29 (d, J=2.7 Hz, 1H); 7.19 (d, J=4.4 Hz, 1H); 6.85 (d, J=7.0 Hz, 2H); 6.73-6.66 (m, 1H); 4.47 (t, J=4.8 Hz, 1H); 4.21 (dd, J=11.0, 4.7 Hz, 2H); 3.94 (s, 3H); 3.81 (s, 2H); 3.29 (t, J=10.8 Hz, 2H); 3.10 (t, J=7.9 Hz, 2H); 3.01-2.91 (m, 1H); 2.09-2.03 (m, 2H). $^{13}$C NMR (75 MHz, CDCl$_3$) δ: 164.86, 164.69, 161.57, 161.40, 157.72, 147.68, 146.08, 144.55, 144.44, 144.37, 144.33, 131.61, 128.42, 121.40, 120.96, 110.55, 110.45, 110.33, 110.22, 102.91, 102.57, 102.23, 101.81, 100.92, 71.47, 55.52, 50.47, 49.90, 34.13, 26.30. C$_{23}$H$_2$F$_2$N$_2$O$_3$ [M+H]$^+$: 415.1833; found: 415.1809.

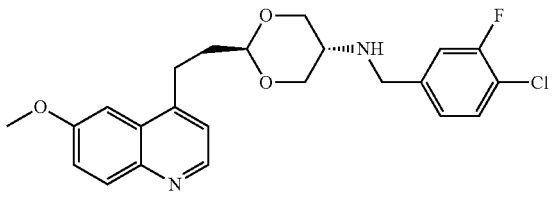

Example 20. [AB-0030] N-(4-chloro-3-fluorobenzyl)-2-(2-(6-methoxyquinolin-4-yl)ethyl)-trans-1,3-dioxan-5-amine The title compound was prepared from amine 24 and 4-chloro-3-fluorobenzaldehyde in 49% yield following the general method. $^1$H NMR (300 MHz, CDCl$_3$) δ: 8.66 (d, J=4.4 Hz, 1H); 8.01 (d, J=9.1 Hz, 1H); 7.38-7.29 (m, 3H); 7.19 (d, J=4.4 Hz, 1H); 7.14 (dd, J=9.8, 1.7 Hz, 1H); 7.03 (d, J=8.2 Hz, 1H); 4.46 (t, J=4.8 Hz, 1H); 4.20 (dd, J=11.0, 4.7 Hz, 2H); 3.94 (s, 3H); 3.79 (s, 2H); 3.29 (t, J=10.8 Hz, 2H); 3.12 (t, J=7.8 Hz, 2H); 3.02-2.91 (m, 1H); 2.09-2.03 (m, 2H). $^{13}$C NMR (75 MHz, CDCl$_3$) δ: 159.81, 157.73, 156.51, 147.65, 146.12, 144.33, 141.36, 141.28, 131.59, 130.51, 128.43, 124.06, 124.02, 121.41, 120.96, 119.66, 119.43, 116.04, 115.76, 101.83, 100.92, 71.48, 55.53, 50.28, 49.90, 34.12, 26.31. calc'd for C$_{23}$H$_{25}$ClFN$_2$O$_3$[M+H]$^+$: 431.1538; found: 431.1507.

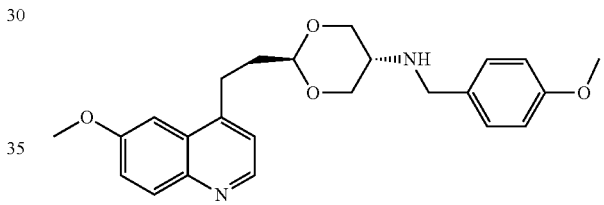

Example 21. [AB-0031] N-(4-methoxybenzyl)-2-(2-(6-methoxyquinolin-4-yl)ethyl)-trans-1,3-dioxan-5-amine The title compound was prepared from amine 24 and 4-methoxybenzaldehyde in 70% yield following the general method. $^1$H NMR (300 MHz, CDCl$_3$) δ: 8.65 (d, J=4.5 Hz, 1H); 8.00 (d, J=9.1 Hz, 1H); 7.34 (dd, J=9.1, 2.7 Hz, 1H); 7.30 (d, J=2.7 Hz, 1H); 7.22-7.17 (m, 3H); 6.85 (d, J=8.7 Hz, 2H); 4.46 (t, J=4.8 Hz, 1H); 4.19 (dd, J=10.9, 4.7 Hz, 2H); 3.94 (s, 3H); 3.79 (s, 3H); 3.74 (s, 2H); 3.28 (t, J=10.7 Hz, 2H); 3.11 (t, J=7.9 Hz, 2H); 3.05-2.94 (m, 1H); 2.08-2.01 (m, 2H). $^{13}$C NMR (75 MHz, CDCl$_3$) δ: 158.88, 157.69, 147.70, 146.11, 144.39, 132.22, 131.61, 129.14, 128.43, 121.40, 120.94, 113.95, 101.80, 100.89, 71.62, 55.51, 55.27, 50.84, 49.76, 34.17, 26.31. HRMS (ESI) m/z calc'd for C$_{24}$H$_{29}$N$_2$O$_4$ [M+H]$^+$: 409.2127; found: 409.2098.

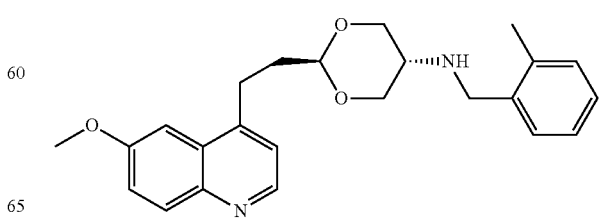

Example 22. [AB-0032] 2-(2-(6-methoxyquinolin-4-yl)ethyl)-N-(2-methylbenzyl)-trans-1,3-dioxan-5-amine The title compound was prepared from amine 24 and 2-methylbenzaldehyde in 65% yield following the general method. $^1$H NMR (300 MHz, CDCl$_3$) δ: 8.66 (d, J=4.5 Hz, 1H); 8.01 (d, J=9.1 Hz, 1H); 7.35 (dd, J=9.1, 2.7 Hz, 1H); 7.30 (d, J=2.7 Hz, 1H); 7.27-7.23 (m, 1H); 7.20-7.15 (m, 4H); 4.48 (t, J=4.8 Hz, 1H); 4.24 (dd, J=11.1, 4.7 Hz, 2H); 3.94 (s, 3H); 3.80 (s, 2H); 3.31 (t, J=10.8 Hz, 2H); 3.13 (t, J=7.9 Hz, 2H); 3.08-2.99 (m, 1H); 2.34 (s, 3H); 2.10-2.03 (m, 2H). $^{13}$C NMR (75 MHz, CDCl$_3$) δ: 157.70, 147.70, 146.14, 144.35, 137.89, 136.28, 131.59, 130.47, 127.38, 126.08, 121.45, 120.96, 101.77, 100.93, 71.62, 55.54, 50.27, 49.28, 34.15, 26.34, 18.92. HRMS (ESI) m/z calc'd for C$_{24}$H$_{29}$N$_2$O$_3$ [M+H]$^+$: 393.2178; found: 393.2148.

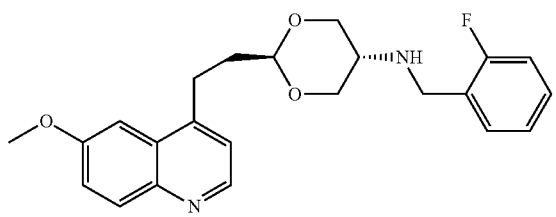 [SMILES: COc1ccc2nccc(CC[C@H]3OC[C@H](NCc4ccccc4F)CO3)c2c1]

Example 23. [AB-0033] N-(2-fluorobenzyl)-2-(2-(6-methoxyquinolin-4-yl)ethyl)-trans-1,3-dioxan-5-amine The title compound was prepared from amine 24 and 2-fluorobenzaldehyde in 70% yield following the general method. $^1$H NMR (300 MHz, CDCl$_3$) δ: 8.65 (d, J=4.5 Hz, 1H); 8.00 (d, J=9.1 Hz, 1H); 7.36-7.28 (m, 3H); 7.26-7.21 (m, 1H); 7.17 (d, J=4.4 Hz, 1H); 7.13-7.07 (m, 1H); 7.06-7.00 (m, 1H); 4.46 (t, J=4.9 Hz, 1H); 4.20 (dd, J=11.1, 4.8 Hz, 2H); 3.93 (s, 3H); 3.85 (s, 2H); 3.29 (t, J=10.8 Hz, 2H); 3.11 (t, J=7.9 Hz, 2H); 3.04-2.94 (m, 1H); 2.08-2.01 (m, 2H). $^{13}$C NMR (75 MHz, CDCl$_3$) δ: 162.76, 159.51, 157.70, 147.69, 146.10, 144.38, 131.60, 130.22, 130.16, 129.11, 129.00, 128.42, 127.13, 126.94, 124.29, 124.24, 121.41, 120.94, 115.58, 115.30, 101.80, 100.91, 71.52, 55.52, 49.71, 45.01, 44.97, 34.16, 26.32. HRMS (ESI) m/z calc'd for C$_{23}$H$_{26}$FN$_2$O$_3$ [M+H]$^+$: 397.1927; found: 397.1900.

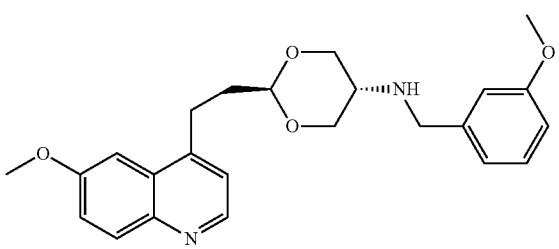

Example 24. [AB-0034] N-(3-methoxybenzyl)-2-(2-(6-methoxyquinolin-4-yl)ethyl)-trans-1,3-dioxan-5-amine The title compound was prepared from amine 24 and 3-methoxybenzaldehyde in 60% yield following the general method. $^1$H NMR (300 MHz, CDCl$_3$) δ: 8.66 (d, J=4.4 Hz, 1H); 8.01 (d, J=9.1 Hz, 1H); 7.35 (dd, J=9.1, 2.8 Hz, 1H); 7.29 (d, J=2.8 Hz, 1H); 7.24 (m, 1H); 7.19 (d, J=4.4 Hz, 1H); 6.89-6.86 (m, 2H); 6.82-6.78 (m, 1H); 4.46 (t, J=4.8 Hz, 1H); 4.21 (dd, J=11.0, 4.7 Hz, 2H); 3.93 (s, 3H); 3.80 (s, 3H); 3.79 (s, 2H); 3.30 (t, J=10.8 Hz, 2H); 3.12 (t, J=7.9 Hz, 2H); 3.06-2.96 (m, 1H); 2.09-2.02 (m, 2H). HRMS (ESI) m/z calc'd for C$_{24}$H$_{29}$N$_2$O$_4$[M+H]$^+$: 409.2127; found: 409.2092.

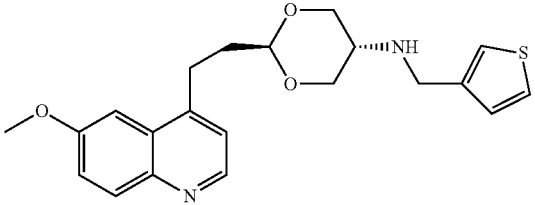 [SMILES: COc1ccc2nccc(CC[C@H]3OC[C@H](NCc4ccsc4)CO3)c2c1]

Example 25. [AB-0035] 2-(2-(6-methoxyquinolin-4-yl)ethyl)-N-(thiophen-3-ylmethyl)-trans-1,3-dioxan-5-amine The title compound was prepared from amine 24 and thiophene-3-carbaldehyde in 69% yield following the general method. $^1$H NMR (300 MHz, CDCl$_3$) δ: 8.65 (d, J=-4.4 Hz, 1H); 8.00 (d, J=9.1 Hz, 1H); 7.34 (dd, J=9.1, 2.7 Hz, 1H); 7.31-7.25 (m, 2H); 7.17 (d, J=4.4 Hz, 1H); 7.12 (d, J=1.8 Hz, 1H); 7.02 (dd, J=4.9, 1.1 Hz, 1H); 4.46 (t, J=4.9 Hz, 1H); 4.19 (dd, J=11.1, 4.7 Hz, 2H); 3.93 (s, 3H); 3.83 (s, 2H); 3.28 (t, J=10.8 Hz, 2H); 3.12 (t, J=7.9 Hz, 2H); 3.06-2.96 (m, 1H); 2.00-2.10 (m, 2H). $^{13}$C NMR (75 MHz, CDCl$_3$): 157.70, 147.71, 146.09, 144.39, 141.18, 131.62, 128.43, 127.29, 126.11, 121.71, 121.40, 120.95, 101.81, 100.91, 71.54, 55.53, 49.86, 46.43, 34.17, 26.32. HRMS (ESI) m/z calc'd for C$_{23}$H$_{24}$N$_2$O$_3$SNa [M+Na]$^+$: 407.1405; found: 407.1374.

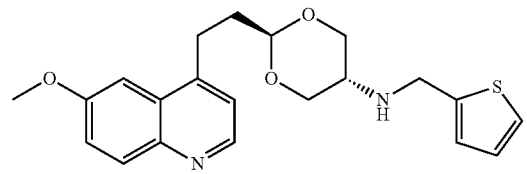 [SMILES: COc1ccc2nccc(CC[C@H]3OC[C@H](NCc4cccs4)CO3)c2c1]

Example 26. [AB-0036] 2-(2-(6-methoxyquinolin-4-yl)ethyl)-N-(thiophen-2-ylmethyl)-trans-1,3-dioxan-5-amine The title compound was prepared from amine 24 and thiophene-2-carbaldehyde in 78% yield following the general method. $^1$H NMR (CDCl$_3$, 400 MHz): δ 8.64 (d, J=4.4 Hz 1H), 8.00 (d, J=9.2 Hz 1H), 7.35 (dd, J=9.2, 2.7 Hz 1H), 7.29 (d, J=2.6 Hz 1H), 7.22 (dd, J=4.8, 1.3 Hz 1H), 7.18 (d, J=4.4, 1H), 6.93-6.95 (m, 2H), 4.46 (t, J=4.9 Hz 1H), 4.20 (dd, J=11.1, 4.7 Hz, 1H), 4.01 (s, 2H), 3.93 (s, 3H), 3.30 (t, J=10.7 Hz, 2H), 3.12 (t, J=7.8 Hz 2H), 3.04 (ddd, J=15.3, 9.8, 4.8 Hz, 1H), 2.02-2.08 (m, 2H): $^{13}$C NMR (CDCl$_3$, 100 MHz): 157.7, 147.6, 146.2, 143.8, 131.5, 128.4, 126.8, 125.1, 124.8, 121.5, 121.0, 101.8, 100.9, 71.4, 55.5, 49.5, 46.0, 34.1, 26.3; HRMS (ESI) m/z calc'd for C$_{21}$H$_{25}$N$_2$O$_3$S [M+H]$^+$: 385.1586; found: 385.1580.

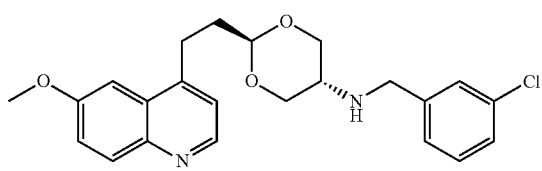 [SMILES: COc1ccc2nccc(CC[C@H]3OC[C@H](NCc4cccc(Cl)c4)CO3)c2c1]

Example 27. [AB-0037] N-(3-chlorobenzyl)-2-(2-(6-methoxyquinolin-4-yl)ethyl)-trans-1,3-dioxan-5-amine The title compound was prepared from amine 24 and 3-chlorobenzaldehyde in 68% yield following the general method. $^1$H NMR (CDCl$_3$, 400 MHz): δ 8.65 (d, J=4.5 Hz, 1H), 8.00 (d, J=9.1 Hz, 1H), 7.35 (dd, J=9.2, 2.7 1H), 7.32 (bs, 1H), 7.29 (d, J=2.7 Hz, 1H), 7.22-7.25 (m, 2H), 7.16-7.18 (m, 2H), 4.46 (t, J=4.9 Hz, 1H), 4.20 (dd, J=11.2, 4.7 Hz, 2H), 3.93 (s, 3H), 3.79 (s, 2H), 3.30 (t, J=10.7 Hz, 2H), 3.12 (t, J=7.8 Hz, 2H), 2.98 (ddd, J=15.2, 9.9, 4.8 Hz, 1H), 2.03-2.08 (m, 2H); $^{13}$C NMR (CD$_3$OD, 100 MHz): δ 159.5, 149.2, 148.1, 144.6, 143.1, 135.4, 131.1, 131.0, 129.9, 129.4, 128.4, 127.8, 123.3, 122.3, 102.9, 102.2, 71.6, 56.1, 51.1, 50.9, 35.4, 27.3; HRMS (ESI) m/z calc'd for C$_{23}$H$_{26}$ClN$_2$O$_3$: 413.1632; Found: 413.1630.

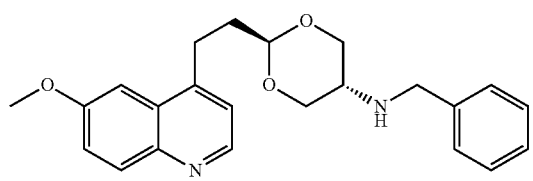 [SMILES: COc1ccc2nccc(CC[C@H]3OC[C@H](NCc4ccccc4)CO3)c2c1]

Example 28. [AB-0038] N-benzyl-2-(2-(6-methoxyquinolin-4-yl)ethyl)-trans-1,3-dioxan-5-amine The title compound was prepared from amine 24 and benzaldehyde in 55% yield following the general method. $^1$H NMR (400 MHz, CDCl$_3$) δ: 8.65 (d, J=4.5, 1H); 8.00 (d, J=9.1, 1H); 7.37-7.23 (m, 7H); 7.18 (d, J=4.4, 1H); 4.47 (t, J=4.9, 1H); 4.21 (dd, J=4.8, 11.2, 2H); 3.93 (s, 3H); 3.81 (s, 2H); 3.32 (t, J=10.9, 2H); 3.15-3.09 (m, 2H); 3.06-2.97 (m, 1H); 2.09-2.02 (m, 2H). $^{13}$C NMR (100 MHz, CDCl$_3$) δ: 157.8, 147.8, 146.3, 144.5, 140.0, 131.7, 128.7, 128.5, 128.1, 127.5, 121.6, 121.1, 101.9, 101.0, 71.6, 55.7, 51.4, 49.9, 34.3, 26.4. HRMS (ESI) m/z calc'd for C$_{23}$H$_{26}$N$_2$NaO$_3$ [M+Na]$^+$: 401.1841; found: 401.1830.

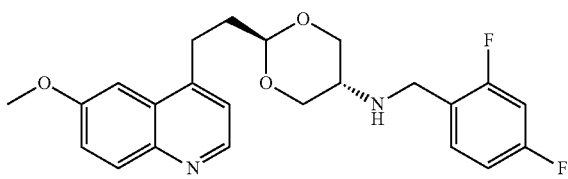

Example 29. [AB-0039] N-(2,4-difluorobenzyl)-2-(2-(6-methoxyquinolin-4-yl)ethyl)-trans-1,3-dioxan-5-amine The title compound was prepared from amine 24 and 2,4-difluorobenzaldehyde in 40% yield following the general method. $^1$H NMR (CDCl$_3$, 400 MHz): δ 8.65 (d, J=4.4 Hz, 1H), 8.01 (d, J=9.1 Hz, 1H), 7.36 (dd, J=9.2, 2.8 Hz, 1H), 7.28-7.32 (m, 2H), 7.19 (d, J=4.5 Hz, 1H), 6.77-6.87 (m, 2H), 4.46 (t, J=4.8 Hz, 1H), 4.20 (dd, J=11.2, 4.8 Hz, 2H), 3.94 (s, 3H), 3.82 (s, 2H), 3.30 (t, J=10.7 Hz, 2H), 3.12 (t, J=7.8 Hz, 2H), 2.98 (ddd, J=15.2, 9.9, 4.8 Hz, 1H), 2.03-2.08 (m, 2H); $^{13}$C NMR (CDCl$_3$, 100 MHz): δ 157.8, 147.5, 146.3, 144.2, 131.5, 131.0, 130.9, 128.4, 121.5, 121.0, 111.4, 111.2, 104.2, 103.9, 103.7, 101.8, 100.9, 71.4, 55.5, 49.7, 44.3, 34.1, 26.3; ESI-MS C$_{23}$H$_{25}$F$_2$N$_2$O$_3$ [M+H]$^+$: 415.1833; found: 415.1822.

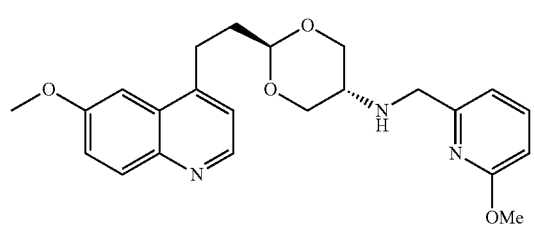 [SMILES: COc1ccc2nccc(CC[C@H]3OC[C@H](NCc4cccc(OC)n4)CO3)c2c1]

Example 30. [AB-0040] N-((6-methoxypyridin-2-yl)methyl)-2-(2-(6-methoxyquinolin-4-yl)ethyl)-trans-1,3-dioxan-5-amine The title compound was prepared from amine 24 and 6-methoxypicolinaldehyde in 64% yield following the general method. $^1$H NMR (CD$_3$OD, 400 MHz): δ 8.52 (d, J=4.6 Hz, 1H), 7.88 (d, J=10.0 Hz, 1H), 7.59 (t, J=7.4 Hz, 1H), 7.34-7.38 (m, 2H), 7.28 (d, J=4.6 Hz, 1H), 6.91 (d, J=7.2 Hz, 1H), 6.65 (d, J=8.2 Hz, 1H), 4.54 (t, J=4.8 Hz, 1H), 4.20 (dd, J=11.2, 4.8 Hz, 1H), 3.91 (s, 6H), 3.78 (s, 2H), 3.39 (t, J=10.8 Hz, 2H), 3.11 (t, J=7.9 Hz, 2H), 2.93 (ddd, J=15.4, 10.9, 4.8 Hz, 1H), 1.95-2.00 (m, 2H); $^{13}$C NMR (CDCl$_3$, 100 MHz): δ 165.4, 159.5, 158.1, 149.2, 148.2, 144.6, 140.6, 131.2, 129.9, 123.2, 122.3, 116.0, 109.9, 102.9, 102.2, 71.9, 56.1, 53.8, 52.4, 51.1, 35.4, 27.3; HRMS (ESI) m/z calc'd for C$_{23}$H$_{28}$N$_3$O$_4$: 410.2080; Found: 410.2081.

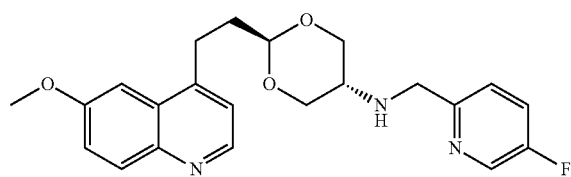 [SMILES: COc1ccc2nccc(CC[C@H]3OC[C@H](NCc4ccc(F)cn4)CO3)c2c1]

Example 31. [AB-0041] N-(4-fluorobenzyl)-2-(2-(6-methoxyquinolin-4-yl)ethyl)-trans-1,3-dioxan-5-amine The title compound was prepared from amine 24 and 4-fluorobenzaldehyde in 60% yield following the general method. $^1$H NMR (CDCl$_3$, 400 MHz): δ 8.65 (d, J=4.5 Hz, 1H), 8.00 (d, J=9.2 Hz, 1H), 7.35 (dd, J=9.2, 2.7 Hz, 1H), 7.27-7.29 (m, 3H), 7.18 (d, J=4.5 Hz, 1H), 7.00 (t, J=8.7 Hz, 2H), 4.46 (t, J=4.9 Hz, 1H), 4.20 (dd, J=11.2, 4.7 Hz, 2H), 3.93 (s, 3H), 3.78 (s, 2H); 3.30 (t, J=10.8 Hz, 2H), 3.12 (t, J=7.8 Hz, 2H), 2.99 (ddd, J=15.3, 9.8, 4.8 Hz, 1H), 2.03-2.08 (m, 2H); $^{13}$C NMR (CDCl$_3$, 100 MHz): δ 163.3, 160.9, 157.7, 147.1, 146.1, 144.3, 135.6, 131.6, 129.6, 129.5, 128.4, 121.4, 121.0, 115.5, 115.3, 101.8, 100.9, 71.4, 55.5, 50.6, 49.8, 34.1, 26.3; HRMS (ESI) m/z calc'd for $C_{23}H_{28}FN_2O_3Na$ [M+Na]$^+$: 419.1747; found: 419.1751.

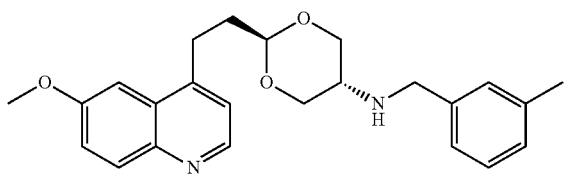

Example 32. [AB-0042] 2-(2-(6-methoxyquinolin-4-yl)ethyl)-N-(3-methylbenzyl)-trans-1,3-dioxan-5-amine The title compound was prepared from amine 24 and 3-methylbenzaldehyde in 54% yield following the general method. $^1$H NMR (CDCl$_3$, 400 MHz): δ 8.64 (d, J=4.0 Hz, 1H), 8.00 (d, J=9.1 Hz, 1H), 7.36 (dd, J=9.1, 2.7 Hz, 1H), 7.30 (d, J=2.7 Hz, 1H), 7.20-7.23 (m, 2H), 7.07-7.11 (m, 3H), 4.48 (t, J=4.8 Hz, 1H), 4.22 (dd, J=11.1, 4.7 Hz, 2H), 3.94 (s, 3H), 3.78 (s, 2H), 3.33 (t, J=10.7 Hz, 2H), 3.13 (t, J=7.8 Hz, 2H), 3.03 (ddd, J=15.2, 9.8, 4.7 Hz, 1H), 2.03-2.08 (m, 2H); $^{13}$C NMR (CDCl$_3$, 100 MHz): δ 157.8, 147.3, 146.7, 143.9, 139.6, 138.3, 131.2, 128.8, 128.5, 128.1, 125.1, 121.7, 121.0, 101.8, 100.9, 71.4, 55.6, 51.3, 49.8, 34.1, 26.4, 21.4; HRMS (ESI) m/z calc'd for $C_{24}H_{29}N_2O_3$ [M+H]$^+$: 393.2178; found: 393.2178.

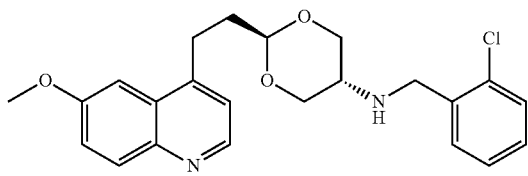 [SMILES: COc1ccc2nccc(CC[C@H]3OC[C@H](NCc4ccccc4Cl)CO3)c2c1]

Example 33. [AB-0043] N-(2-chlorobenzyl)-2-(2-(6-methoxyquinolin-4-yl)ethyl)-trans-1,3-dioxan-5-amine The title compound was prepared from amine 24 and 2-chlorobenzaldehyde in 55% yield following the general method. $^1$H NMR (CDCl$_3$, 400 MHz): δ 8.65 (d, J=4.5 Hz, 1H), 8.01 (d, J=9.2 Hz, 1H), 7.36-7.38 (m, 2H), 7.33-7.35 (m, 1H), 7.29 (d, J=2.7 Hz, 1H), 7.21-7.25 (m, 2H), 7.19 (d, J=4.4 Hz, 1H), 4.47 (t, J=4.9 Hz, 1H), 4.20 (dd, J=11.3, 4.8 Hz, 2H), 3.93 (s, 3H), 3.90 (s, 2H), 3.32 (t, J=10.7 Hz, 2H), 3.12 (t, J=7.8 Hz, 2H), 3.00 (ddd, J=15.2, 9.9, 4.8 Hz, 1H), 2.03-2.08 (m, 2H); $^{13}$C NMR (CDCl$_3$, 100 MHz): δ 157.8, 147.5, 146.3, 144.2, 137.3, 133.7, 131.5, 130.2, 129.7, 128.8, 128.4, 127.1, 121.5, 121.0, 101.79, 100.9, 71.5, 55.5, 49.8, 49.0, 34.1, 26.4; HRMS (ESI) m/z calc'd for $C_{23}H_{26}ClN_2O_3$: 413.1632; Found: 413.1634.

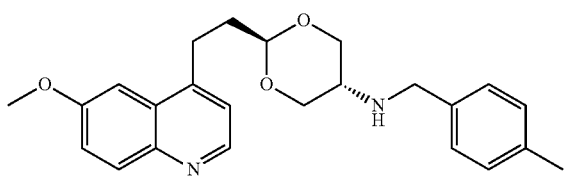

Example 34. [AB-0044] 2-(2-(6-methoxyquinolin-4-yl)ethyl)-N-(4-methylbenzyl-trans-1,3-dioxan-5-amine The title compound was prepared from amine 24 and 4-methylbenzaldehyde in 78% yield following the general method. $^1$H NMR (CDCl$_3$, 400 MHz): δ 8.65 (d, J=4.4 Hz, 1H), 8.00 (d, J=9.1 Hz, 1H), 7.35 (dd, J=9.2, 2.8 Hz, 1H), 7.29 (d, J=2.7 Hz, 1H), 7.12-7.20 (m, 5H), 4.47 (t, J=4.9 Hz, 1H), 4.20 (dd, J=11.2, 4.7 Hz, 2H), 3.93 (s, 3H), 3.77 (s, 2H), 3.30 (t, J=10.8 Hz, 2H), 3.11 (t, J=7.7 Hz, 2H), 3.01 (ddd, J=15.3, 9.9, 4.8 Hz, 1H), 2.33 (s, 3H), 2.03-2.08 (m, 2H); $^{13}$C NMR (CDCl$_3$, 100 MHz): δ 157.7, 147.7, 146.2, 144.4, 137.0, 136.9, 131.6, 129.3, 128.4, 128.0, 121.4, 121.0, 101.8, 100.9, 71.5, 55.5, 51.1, 49.7, 34.2, 26.3, 21.1; HRMS (ESI) m/z calc'd for $C_{24}H_{29}N_2O_3$ [M+H]$^+$: 393.2178; found: 393.2174.

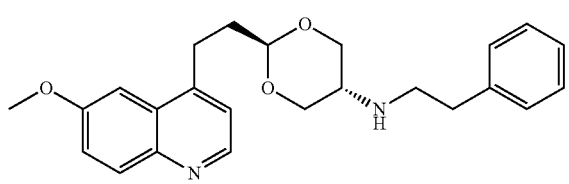 [SMILES: COc1ccc2nccc(CC[C@H]3OC[C@H](NCCc4ccccc4)CO3)c2c1]

Example 35. [AB-0045] 2-(2-(6-methoxyquinolin-4-yl)ethyl)-N-phenethyl-trans-1,3-dioxan-5-amine The title compound was prepared from amine 24 and 2-phenylethanal in 65% yield following the general method. $^1$H NMR (CDCl$_3$, 400 MHz): δ 8.65 (d, J=4.5 Hz 1H), 8.00 (d, J=9.1 Hz 1H), 7.35 (dd, J=9.1, 2.7, 1H), 7.28-7.32 (m, 3H), 7.21-7.24 (m, 1H), 7.14-7.20 (m, 3H), 4.45 (t, J=4.9 Hz 1H), 4.21 (dd, J=11.3, 4.8 Hz, 2H), 3.94 (s, 3H), 3.27 (t, J=10.7 Hz, 2H), 3.12 (t, J=7.8 Hz, 2H), 2.99 (ddd, J=15.2, 9.8, 4.7 Hz, 1H), 2.92 (t, J=7.4 Hz, 2H), 2.78 (t, J=7.0 Hz, 2H), 2.03-2.08 (m, 2H); $^{13}$C NMR (CDCl$_3$, 100 MHz): 157.7, 147.7, 146.1, 144.3, 139.3, 131.6, 128.7, 128.6, 128.4, 126.4, 121.4, 121.0, 101.8, 100.9, 71.4, 55.5, 50.2, 48.4, 36.6, 34.2, 26.3; HRMS (ESI) m/z calc'd for $C_{24}H_{29}N_2O_3$: 393.2178; Found: 393.2173.

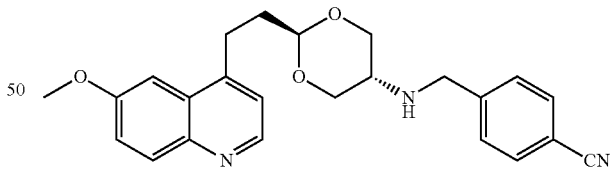

Example 36. [AB-0047] 4-(((2-(2-(6-methoxyquinolin-4-yl)ethyl)-trans-1,3-dioxan-5-yl)amino)methyl)benzonitrile The title compound was prepared from amine 24 and 4-formylbenzonitrile in 62% yield following the general method. $^1$H NMR (CDCl$_3$, 400 MHz): δ 8.64 (d, J=4.5 Hz, 1H), 8.00 (d, J=9.2 Hz, 1H), 7.60 (d, J=8.3 Hz, 2H), 7.43 (d, J=8.3 Hz, 1H), 7.35 (dd, J=9.2, 2.8 Hz, 1H), 7.28 (d, J=2.7 Hz, 1H), 4.46 (t, J=4.9 Hz, 1H), 4.20 (dd, J=11.2, 4.7 Hz, 2H), 3.93 (s, 3H), 3.87 (s, 2H), 3.47 (s, 1H), 3.29 (t, J=10.6 Hz, 2H), 3.11 (t, J=7.8 Hz, 2H), 2.96 (ddd, J=15.2, 9.8, 4.8

Hz, 1H), 2.02-2.08 (m, 2H); $^{13}$C NMR (CDCl$_3$, 100 MHz): δ 157.7, 147.5, 146.3, 145.8, 144.2, 132.3, 131.5, 128.4, 121.5, 121.0, 118.8, 101.8, 100.9, 71.4, 55.5, 50.8, 50.0, 34.1, 26.3; HRMS (ESI) m/z calc'd for C$_{24}$H$_{26}$N$_3$O$_3$ [M+H]$^+$: 404.1974; found: 404.1973.

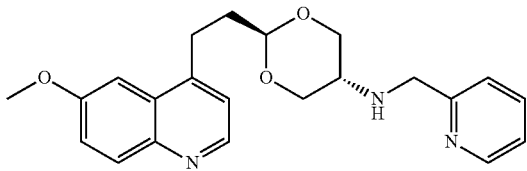

Example 37. [AB-0048] (2-(2-(6-methoxyquinolin-4-yl)ethyl)-N-(pyridin-2-ylmethyl)-trans-1,3-dioxan-5-amine The title compound was prepared from amine 24 and picolinaldehyde in 59% yield following the general method. $^1$H NMR (400 MHz, CD$_3$OD) δ: 8.53 (d, J=4.5, 1H); 8.49 (br d, J=4.4, 1H); 7.92-7.86 (m, 1H); 7.80 (td, J=1.7, 7.7, 1H); 7.47 (br d, J=7.8, 1H); 7.40-7.35 (m, 2H); 7.33-7.27 (m, 2H); 4.54 (t, J=4.8, 1H); 4.20 (dd, J=4.8, 11.3, 2H); 3.92 (s, 3H); 3.90 (s, 2H); 3.39 (t, J=10.9, 2H); 3.16-3.09 (m, 2H); 2.96-2.87 (m, 1H); 2.03-1.94 (m, 2H). $^{13}$C NMR (100 MHz, CD$_3$OD) δ: 160.6, 159.5, 149.8, 149.2, 148.2, 144.7, 138.7, 131.2, 129.9, 124.0, 123.8, 123.3, 122.3, 102.9, 102.2, 71.9, 56.1, 52.7, 51.2, 35.4, 27.3. HRMS (ESI) m/z calc'd for C$_{22}$H$_{26}$N$_3$O$_3$ [M+H]$^+$: 380.1974; found: 380.1962.

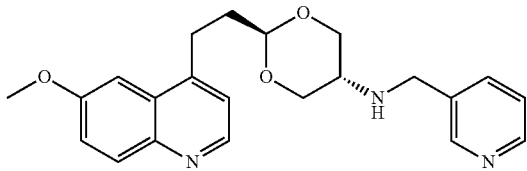 [SMILES: COc1ccc2nccc(CC[C@H]3OC[C@H](NCc4cccnc4)CO3)c2c1]

Example 38. [AB-0049] 2-(2-(6-methoxyquinolin-4-yl)ethyl)-N-(pyridin-3-ylmethyl)-trans-1,3-dioxan-5-amine The title compound was prepared from amine 24 and nicotinaldehyde in 73% yield following the general method. $^1$H NMR (400 MHz, CD$_3$OD) δ: 8.55-8.51 (m, 2H); 8.43 (dd, J=1.6, 4.9, 1H); 7.92-7.86 (m, 1H); 7.84 (dt, J=1.9, 7.9, 1H); 7.43-7.35 (m, 3H); 7.30 (d, J=4.6, 1H); 4.54 (t, J=4.8, 1H); 4.21 (dd, J=4.8, 11.3, 2H); 3.93 (s, 3H); 3.83 (s, 2H); 3.38 (t, J=10.7, 2H); 3.17-3.10 (m, 2H); 2.94-2.86 (m, 1H); 2.03-1.96 (m, 2H). $^{13}$C NMR (100 MHz, CD$_3$OD) δ: 159.5, 150.1, 149.2, 148.8, 148.2, 144.7, 138.2, 137.8, 131.2, 129.9, 125.2, 123.3, 122.4, 102.9, 102.2, 72.0, 56.1, 51.1, 49.0, 35.5, 27.3. HRMS (ESI) m/z calc'd for C$_{22}$H$_{25}$N$_3$NaO$_3$ [M+Na]$^+$: 402.1794; found: 402.1788.

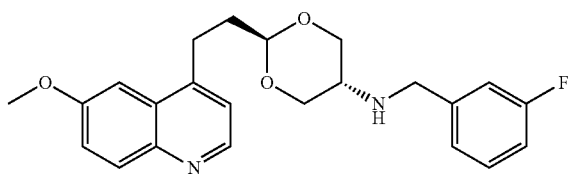 [SMILES: COc1ccc2nccc(CC[C@H]3OC[C@H](NCc4cccc(F)c4)CO3)c2c1]

Example 39. [AB-0050] N-(3-fluorobenzyl)-2-(2-(6-methoxyquinolin-4-yl)ethyl)-trans-1,3-dioxan-5-amine The title compound was prepared from amine 24 and 3-fluorobenzaldehyde in 66% yield following the general method. $^1$H NMR (CDCl$_3$, 400 MHz): δ 8.63 (d, J=4.5 Hz, 1H), 8.01 (d, J=9.2 Hz, 1H), 7.36 (dd, J=9.2, 2.7 Hz, 1H), 7.27-7.33 (m, 3H), 7.19 (d, J=4.5 Hz, 1H), 7.04-7.13 (m, 3H), 6.95 (td, J=8.7, 2.5 Hz, 1H), 4.71 (s, 1H), 4.48 (t, J=4.9 Hz, 1H), 4.22 (dd, J=11.2, 4.8 Hz, 2H), 3.94 (s, 3H), 3.82 (s, 2H), 3.31 (t, J=10.6 Hz, 2H), 3.13 (t, J=7.8 Hz, 2H), 3.00 (ddd, J=15.3, 9.9, 4.8 Hz, 1H), 2.04-2.09 (m, 2H); $^{13}$C NMR (CDCl$_3$, 100 MHz): δ 164.3, 161.8, 157.7, 147.6, 146.2, 131.5, 130.0, 130.0, 128.4, 123.4, 122.2, 121.5, 121.0, 114.8, 114.6, 101.8, 100.9, 71.5, 55.5, 50.8, 49.9, 34.1, 26.3; HRMS (ESI) m/z calc'd for C$_{23}$H$_{25}$FN$_2$O$_3$Na [M+Na]$^+$: 419.1747; found: 419.1752.

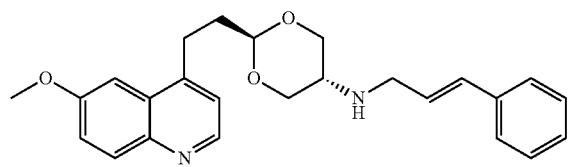 [SMILES: COc1ccc2nccc(CC[C@H]3OC[C@H](NC/C=C/c4ccccc4)CO3)c2c1]

Example 40. [AB-0051] N-cinnamyl-2-(2-(6-methoxyquinolin-4-yl)-trans-1,3-dioxan-5-amine The title compound was prepared from amine 24 and cinnamaldehyde in 58% yield (as a 4:1 mixture of desired product with undesired product containing reduced olefin) following the general method. $^1$H NMR (CD$_3$OD, 400 MHz): δ 8.52 (d, J=4.5 Hz 1H), 7.89 (d, J=10.0 Hz 1H), 7.34-7.39 (m, 4H), 7.26-7.30 (m, 3H), 7.16-7.25 (m, 2H), 6.56 (d, J=15.9 Hz, 1H), 6.24 (dt, J=15.9, 6.6 Hz, 1H), 4.54 (t, J=4.8 Hz, 1H), 4.25 (dd, J=11.2, 4.7 Hz, 2H), 3.90 (s, 3H), 3.35-3.40 (m, 4H), 3.12 (t, J=7.9 Hz, 2H), 2.95 (ddd, J=15.4, 10.3, 4.9 Hz, 1H), 1.96-2.01 (m, 2H); $^{13}$C NMR (CD$_3$OD, 100 MHz): 159.5, 149.2, 148.2, 144.6, 138.3, 133.5, 131.2, 129.9, 129.6, 129.4, 128.6, 128.3, 127.4, 126.9, 123.3, 122.3, 102.9, 102.2, 71.8, 56.1, 49.8, 35.4, 27.3; HRMS (ESI) m/z calc'd for C$_{25}$H$_{29}$N$_2$O$_3$: 405.2178; Found: 405.2179.

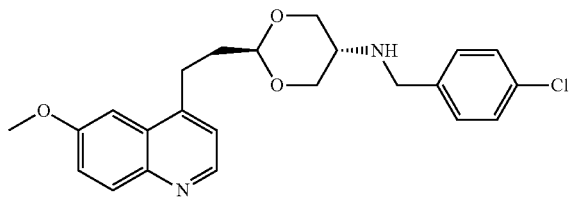

Example 41. [AB-0052] N-(4-chlorobenzyl)-2-(2-(6-methoxyquinolin-4-yl)ethyl)-trans-1,3-dioxan-5-amine The title compound was prepared from amine 24 and 4-chlorobenzaldehyde in 82% yield following the general method. $^1$H NMR (CD$_3$OD, 400 MHz): δ 8.52 (d, J=4.6 Hz 1H), 7.88 (d, J=10.0 Hz 1H), 7.31 (s, 4H), 7.28 (d, J=4.6 Hz 1H), 4.52 (t, J=4.8 Hz, 1H), 4.17 (dd, J=11.2, 4.8 Hz, 2H), 3.91 (s, 3H), 3.74 (s, 2H), 3.36 (t, J=10.8 Hz 2H), 3.11 (t, J=7.9 Hz 2H), 2.88 (ddd, J=15.4, 10.2, 4.8 Hz, 1H), 1.95-2.00 (m, 2H); $^{13}$C NMR (CD$_3$OD, 100 MHz): 159.5, 149.2, 148.1, 144.6, 139.9, 134.0, 131.1, 130.9, 129.9, 129.5, 123.3, 122.2, 102.2, 71.9, 56.1, 51.0, 50.9, 35.4, 27.3; HRMS (ESI) m/z, calc'd for C$_{23}$H$_{26}$ClN$_2$O$_3$: 413.1632; Found: 413.1635.

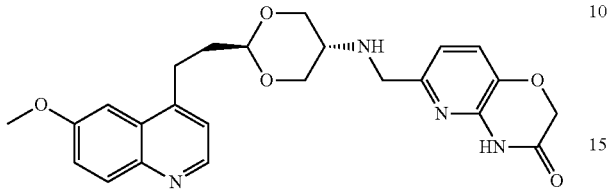

Example 42. [AB-0055] 6-(((2-(2-(6-methoxyquinolin-4-yl)ethyl)-trans-1,3-dioxan-5-yl)amino)methyl)-2H-pyrido[3,2-b][1,4]oxazin-3(4H)-one The title compound was prepared from amine 24 and 3-oxo-3,4-dihydro-2H-pyrido[3,2-b][1,4]oxazine-6-carbaldehyde in 35% yield following the general method. $^1$H NMR (300 MHz, CDCl$_3$) δ: 8.66 (d, J=4.4, 1H); 8.64 (br s, 1H); 8.02 (d, J=9.2, 1H); 7.36 (dd, J=2.7, 9.1, 1H); 7.34 (d, J=2.7, 1H); 7.22 (d, J=8.1, 1H); 7.19 (d, J=4.6, 1H); 6.92 (d, J=8.1, 1H); 4.65 (s, 2H); 4.47 (t, J=4.9, 1H); 4.22 (dd, J=4.7, 11.2, 2H); 3.94 (s, 3H); 3.82 (s, 2H); 3.34 (t, J=10.9, 2H); 3.17-3.08 (m, 2H); 3.06-2.91 (m, 1H); 2.12-2.01 (m, 2H). $^{13}$C NMR (75 MHz, CDCl$_3$) δ: 165.4, 157.9, 151.6, 147.8, 146.3, 144.5, 140.3, 138.5, 131.7, 128.6, 124.4, 121.5, 121.1, 118.2, 102.0, 101.1, 71.6, 67.4, 55.7, 51.5, 50.2, 34.3, 26.5. HRMS (ESI) m/z calc'd for C$_{24}$H$_{27}$N$_4$O$_5$ [M+H]$^+$: 451.1981; found: 451.1970.

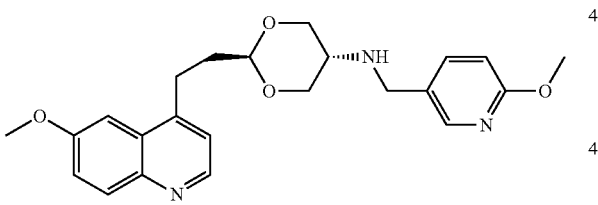

Example 43. [AB-0056] N-((6-methoxypyridin-3-yl)methyl)-2-(2-(6-methoxyquinolin-4-yl)ethyl)-trans-1,3-dioxan-5-amine The title compound was prepared from amine 24 and 6-methoxynicotinaldehyde in 65% yield following the general method. $^1$H NMR (300 MHz, CDCl$_3$) δ: 8.65 (d, J=4.4 Hz, 1H); 8.06 (d, J=2.2 Hz, 1H); 8.00 (d, J=9.0 Hz, 1H); 7.54 (dd, J=8.6, 2.4 Hz, 1H); 7.35 (dd, J=9.1, 2.7 Hz, 1H); 7.29 (d, J=2.7 Hz, 1H); 7.19 (t, J=4.5 Hz, 1H); 6.71 (d, J=8.4 Hz, 1H); 4.45 (t, J=4.8 Hz, 1H); 4.20 (dd, J=11.1, 4.7 Hz, 2H); 3.93 (s, 3H); 3.92 (s, 3H); 3.73 (s, 2H); 3.28 (t, J=10.8 Hz, 2H); 3.11 (t, J=7.8 Hz, 2H); 3.03-2.93 (m, 1H); 2.09-2.02 (m, 2H). $^{13}$C NMR (75 MHz, CDCl$_3$) δ: 163.70, 157.70, 147.70, 146.07, 144.39, 138.75, 131.62, 128.41, 128.14, 121.39, 120.95, 110.85, 101.80, 100.91, 71.52, 55.53, 53.42, 49.71, 48.14, 34.14, 26.30. HRMS (ESI) m/z calc'd for C$_{23}$H$_{28}$N$_3$O$_4$: 410.2080; Found: 410.2067.

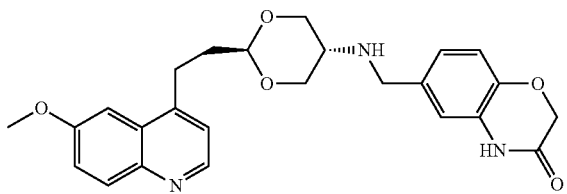 [SMILES: COc1ccc2nccc(CC[C@H]3OC[C@H](NCc4ccc5c(c4)NC(=O)CO5)CO3)c2c1]

Example 44. [AB-0057] 6-(((2-(2-(6-methoxyquinolin-4-yl)ethyl)-trans-1,3-dioxan-5-yl)amino)methyl)-2H-benzo[b][1,4]oxazin-3(4H)-one The title compound was prepared from amine 24 and 3-oxo-3,4-dihydro-2H-benzo[b][1,4]oxazine-6-carbaldehyde in 71% yield following the general method. $^1$H NMR (300 MHz, CDCl$_3$) δ: 9.16 (br s, 1H); 8.66 (d, J=4.5, 1H); 8.01 (d, J=9.2, 1H); 7.35 (dd, J=2.7, 9.2, 1H); 7.29 (d, J=2.6, 1H); 7.19 (d, J=4.5, 1H); 6.95-6.86 (m, 2H); 6.80 (br s, 1H), 4.61 (s, 2H); 4.46 (t, J=4.8, 1H); 4.19 (dd, J=4.6, 11.0, 2H); 3.93 (s, 3H); 3.72 (s, 2H); 3.28 (t, J=10.8, 2H); 3.17-3.07 (m, 2H); 3.04-2.91 (m, 1H); 2.11-2.00 (m, 2H). $^{13}$C NMR (75 MHz, CDCl$_3$) δ: 166.3, 157.8, 147.8, 146.2, 144.5, 143.0, 135.1, 131.7, 128.6, 126.3, 123.8, 121.5, 121.1, 116.9, 115.7, 102.0, 101.1, 71.7, 67.4, 55.7, 50.7, 49.9, 34.3, 26.5. HRMS (ESI) m/z calc'd for C$_{25}$H$_{28}$N$_3$O$_5$ [M+H]$^+$: 450.2029; found: 450.2004.

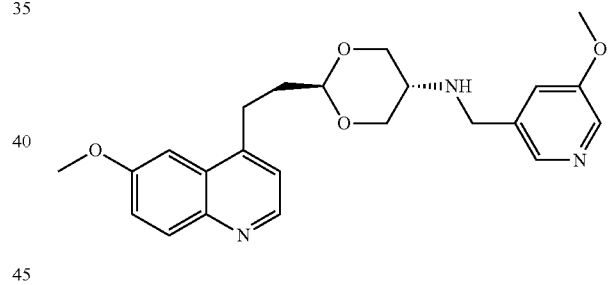

Example 45. [AB-0058] N-((6-methoxypyridin-3-yl)methyl)-2-(2-(6-methoxyquinolin-4-yl)ethyl)-trans-1,3-dioxan-5-amine The title compound was prepared from amine 24 and 5-methoxynicotinaldehyde in 59% yield following the general method. $^1$H NMR (300 MHz, CDCl$_3$) δ: 8.66 (d, J=4.4 Hz, 1H); 8.19 (d, J=18.3 Hz, 2H); 8.01 (d, J=9.2 Hz, 1H); 7.36 (dd, J=9.1, 2.7 Hz, 1H); 7.29 (d, J=2.7 Hz, 1H); 7.19 (t, J=4.3 Hz, 2H); 4.47 (t, J=4.9 Hz, 1H); 4.23 (dd, J=1.2, 4.7 Hz, 2H); 3.94 (s, 3H); 3.86 (s, 3H); 3.83 (s, 2H); 3.30 (t, J=10.8 Hz, 2H); 3.15 (t, J=7.8 Hz, 2H); 3.04-2.94 (m, 1H); 2.13-2.00 (m, 2H). $^{13}$C NMR (75 MHz, CDCl$_3$) δ: 157.73, 147.60, 146.22, 144.24, 141.63, 136.58, 131.52, 128.43, 121.51, 120.99, 120.03, 101.77, 100.91, 71.47, 55.58, 49.92, 48.48, 34.10, 26.32. HRMS (ESI) m/z calc'd for C$_{23}$H$_{25}$N$_3$O$_4$: 410.2080; Found: 410.2076.

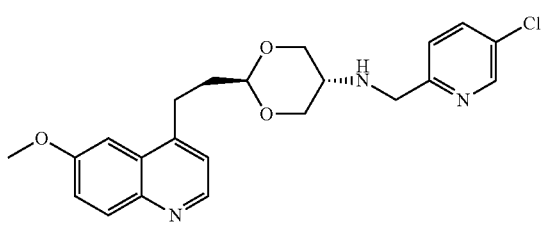 [SMILES: COc1ccc2nccc(CC[C@H]3OC[C@H](NCc4ccc(Cl)cn4)CO3)c2c1]
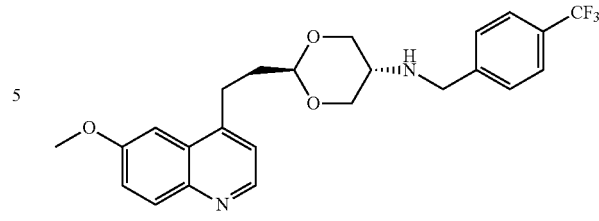

Example 46. [AB-0069] N-((5-chloropyridin-2-yl)methyl)-2-(2-(6-methoxyquinolin-4-yl)ethyl)-trans-1,3-dioxan-5-amine The title compound was prepared from amine 24 and 5-chloropicolinaldehydein 55% yield following the general method. $^1$H NMR (300 MHz, CDCl$_3$) δ: 8.65 (d, J=4.5 Hz, 1H); 8.51 (d, J=2.2 Hz, 1H); 8.03 (d, J=9.2 Hz, 1H); 7.63 (dd, J=8.3, 2.5 Hz, 1H); 7.38 (dd, J=9.2, 2.7 Hz, 1H); 7.31 (d, J=2.7 Hz, 1H); 7.23 (t, J=4.6 Hz, 2H); 4.49 (t, J=4.8 Hz, 1H); 4.23 (dd, J=11.2, 4.7 Hz, 2H); 3.95 (s, 3H); 3.92 (s, 2H); 3.35 (t, J=10.9 Hz, 2H); 3.14 (t, J=7.8 Hz, 2H); 3.04-2.94 (m, 1H); 2.10-2.03 (m, 2H). $^{13}$C NMR (75 MHz, CDCl$_3$) δ: 157.92, 157.43, 148.23, 147.12, 147.00, 143.56, 136.31, 130.98, 130.56, 128.53, 122.88, 121.88, 120.97, 101.88, 100.86, 71.45, 55.58, 51.84, 50.17, 34.13, 26.39. HRMS (ESI) m/z calc'd for C$_{22}$H$_{25}$ClN$_3$O$_3$: 414.1584; Found: 414.1577.

Example 48. [AB-0071] 2-(2-(6-methoxyquinolin-4-yl)ethyl)-N-(4-(trifluoromethyl)benzyl)-trans-1,3-dioxan-5-amine The title compound was prepared from amine 24 and 4-trifluoromethylbenzaldehyde in 54% yield following the general method. $^1$H NMR (300 MHz, CDCl$_3$) δ: 8.66 (d, J=4.4 Hz, 1H); 8.01 (d, J=9.1 Hz, 1H); 7.59 (d, J=8.1 Hz, 2H); 7.43 (d, J=8.0 Hz, 2H); 7.36 (dd, J=9.1, 2.8 Hz, 1H); 7.30 (d, J=2.7 Hz, 1H); 7.19 (d, J=4.5 Hz, 1H); 4.47 (t, J=4.9 Hz, 1H); 4.21 (dd, J=11.1, 4.7 Hz, 2H); 3.94 (s, 3H); 3.88 (s, 2H); 3.30 (t, j=10.8 Hz, 2H); 3.12 (t, J=7.8 Hz, 2H); 3.04-2.94 (m, 1H); 2.10-2.03 (m, 2H). $^{13}$C NMR (75 MHz, CDCl$_3$) δ: 157.72, 147.69, 146.06, 144.39, 144.24, 131.63, 129.81, 129.38, 128.42, 128.11, 125.95, 125.47, 125.42, 125.36, 122.35, 121.38, 120.96, 101.83, 100.93, 71.51, 55.52, 50.82, 49.96, 34.13, 26.31. HRMS (ESI) m/z calc'd for C$_{24}$H$_{26}$F$_3$N$_2$O$_3$: 447.1896; Found: 447.1867.

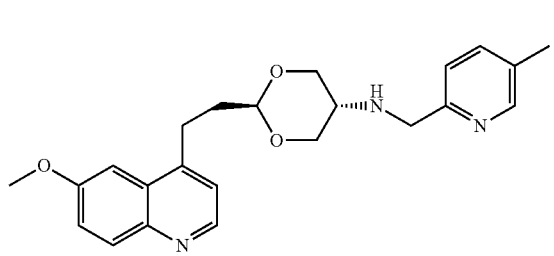
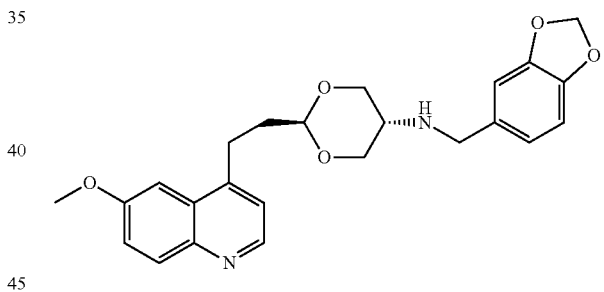

Example 47. [AB-0070] 2-(2-(6-methoxyquinolin-4-yl)ethyl)-N-((5-methylpyridin-2-yl)methyl)-trans-1,3-dioxan-5-amine The title compound was prepared from amine 24 and 5-methylpicolinaldehyde in 73% yield following the general method. $^1$H NMR (300 MHz, CD$_3$OD) δ: 8.54 (d, J=4.6 Hz, 1H); 8.39-8.32 (m, 1H); 7.94-7.86 (m, 1H); 7.65 (dd, J=7.9, 1.6 Hz, 1H); 7.43-7.34 (m, 3H); 7.32 (d, J=4.6 Hz, 1H); 4.56 (t, J=4.8 Hz, 1H); 4.22 (dd, J=11.3, 4.8 Hz, 2H); 3.94 (s, 3H); 3.92 (s, 2H); 3.43 (t, J=10.9 Hz, 2H); 3.15 (dd, J=9.0, 6.9 Hz, 2H); 3.04-2.91 (m, 1H); 2.35 (s, 3H); 2.08-1.96 (m, 2H). $^{13}$C NMR (75 MHz, CD$_3$OD) δ: 158.15, 155.31, 148.56, 147.87, 146.76, 143.25, 138.03, 132.69, 129.74, 128.50, 122.24, 121.89, 120.98, 101.55, 100.81, 70.04, 54.72, 50.58, 49.67, 34.00, 25.90, 16.62. HRMS (ESI) m/z calc'd for C$_{23}$H$_{28}$N$_3$O$_3$: 394.2131; Found: 394.2121.

Example 49. [AB-0079] N-(benzo[d][1,3]dioxol-5-ylmethyl)-2-(2-(6-methoxyquinolin-4-yl)ethyl)-trans-1,3-dioxan-5-amine The title compound was prepared from amine 24 and benzo[d][1,3]dioxole-5-carbaldehyde in 58% yield following the general method. $^1$H NMR (300 MHz, CDCl$_3$) δ: 8.65 (d, J=4.4 Hz, 1H); 8.00 (d, J=9.1 Hz, 1H); 7.35 (dd, J=9.1, 2.8 Hz, 1H); 7.29 (d, J=2.7 Hz, 1H); 7.18 (d, J=4.5 Hz, 1H); 6.81 (s, 1H); 6.74 (s, 2H); 5.93 (s, 2H); 4.46 (t, J=4.9 Hz, 1H); 4.19 (dd, J=10.8, 4.5 Hz, 2H); 3.93 (s, 3H); 3.71 (s, 2H); 3.28 (t, J=10.9 Hz, 2H); 3.11 (t, J=7.8 Hz, 2H); 3.03-2.93 (m, 1H); 2.11-2.00 (m, 2H). $^{13}$C NMR (75 MHz, CDCl$_3$) δ: 157.70, 147.84, 147.71, 146.78, 146.09, 144.40, 134.05, 131.63, 128.42, 121.39, 121.07, 120.94, 108.44, 108.17, 101.81, 100.97, 100.90, 71.58, 55.53, 51.18, 49.67, 34.17, 26.32. HRMS (ESI) m/z calc'd for C$_{24}$H$_{27}$N$_2$O$_5$: 423.1920; Found: 423.1936.

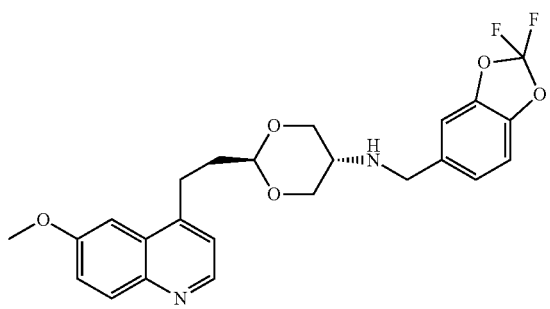 [SMILES: COc1ccc2nccc(CC[C@H]3OC[C@H](NCc4ccc5c(c4)OC(F)(F)O5)CO3)c2c1]

Example 50. [AB-0080] N-((2,2-difluorobenzo[d][1,3]dioxol-5-yl)methyl)-2-(2-(6-methoxyquinolin-4-yl)ethyl)-trans-1,3-dioxan-5-amine The title compound was prepared from amine 24 and 2,2-difluorobenzo[d][1,3]dioxole-5-carbaldehyde in 53% yield following the general method. $^1$H NMR (300 MHz, CDCl$_3$) δ: 8.66 (d, J=4.4 Hz, 1H); 8.01 (d, J=9.1 Hz, 1H); 7.36 (dd, J=9.1, 2.8 Hz, 1H); 7.29 (d, J=2.7 Hz, 1H); 7.19 (d, J=4.5 Hz, 1H); 7.08 (s, 1H); 6.99 (s, 2H); 4.46 (t, J=4.9 Hz, 1H); 4.20 (dd, J=11.1, 4.8 Hz, 2H); 3.94 (s, 3H); 3.80 (s, 2H); 3.29 (t, J=10.9 Hz, 2H); 3.12 (t, J=7.8 Hz, 2H); 3.02-2.92 (m, 1H); 2.09-2.02 (m, 2H). $^{13}$C NMR (75 MHz, CDCl$_3$) δ: 162.34, 157.74, 147.60, 146.19, 144.28, 144.00, 142.91, 136.41, 131.55, 128.43, 122.86, 121.44, 120.96, 109.21, 109.16, 101.83, 100.92, 71.45, 55.52, 50.86, 49.77, 34.12, 26.31. HRMS (ESI) m/z calc'd for C$_{24}$H$_{25}$F$_2$N$_2$O$_5$: 459.1732; Found: 459.1742.

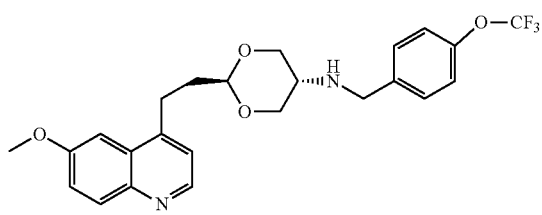 [SMILES: COc1ccc2nccc(CC[C@H]3OC[C@H](NCc4ccc(OC(F)(F)F)cc4)CO3)c2c1]

Example 51. [AB-0081] 2-(2-(6-methoxyquinolin-4-yl)ethyl)-N-(4-(trifluoromethoxy)benzyl)-trans-1,3-dioxan-5-amine The title compound was prepared from amine 24 and 4-trifluoromethoxybenzaldehyde in 62% a yield following the general method. $^1$H NMR (300 MHz, CDCl$_3$) δ: 8.67 (d, J=4.4 Hz, 1H); 8.02 (d, J=9.1 Hz, 1H); 7.40-7.29 (m, 5H); 7.23-7.15 (m, 3H); 4.48 (t, J=4.9 Hz, 1H); 4.23 (dd, J=11.2, 4.7 Hz, 2H); 3.95 (s, 3H); 3.83 (s, 2H); 3.31 (t, J=10.9 Hz, 2H); 3.14 (t, J=7.8 Hz, 2H); 3.06-2.96 (m, 1H); 2.13-2.02 (m, 2H). $^{13}$C NMR (75 MHz, CDCl$_3$) δ: 157.71, 148.39, 148.37, 147.69, 146.07, 144.39, 138.87, 131.62, 129.21, 128.42, 122.18, 121.39, 121.02, 120.95, 118.77, 101.82, 100.92, 71.52, 55.50, 50.52, 49.89, 34.14, 26.31. HRMS (ESI) m/z calc'd for C$_{24}$H$_{26}$F$_3$N$_2$O$_4$: 463.1845; Found: 463.1849.

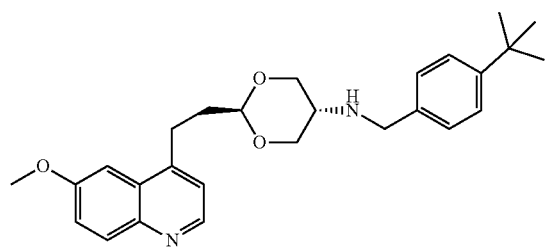 [SMILES: COc1ccc2nccc(CC[C@H]3OC[C@H](NCc4ccc(C(C)(C)C)cc4)CO3)c2c1]

Example 52. [AB-0082] N-(4-(tert-butyl)benzyl)-2-(2-(6-methoxyquinolin-4-yl)ethyl)-trans-1,3-dioxan-5-amine The title compound was prepared from amine 24 and 4-tert-butylbenzaldehyde in 60% yield following the general method. $^1$H NMR (300 MHz, CDCl$_3$) δ: 8.66 (d, J=4.4 Hz, 1H); 8.01 (d, J=9.1 Hz, 1H); 7.35 (dd, J=10.0, 1.8 Hz, 3H); 7.30 (d, J=2.7 Hz, 1H); 7.23 (d, J=8.3 Hz, 2H); 7.18 (d, J=4.4 Hz, 1H); 4.47 (t, J=4.9 Hz, 1H); 4.22 (dd, J=11.1, 4.7 Hz, 2H); 3.94 (s, 3H); 3.78 (s, 2H); 3.30 (t, J=10.8 Hz, 2H); 3.13 (t, J=7.8 Hz, 2H); 3.07-2.97 (m, 1H); 2.13-2.00 (m, 2H); 1.31 (s, 9H). $^{13}$C NMR (75 MHz, CDCl$_3$) δ: 157.70, 150.27, 147.71, 146.11, 144.41, 136.99, 131.63, 128.43, 127.68, 125.47, 121.41, 120.95, 101.81, 100.92, 55.52, 51.00, 49.79, 34.49, 34.19, 31.37, 26.34. HRMS (ESI) m/z calc'd for C$_{27}$H$_{35}$N$_2$O$_3$: 435.2648; Found: 435.2646.

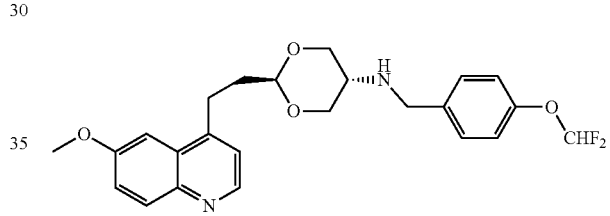

Example 53. [AB-0084] N-(4-(difluoromethoxy)benzyl)-2-(2-(6-methoxyquinolin-4-yl)ethyl)-trans-1,3-dioxan-5-amine The title compound was prepared from amine 24 and 4-(difluoromethoxy)benzaldehyde in 70% yield following the general method. $^1$H NMR (300 MHz, CDCl$_3$) δ: 8.65 (d, J=4.4 Hz, 1H); 8.00 (d, J=9.1 Hz, 1H); 7.38-7.27 (m, 4H); 7.18 (d, J=4.4 Hz, 1H); 7.07 (d, J=8.5 Hz, 2H); 6.48 (t, J=73.9 Hz, 1H); 4.46 (t, J=4.9 Hz, 1H); 4.20 (dd, J=11.1, 4.7 Hz, 2H); 3.93 (s, 3H); 3.79 (s, 2H); 3.29 (t, J=10.9 Hz, 2H); 3.12 (J=7.8 Hz, 2H); 3.03-2.93 (m, 1H); 2.11-2.00 (m, 2H). $^{13}$C NMR (75 MHz, CDCl$_3$) δ: 157.70, 150.30, 147.70, 146.07, 144.39, 137.37, 131.62, 129.31, 128.42, 121.38, 120.95, 119.68, 119.36, 115.92, 112.47, 101.82, 100.92, 71.53, 55.51, 50.58, 49.84, 34.14, 26.31. HRMS (ESI) m/z calc'd for C$_{24}$H$_{27}$F$_2$N$_2$O$_4$: 445.1939; Found: 445.1937.

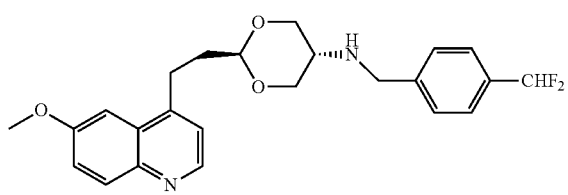 [SMILES: COc1ccc2nccc(CC[C@H]3OC[C@H](NCc4ccc(C(F)F)cc4)CO3)c2c1]

Example 54. [AB-0085] N-(4-(difluoromethyl)benzyl)-2-(2-(6-methoxyquinolin-4-yl)ethyl)-trans-1,3-dioxan-5-amine The title compound was prepared from amine 24 and 4-(difluoromethyl)benzaldehyde in 49% yield following the general method. $^1$H NMR (300 MHz, CDCl$_3$) δ: 8.65 (d, J=4.3 Hz, 1H); 8.01 (d, J=9.1 Hz, 1H); 7.44 (dd, J=21.7, 8.1 Hz, 4H); 7.36 (dd, J=9.2, 2.7 Hz, 1H); 7.29 (d, J=2.6 Hz, 1H); 7.19 (d, J=4.4 Hz, 1H); 6.61 (t, J=56.4 Hz, 1H); 4.47 (t, J=4.8 Hz, 1H); 4.21 (dd, J=11.1, 4.7 Hz, 2H); 3.94 (s, 3H); 3.86 (s, 2H); 3.30 (t, J=10.8 Hz, 2H); 3.12 (t, J=7.8 Hz, 2H); 3.04-2.94 (m, 1H); 2.13-1.99 (m, 2H). $^{13}$C NMR (75 MHz, CDCl$_3$) δ: 157.73, 147.64, 146.16, 144.32, 142.95, 133.75, 133.45, 133.16, 131.58, 128.43, 128.17, 125.87, 125.79, 125.71, 121.43, 120.96, 117.78, 114.62, 111.46, 101.82, 100.91, 71.50, 55.53, 50.49, 49.90, 34.13, 26.31. HRMS (ESI) m/z calc'd for C$_{24}$H$_{27}$F$_2$N$_2$O$_3$: 429.1990; Found: 429.1988.

Examples AB-0015, 0017, 0018, and 0059 to 0062 can be prepared from compound 28 and the requisite aldehyde according to Scheme 4.

Scheme 4

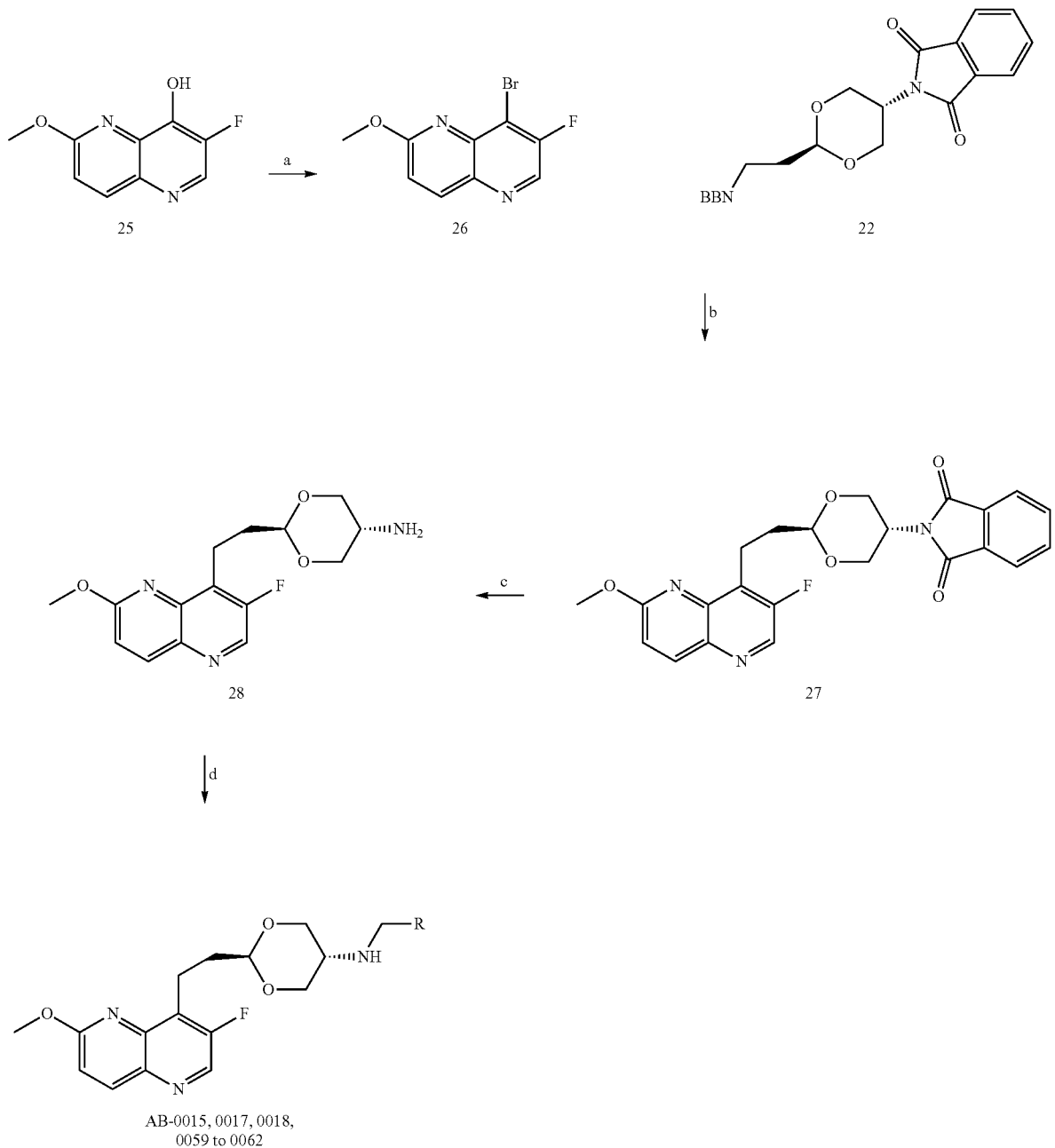

Reagents: (a) PBr$_3$, DMF, 70° C., 99%; (b) Cs$_2$CO$_3$, Pd(dppf)$_2$Cl$_2$, THF, room temp, 58%; (c) ethanolamine, ethyl acetate, 70° C., 80%. (d) RCHO, ZnCl$_2$, methanol, NaBH$_3$CN, room temp, overnight.

8-bromo-7-fluoro-2-methoxy-1,5-naphthyridine (26)

To a solution of commercial 3-fluoro-6-methoxy-1,5-naphthyridin-4-ol (compound 25, 862.5 mg, 4 mmol) in DMF (10 mL) was dropped phosphorus tribromide (466 μL, 4.8 mmol) at 0° C. under N$_2$ atmosphere. The reaction mixture was stirred for 1 hour, then water (200 mL) and sodium hydroxide aqueous solution (6N, 740 μL) was added. The reaction mixture was stirred for 2 hours, and the precipitated solid was collected by filtration to afford compound 26 as a tan solid (1.03 g). $^1$H NMR (CDCl$_3$) δ: 4.17 (t, 3H); 7.11-7.14 (d, 1H); 8.21-8.24 (d, 1H); 8.64 (s, 1H).

2-(2-(2-(3-fluoro-6-methoxy-1,5-naphthyridin-4-yl)ethyl)-trans-1,3-dioxan-5-yl)isoindoline-1,3-dione (27)

To a mixture of compound 26 (128.5 mg, 0.5 mmol), cesium carbonate (325.8 mg, 1 mmol), [1,1'-Bis(diphenylphosphino)ferrocene]dichloropalladium(1) (13.4 mg, 0.018 mmol) and THF (3 mL), the fresh solution of compound 22 (prepared as described previously) was dropped at room temperature under N$_2$ atmosphere. The reaction mixture was stirred overnight. Then the solvent was moved and the mixture was extracted with dichloromethane and washed with brine. The combined organic layer was concentrated and purified by chromatography on silica gel with hexane/ethyl acetate (3:1) to give compound 27 as a white solid (126.4 mg). $^1$H NMR (CDCl$_3$) δ: 2.09-2.16 (q, 2H); 3.30-3.35 (t, 2H); 3.99-4.04 (dd, 2H); 4.11 (s, 3H); 4.37-4.40 (t, 2H); 4.57-4.64 (m, 1H); 4.71-4.74 (t, 1H); 7.04-7.07 (d, 1H); 7.70-7.75 (m, 2H); 7.80-7.84 (m, 2H); 8.15-8.18 (d, 1H); 8.61 (s, 1H).

2-(2-(3-fluoro-6-methoxy-1,5-naphthyridin-4-yl)ethyl)-trans-1,3-dioxan-5-amine (28)

A mixture of compound 27 (218.7 mg, 0.5 mmol), ethanolamine (46 μL, 7.5 mmol) and ethyl acetate (4 mL) was stirred and heated at 70° C. overnight. The solvent was removed, and the mixture was extracted with dichloromethane and washed with brine. Then the organic layer was combined and concentrated, the crude product was purified by chromatography on silica gel with dichloromethane/methanol (15:1) to give 28 as an oil (123.1 mg). $^1$H NMR (CDCl$_3$) δ: 1.09 (brs, 2H); 1.97-2.09 (m, 2H); 3.00-3.08 (m, 1H); 3.14-3.26 (m, 4H); 4.06-4.14 (m, 5H); 4.40-4.43 (t, 1H); 7.02-7.05 (d, 1H); 8.12-8.15 (d, 1H); 8.58 (s, 1H).

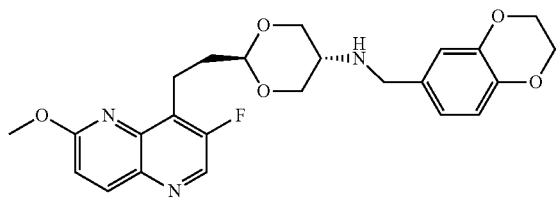 [SMILES: COc1ccc2ncc(F)c(CC[C@H]3OC[C@H](NCc4ccc5c(c4)OCCO5)CO3)c2n1]

Example 55. [OSUAB-0015] N-((2,3-dihydrobenzo[b][1,4]dioxin-6-yl)methyl)-2-(2-(3-fluoro-6-methoxy-1,5-naphthyridin-4-yl)ethyl)-trans-1,3-dioxan-5-amine The title compound was prepared from amine 28 and 2,3-dihydrobenzo[b][1,4]dioxine-6-carbaldehyde in 52% yield following the general method. $^1$H NMR (300 MHz, CDCl$_3$) δ: 8.59 (s, 1H); 8.15 (d, J=8.0 Hz, 1H); 7.04 (d, J=9.0 Hz, 1H); 6.71-6.81 (m, 3H); 4.44 (t, J=5.0 Hz, 1H); 4.23 (s, 4H); 4.15 (dd, J=11.1, 4.7 Hz, 2H); 4.07 (s, 3H); 3.67 (s, 2H); 3.21-3.27 (m, 4H); 2.90-2.95 (m, 1H); 2.05 (td, J=7.6, 5.2 Hz, 2H). $^{13}$C NMR (75 MHz, CDCl$_3$) δ: 162.29, 158.77, 155.39, 143.49, 142.73, 141.61, 141.52, 140.09, 138.49, 138.46, 138.08, 137.70, 133.49, 131.77, 131.60, 120.89, 117.22, 116.76, 115.11, 115.07, 101.57, 71.58, 64.36, 53.77, 50.77, 49.59, 33.45, 18.31. HRMS (ESI) m/z calc'd for C$_{24}$H$_{26}$FN$_3$O$_5$Na: 478.1754; Found: 478.1370.

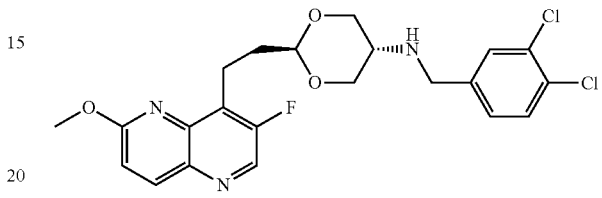

Example 56. [OSUAB-0017] N-(3,4-dichlorobenzyl)-2-(2-(3-fluoro-6-methoxy-1,5-naphthyridin-4-yl)ethyl)-trans-1,3-dioxan-5-amine The title compound was prepared from amine 28 3,4-dichlorobenzaldehyde in 45% yield following the general method. $^1$H NMR (300 MHz, CDCl$_3$) δ: 8.60 (s, 1H); 8.16 (d, J=9.0 Hz, 1H); 7.37-7.42 (m, 2H); 7.13 (dd, J=8.2, 1.8 Hz, 1H); 7.06 (d, J=9.0 Hz, 1H); 4.45 (t, J=5.0 Hz, 1H); 4.16 (dd, J=11.2, 4.7 Hz, 2H); 4.08 (s, 3H); 3.76 (s, 2H) 3.27 (dd, J=12.7, 9.1 Hz, 4H); 2.88-2.95 (m, 1H); 2.07 (td, J=7.6, 5.3 Hz, 2H). $^{13}$C NMR (75 MHz, CDCl$_3$) δ: 162.31, 158.77, 155.39, 141.61, 141.51, 140.46, 140.12, 138.51, 138.48, 138.08, 137.71, 132.56, 131.70, 131.53, 131.14, 130.39, 129.79, 127.18, 115.14, 101.62, 71.40, 53.77, 50.11, 49.85, 33.39, 18.29. HRMS (ESI) m/z calc'd for C$_{22}$H$_{23}$Cl$_2$FN$_3$O$_3$: 466.1101; Found: 466.1088.

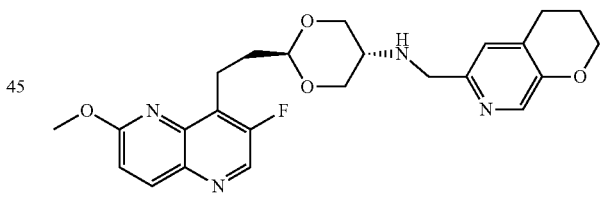

Example 57. [OSUAB-0018] N-((3,4-dihydro-2H-pyrano[2,3-c]pyridin-6-yl)methyl)-2-(2-(3-fluoro-6-methoxy-1,5-naphthyridin-4-yl)-trans-1,3-dioxan-5-amine The title compound was prepared from amine 28 and 3,4-dihydro-2H-pyrano[2,3-c]pyridine-6-carbaldehyde in 77% yield following the general method. $^1$H NMR (300 MHz, CDCl$_3$) δ: 8.58 (s, 1H); 8.14 (d, J=9.0 Hz, 1H); 8.05 (s, 1H); 7.04 (d, J=9.0 Hz, 1H); 6.95 (s, 1H); 4.47 (t, J=5.0 Hz, 1H); 4.22-4.15 (m, 4H); 4.07 (s, 3H); 3.81 (s, 2H); 3.37 (t, J=10.8 Hz, 2H); 3.26 (t, J=7.6 Hz, 2H); 3.02-2.95 (m, 1H); 2.76 (t, J=6.5 Hz, 2H); 2.08-2.00 (m, 4H). $^{13}$C NMR (75 MHz, CDCl$_3$) δ: 162.31, 158.75, 155.37, 151.35, 148.89, 141.59, 141.50, 140.07, 138.48, 138.06, 137.69, 131.73, 131.56, 122.92, 115.14, 101.62, 70.92, 66.62, 53.80, 51.35, 50.01, 33.39, 24.25, 21.51, 18.28. HRMS (ESI) m/z calc'd for $C_{24}H_{27}FN_4O_4Na$: 477.1914; Found: 477.1895.

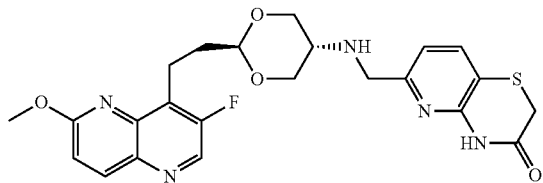 [SMILES: COc1ccc2ncc(F)c(CC[C@H]3OC[C@H](NCc4ccc5c(n4)NC(=O)CS5)CO3)c2n1]

Example 58. [OSUAB-0059] 6-(((2-(2-(3-fluoro-6-methoxy-1,5-naphthyridin-4-yl)ethyl)-trans-1,3-dioxan-5-yl)amino)methyl)-2H-pyrido[3,2-b][1,4]thiazin-3(4H)-one The title compound was prepared from amine 28 and 3-oxo-3,4-dihydro-2H-pyrido[3,2-b][1,4]thiazine-6-carbaldehyde in 44% yield following the general method. $^1$H NMR (300 MHz, CDCl$_3$) δ: 8.61 (s, 1H); 8.60 (s, 1H); 8.16 (d, J=9.0 Hz, 1H); 7.57 (d, J=7.8 Hz, 1H); 7.05 (d, J=9.0 Hz, 1H); 6.94 (d, J=7.8 Hz, 1H); 4.45 (t, J=5.0 Hz, 1H); 4.17 (dd, J=11.2, 4.7 Hz, 2H); 4.07 (s, 3H); 3.82 (s, 2H); 3.47 (s, 2H); 3.35-3.24 (m, 4H); 2.94 (tt, J=9.8, 4.7 Hz, 1H); 2.06 (td, J=7.6, 5.2 Hz, 2H). $^{13}$C NMR (75 MHz, CDCl$_3$) δ: 165.59, 162.30, 158.77, 156.62, 155.39, 148.30, 141.60, 141.51, 140.10, 138.47, 138.07, 137.70, 136.24, 131.73, 131.56, 117.74, 115.13, 115.10, 113.87, 101.63, 71.41, 53.77, 51.56, 49.99, 33.42, 29.65, 18.30. HRMS (ESI) m/z calc'd for $C_{23}H_{25}FN_5O_4S$: 486.1611; Found: 486.1596.

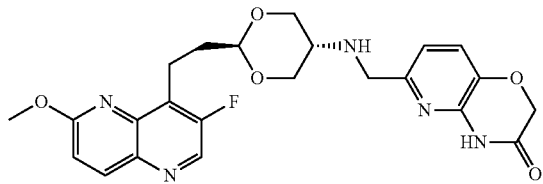 [SMILES: COc1ccc2ncc(F)c(CC[C@H]3OC[C@H](NCc4ccc5c(n4)NC(=O)CO5)CO3)c2n1]

Example 59. [OSUAB-0060] 6-(((2-(2-(3-fluoromethoxy-1,5-naphthyridin-4-yl)ethyl)-trans-1,3-dioxan-5-yl)amino)methyl)-2H-pyrido[3,2-b][1,4]oxazin-3(4H)-one The title compound was prepared from amine 28 and 3-oxo-3,4-dihydro-2H-pyrido[3,2-b][1,4]oxazine-6-carbaldehyde in 43% yield following the general method. $^1$H NMR (300 MHz, CDCl$_3$) δ: 8.60 (s, 1H); 8.17 (d, J=9.0 Hz, 1H); 7.21 (d, J=8.0 Hz, 1H); 7.06 (d, J=9.0 Hz, 1H); 6.91 (d, J=8.1 Hz, 1H); 4.65 (s, 2H); 4.47 (t, J=5.0 Hz, 1H); 4.18 (dd, J=11.2, 4.7 Hz, 2H); 4.08 (s, 3H); 3.81 (s, 2H); 3.57 (brs, 1H); 3.39-3.24 (m, 4H); 3.01-2.92 (m, 1H); 2.06 (td, J=7.5, 5.3 Hz, 2H). $^{13}$C NMR (75 MHz, CDCl$_3$) δ: 165.28, 162.31, 158.77, 155.35, 141.61, 141.52, 140.11, 138.50, 138.34, 138.08, 137.70, 131.55, 124.22, 118.15, 115.10, 101.65, 71.25, 67.25, 53.77, 51.32, 49.93, 33.40, 29.69, 18.27. HRMS (ESI) m/z calc'd for $C_{23}H_{25}FN_5O_5$: 470.1840; Found: 470.1821.

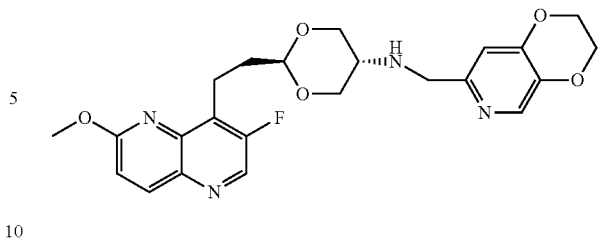

Example 60. [OSUAB-0061] N-((2,3-dihydro-[1,4]dioxino[2,3-c]pyridin-7-yl)methyl)-2-(2-(3-fluoro-6-methoxy-1,5-naphthyridin-4-yl)ethyl)-trans-1,3-dioxan-5-amine The title compound was prepared from amine 28 and 2,3-dihydro-[1,4]dioxino[2,3-c]pyridine-7-carbaldehyde in 43% yield following the general method. $^1$H NMR (300 MHz, CDCl$_3$) δ: 8.58 (s, 1H); 8.14 (d, J=9.0 Hz, 1H); 8.08 (s, 1H); 7.04 (d, J=9.0 Hz, 1H); 6.75 (s, 1H); 4.44 (t, J=5.0 Hz, 1H); 4.33-4.23 (m, 4H); 4.15 (dd, J=11.2, 4.7 Hz, 2H); 4.06 (s, 3H); 3.75 (s, 2H); 3.35-3.22 (m, 4H); 3.00-2.86 (m, 1H); 2.04 (td, J=7.6, 5.2 Hz, 2H). $^{13}$C NMR (75 MHz, CDCl$_3$) δ: 162.29, 158.76, 155.38, 152.92, 150.23, 141.60, 141.51, 140.19, 140.06, 138.90, 138.46, 138.44, 138.05, 137.68, 131.79, 131.63, 115.12, 115.08, 110.63, 101.58, 71.52, 64.97, 64.02, 53.77, 51.97, 49.91, 33.45, 18.27. HRMS (ESI) m/z calc'd for $C_{23}H_{26}FN_4O_5$: 457.1887; Found: 457.1871.

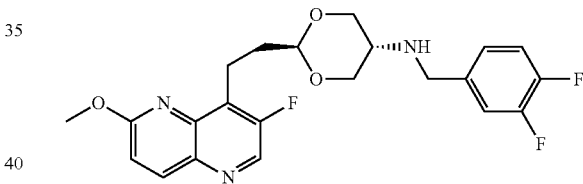

Example 61. [OSUAB-0062] N-(3,4-difluorobenzyl)-2-(2-(3-fluoro-6-methoxy-1,5-naphthyridin-4-yl)ethyl)-trans-1,3-dioxan-5-amine The title compound was prepared from amine 28 and 3,4-difluorobenzaldehyde in 43% yield following the general method. $^1$H NMR (400 MHz, CDCl$_3$) δ: 8.59 (s, 1H); 8.15 (d, J=5.3 Hz, 1H); 7.18-7.03 (m, 3H); 7.02-6.97 (m, 1H); 4.44 (t, J=5.1 Hz, 1H); 4.18-4.13 (m, 2H); 4.07 (s, 3H); 3.75 (s, 2H); 3.30-3.22 (m, 4H); 2.97-2.89 (m, 1H); 2.11-2.02 (m, 2H). $^{13}$C NMR (100 MHz, CDCl$_3$) δ: 162.31, 158.35, 155.81, 151.66, 151.54, 150.81, 150.68, 149.19, 149.07, 148.35, 148.22, 141.59, 141.53, 140.10, 138.49, 138.47, 138.02, 137.74, 137.32, 137.27, 137.23, 131.70, 131.58, 123.63, 123.60, 123.57, 123.54, 117.19, 117.02, 116.59, 115.15, 115.12, 101.61, 71.47, 53.77, 50.25, 49.80, 33.40, 18.29. HRMS (ESI) m/z calc'd for $C_{22}H_{23}F_3N_3O_3$: 434.1692; Found: 434.1682.

Examples AB-0016, 0017, 0019, 0020, and 0046 can be prepared from compound 34 and the requisite aldehyde according to Scheme 5.

Scheme 5

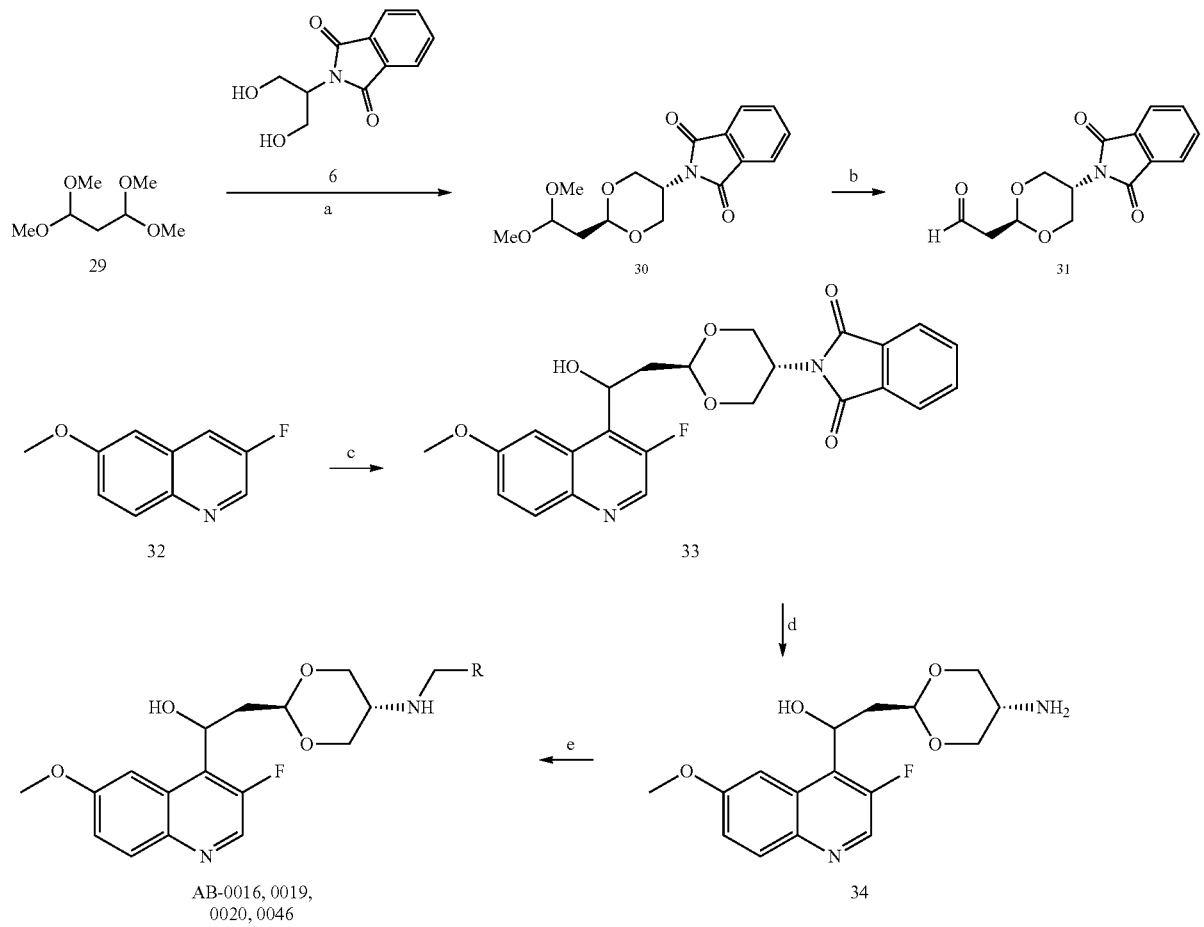

Reagents: (a) p-toluenesulfonic acid (cat.), 85-90° C., 6 h, 60% (b) pyridinium p-toluenesulfonate (cat.), H₂O, 80° C., 8-12 h, 76%. (c) i) Lithium diisopropylamide, THF, -78° C., then ii) add 31, THF, -78° C., to rt, 30%. (d) ethanolamine, ethyl acetate, 70° C., 16 h, 68%. (e) RCHO, ZnCl₂, methanol, NaBH₃CN, room temp, overnight.

2-(2-(2,2-dimethoxyethyl)-trans-1,3-dioxan-5-yl)isoindoline-1,3-dione (30)

To a stirring solution of diol 6 (6.0 g, 27.1 mmol, 1.0 equiv), and p-toluenesulfonic acid monohydrate (300 µg, 1.36 mmol, 0.1 equiv) in a three-neck flask, was added tetramethoxypropane 29 (8.91 g, 54.2 mmol, 2.0 equiv) at rt. A Dean Stark apparatus was attached, and the temperature was raised gradually to 90° C. and stirred for 6 h. The reaction was cooled to rt, and quenched with triethylamine (200 µL), and was followed by removal of toluene by blowing air to the mixture. The residue was purified by chromatography (20% ethyl acetate-hexanes) to give the title compound as a white solid (5.23 g, 16.3 mmol, 600/0). ¹H NMR (CDCl₃, 400 MHz): δ 7.84 (dd, J=5.5, 3.1 Hz, 2H), 7.73 (dd, J=5.5, 3.0 Hz, 2H), 4.77 (t, J=5.4 Hz, 1H), 4.56-4.66 (m, 2H), 4.43 (t, J=10.8 Hz, 2H), 4.02 (dd, J=10.8, 4.9 Hz, 2H), 3.36 (s, 6H), 2.00 (t, J=5.6 Hz, 2H).

2-(5-(1,3-dioxoisoindolin-2-yl)-trans-1,3-dioxan-2-yl)acetaldehyde (31)

To a stirred solution of 30 (5.23 g, 16.3 mmol) in water, was added pyridinium p-toluenesulfonate (409 mg, 1.63 mmol, 0.1 equiv) and stirred for 12 h at 80° C. (a reflux condenser was attached). Upon consumption of starting material, CH₂Cl₂ was added at rt, and the two layers were separated. The aqueous layer was extracted with CH₂C₂₁ (3×25 mL), and the combined organic layers were washed with brine, dried over Na₂SO₄, filtered, and concentrated under vacuum. The residue was purified by chromatography (1-3% methanol/dichloromethane) to give the title compound as a white solid (3.38 g, 12.3 mmol, 76%). ¹H NMR (CDCl₃, 400 MHz): δ 9.83 (t, J=2.2 Hz, 1H), 7.85 (dd, J=5.6, 3.1 Hz, 2H), 7.74 (dd, J=5.5, 3.1 Hz, 2H), 5.14 (t, J=4.6 Hz, 1H), 4.60-4.68 (m, 1H), 4.45-4.50 (m, 1H), 4.04-4.08 (m, 1H), 2.76 (dd, J=4.6, 2.2 Hz, 2H).

2-(2-(2-(3-fluoro-6-methoxyquinolin-4-yl)-2-hydroxyethyl)-trans-1,3-dioxan-5-yl)isoindoline-1,3-dione (33)

To a solution of diisopropylamine (65 µL, 466 µmol, 1.1 equiv) in THF (3 mL) was added n-butyllithium (200 µL of a 2.5 M solution in hexanes, 1.1 equiv), and stirred under N₂ for 5 min at 0° C. Stirring was continued for 15 min at 0° C., then cooled to -78° C. followed by addition of a solution of 32 (75 mg, 424 µmol, 1.0 equiv) in THF (3 mL). After 3 h at -78° C., a solution of aldehyde 31 (140 µg, 509 µmol, 1.2 equiv) in THF (2 mL) was added dropwise via cannula, warmed gradually to room temperature, and stirred for 3 h. Saturated ammonium chloride solution was added to quench the reaction, and the aqueous phase was extracted with diethyl ether (3×10 mL). The combined organic layers were washed with brine, dried (Na$_2$SO$_4$), filtered, and concentrated under vacuum. The residue was purified by chromatography (4% CH$_3$OH—CH$_2$Cl$_2$) to give the title compound as a yellow solid (56 mg, 124 μmol, 30%). $^1$H NMR (CD$_3$)$_2$SO, 400 MHz): δ 8.69 (d, J=1.6 Hz, 1H), 7.96 (d, J=9.2 Hz, 1H), 7.89 (d, J=2.7 Hz, 1H), 7.82-7.89 (m, 4H), 7.39 (dd, J=9.2, 2.7 Hz, 1H), 5.95 (d, J=4.2 Hz, 1H), 5.55-5.59 (m, 1H), 4.74 (dd, J=6.1, 4.2 Hz, 1H), 4.16-4.26 (m, 2H), 4.01-4.07 (m, 2H), 3.90 (s, 3H), 2.40 (ddd, J=13.3, 8.1, 4.0 Hz, 1H), 2.07 (dt, J=12.5, 5.9 Hz, 1H).

2-(5-amino-trans-1,3-dioxan-2-yl)-1-(3-fluoro-6-methoxyquinolin-4-yl)ethan-1-ol (34)

To a solution of 33 (69.5 mg, 154 μmol) in ethyl acetate (10 mL) was added ethanolamine (141 mg, 230 μmol, 139 μL, 15 equiv) and stirred for 16 h at 70° C. Water was added to the reaction mixture, and the aqueous layer extracted with dichloromethane (3×5 mL). The combined organic layers were washed with brine, and dried (Na$_2$SO$_4$), filtered, and concentrated under vacuum. The residue was purified by chromatography (5% CH$_3$OH—CH$_2$Cl$_2$) to give the title compound as a transparent semi-solid (33.5 mg, 104 μmol, 68%). $^1$H NMR (CDCl$_3$, 400 MHz): δ 8.47 (d, J=1.9 Hz, 1H), 7.89 (d, J=9.2 Hz, 1H), 7.73 (d, J=2.6 Hz, 1H), 7.24 (dd, J=9.2, 2.6 Hz, 1H), 5.74 (dd, J=9.3, 3.9 Hz, 1H), 4.62 (t, J=4.8 Hz, 1H), 4.08-4.13 (m, 2H), 3.88 (3H, s), 3.20 (dt, J=10.6, 3.3 Hz, 2H), 3.05 (ddd, J=15.1, 10.0, 4.7 Hz, 1H), 2.51 (ddd, J=14.2, 9.2, 4.8 Hz, 1H), 2.05 (dt, J=14.3, 4.3 Hz, 1H).

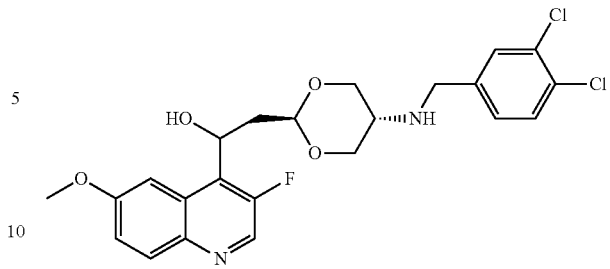

Example 63. [OSUAB-0019] 2-(5-(((3,4-dichlorobenzyl)amino)-trans-1,3-dioxan-2-yl)-1-(3-fluoro-6-methoxyquinolin-4-yl)ethan-1-ol The title compound was prepared from amine 34 and 3,4-dichlorobenzaldehyde in 51% yield following the general method. $^1$H NMR (CD$_3$OD, 400 MHz): $^1$H NMR (CD$_3$OD, 400 MHz): δ 8.54 (d, J=2.3 Hz, 1H), 7.92 (d, J=9.3 Hz, 1H), 7.85 (d, J=2.7 Hz, 1H), 7.52 (d, J=1.9 Hz, 1H), 7.45 (d, J=8.2 Hz, 1H), 7.35 (dd, J=9.3, 2.7 Hz, 1H), 7.25 (dd, J=8.2, 2.0 Hz, 1H), 5.70 (dd, J=8.1, 6.1 Hz, 1H), 4.59 (dd, J=5.8, 4.6 Hz, 1H), 4.08-4.18 (m, 2H), 3.93 (s, 3H), 3.72 (s, 2H), 3.26-3.35 (m, 2H), 2.80 (ddd, J=15.4, 10.5, 4.9 Hz, 1H), 2.44 (ddd, J=13.8, 8.1, 4.4 Hz, 1H), 2.14 (dt, J=13.9, 6.0 Hz, 1H); $^{13}$C NMR (CD$_3$OD, 100 MHz): δ 159.8, 156.7, 154.2, 142.7, 142.3, 139.3, 139.0, 133.3, 133.1, 133.0, 131.8, 131.5, 131.2, 129.5, 129.1, 122.3, 104.6, 100.7, 71.9, 64.0, 56.1, 50.8, 50.5, 49.6, 42.3; HRMS (ESI) m/z calc'd for C$_{24}$H$_{27}$Cl$_2$FN$_2$O$_4$: 481.1097; Found: 481.1093.

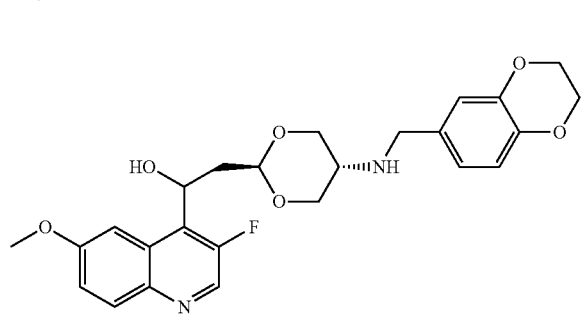 [SMILES: COc1ccc2ncc(F)c(C(O)C[C@H]3OC[C@H](NCc4ccc5c(c4)OCCO5)CO3)c2c1]

Example 62. [OSUAB-0016] 2-(5-(((2,3-dihydrobenzo[b][1,4]dioxin-6-yl)methyl)amino)-trans-1,3-dioxan-2-yl)-1-(3-fluoro-6-methoxyquinolin-4-yl)ethan-1-ol The title compound was prepared from amine 34 and 2,3-dihydrobenzo[b][1,4]dioxine-6-carbaldehyde in 69% yield following the general method. $^1$H NMR (CD$_3$OD, 400 MHz): δ 8.54 (d, J=2.3 Hz, 1H), 7.92 (d, J=9.2 Hz, 1H), 7.84 (d, J=2.7 Hz, 1H), 7.35 (dd, J=9.3, 2.7 Hz, 1H), 6.82 (d, J=1.1 Hz, 1H), 6.74-6.78 (m, 2H), 5.69 (dd, J=8.1, 6.0 Hz, 1H), 4.58 (dd, J=5.8, 4.6 Hz, 1H), 4.22 (s, 4H), 4.05-4.14 (m, 2H), 3.93 (s, 3H), 3.61 (s, 2H), 3.25-3.34 (m, 2H), 2.81 (ddd, J=15.3, 10.5, 4.8 Hz, 1H), 2.43 (ddd, J=13.7, 7.9, 4.5 Hz, 1H), 2.13 (dt, J=13.8, 5.9 Hz, 1H); $^{13}$C NMR (CD$_3$OD, 100 MHz): δ 159.9, 145.0, 144.3, 139.3, 139.0, 134.0, 131.5, 122.3, 118.2, 118.1, 104.6, 100.7, 71.8, 65.6, 64.0, 56.1, 51.2, 50.5, 42.3; HRMS (ESI) m/z calc'd for C$_{25}$H$_{25}$FN$_2$O$_6$: 471.1931; Found: 471.1933.

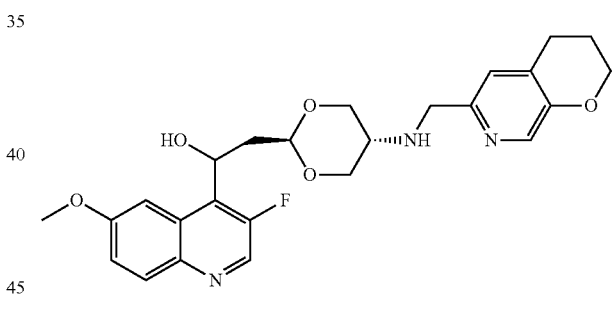

Example 64. [OSUAB-0020] 2-(5-(((3,4-dihydro-2H-pyrano[2,3-c]pyridin-6-yl)methyl)amino)-trans-1,3-dioxan-2-yl)-1-(3-fluoro-6-methoxyquinolin-4-yl)ethan-1-ol The title compound was prepared from amine 34 and 3,4-dihydro-2H-pyrano[2,3-c]pyridine-6-carbaldehyde in 31% yield following the general method. $^1$H NMR (CD$_3$OD, 400 MHz): δ 8.54 (d, J=2.2 Hz, 1H), 7.98 (s, 1H), 7.91 (d, J=9.3 Hz, 1H), 7.85 (d, J=2.7 Hz, 1H), 7.35 (dd, J=9.3, 2.7 Hz, 1H), 7.14 (s, 1H), 5.69 (dd, J=8.1, 6.0 Hz, 1H), 4.63 (dd, J=5.7, 4.5 Hz, 1H), 4.14-4.25 (m, 4H), 3.93 (s, 3H), 3.87 (s, 2H), 3.34-3.43 (m, 2H), 2.99 (ddd, J=15.2, 10.2, 4.7 Hz, 1H), 2.82 (t, J=6.4 Hz, 2H), 2.45 (ddd, J=13.7, 8.2, 4.3 Hz, 1H), 2.14 (dt, J=13.8, 6.0 Hz, 1H), 1.99-2.05 (m, 2H); $^{13}$C NMR (CD$_3$OD, 100 MHz): δ 159.9, 154.2, 153.1, 142.8, 139.3, 139.0, 138.9, 133.0, 131.6, 129.9, 124.7, 122.3, 104.7, 104.6, 100.8, 70.9, 67.9, 64.0, 56.1, 51.3, 50.7, 42.1, 25.2, 22.5, 15.4; HRMS (ESI) m/z calc'd for C$_{25}$H$_{29}$FN$_3$O$_5$: 470.2091; Found: 470.2089.

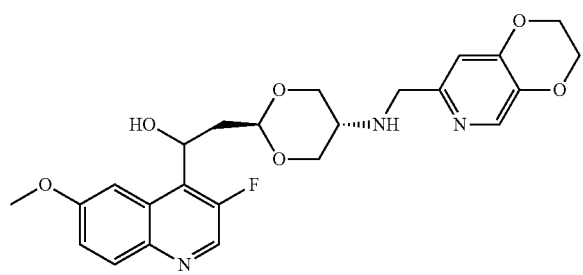 [SMILES: COc1ccc2ncc(F)c(C(O)C[C@H]3OC[C@H](NCc4cc5c(cn4)OCCO5)CO3)c2c1]

Example 65. [OSUAB-0046] 2-(5-(((2,3-dihydro-[1,4]dioxino[2,3-c]pyridin-7-yl)-trans-1,3-dioxan-2-yl)-1-(3-fluoro-6-methoxyquinolin-4-yl)ethan-1-ol The title compound was prepared from amine 34 and 2,3-dihydro-[1,4]dioxino[2,3-c]pyridine-7-carbaldehyde in 69% yield following the general method. $^1$H NMR (CD$_3$OD, 400 MHz): δ 8.53 (d, J=2.2 Hz, 1H), 8.00 (s, 1H), 7.90 (d, J=9.3 Hz, 1H), 7.83 (d, J=2.7 Hz, 1H), 7.34 (dd, J=9.2, 2.7 Hz, 1a), 6.96 (s, 1a), 5.68 (dd, J=8.1, 6.1 Hz, 1H), 4.58 (dd, J=5.6, 4.7 Hz, 1H), 4.35-4.39 (m, 2H), 4.28-4.32 (m, 2H), 4.09-4.18 (m, 2H), 3.92 (s, 3H), 3.76 (s, 2H), 3.28-3.38 (m, 2H), 2.85 (ddd, J=14.8, 9.9, 4.3 Hz, 1H), 2.81 (ddd, J=13.7, 8.1, 4.4 Hz, 1H), 2.13 (dt, J=13.8, 6.0 Hz, 1H); $^{13}$C NMR (CD$_3$OD, 100 MHz): δ 159.9, 156.7, 154.2, 141.7, 139.3, 139.0, 138.7, 133.1, 133.0, 131.5, 129.5, 122.3, 112.3, 104.6, 104.5, 100.7, 71.5, 66.6, 65.4, 64.0, 61.5, 56.1, 51.0, 42.2; HRMS (ESI) m/z calc'd for C$_{24}$H$_{27}$FN$_3$O$_6$: 472.1884; Found: 472.1883.

Examples AB-0076, 0077, and 0078 can be prepared from compound 37 and the requisite aldehyde according to Scheme 6.

Scheme 6

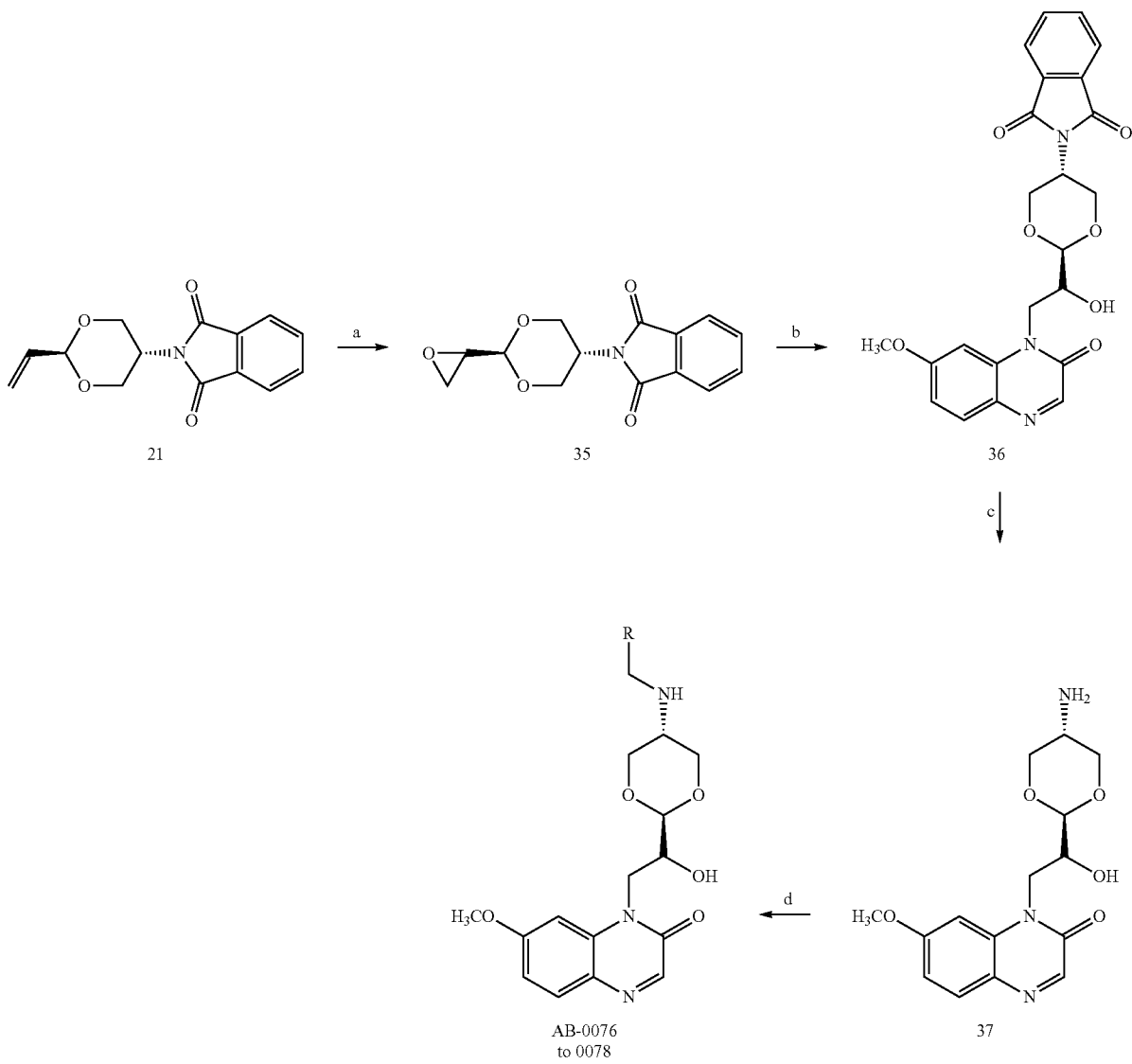

Reagents: (a) m-chloroperbenzoic acid, NaHCO$_3$, dichloromethane, room temp, 2 d, 71%. (b) 4, Cs$_2$CO$_3$, DMF, 80° C., 14 h, 13%. (c) ethanolamine, ethyl acetate, reflux, overnight, 63%. (d) RCHO, ZnCl$_2$, methanol, NaBH$_3$CN, room temp, overnight.

2-(2-(oxiran-2-yl)-trans-1,3-dioxan-5-yl)isoindoline-1,3-dione (35)

To a solution of alkene 21 (5.60 g, 10.8 mmol, 1.0 euiv.) in dichloromethane (200 mL) was added m-CPBA (3.72 g, 21.6 mmol, 2.0 equiv.) portion wise at room temperature and reaction mixture was stirred at same for 14 h. Next day another portion of m-CPBA (3.72 g, 21.6 mmol, 2.0 equiv.) was added and mixture was stirred for four days at room temperature. The reaction mixture was diluted with dichloromethane, washed with NaOH (1 M, 3×200 mL) and brine (200 mL). The organic layer was dried over sodium sulfate and concentrated to get crude material which was purified by flash column chromatography on silica gel with hexane/ethyl acetate (1:7) to afford the title compound as a white solid (6.40 g, 71%). $^1$H NMR (400 MHz, CDCl$_3$) δ: 7.86-7.81 (m, 2H); 7.76-7.71 (m, 2H); 4.70-4.62 (m, 1H); 4.59 (d, J=4.0 Hz, 1H); 4.48-4.41 (m, 2H); 4.12-4.05 (m, 2H); 3.15-3.13 (m, 1H); 2.85-2.81 (m, 2H). $^{13}$C NMR (100 MHz, CDCl$_3$) δ: 167.9; 134.5; 131.6; 123.6; 100.1; 66.41; 66.38; 51.4; 44.0; 43.9. HRMS (ESI) m/z calc'd for C$_{14}$H$_{14}$NO$_5$ [M+H]$^+$: 276.0872; found: 276.0870.

2-(2-(1-hydroxy-2-(7-methoxy-2-oxoquinoxalin-1(2H)-yl)ethyl)-trans-1,3-dioxan-5-yl)isoindoline-1,3-dione (36)

A mixture of compound 4 (0.60 g, 3.41 mmol, 1.0 equiv), epoxide 35 (1.40 g, 5.11 mmol, 1.5 equiv) and cesium carbonate (2.22 g, 6.82 mmol, 2.0 equiv)) in anhydrous N,N-dimethylformamide (12 mL) was stirred at 80° C. for 14 h. Reaction mixture was cooled, volatiles were removed under reduced pressure. Obtained crude material was partitioned between ethyl acetate (70 mL) and water (50 mL). Organic layer separated, aqueous layer extracted with ethyl acetate (2×30 mL). Combined organic layers were washed with brine, dried over sodium sulfate and concentrated to get crude material which was purified using column chromatography on silica gel with dichloromethane/methanol (3:1) to afford the title compound as a white solid (200 mg, 13%). $^1$H NMR (400 MHz, CDCl$_3$) δ: 8.14 (s, 1H); 7.87-7.82 (m, 2H); 7.80 (d, J=8.8 Hz, 1H); 7.77-7.70 (m, 2H); 6.98 (d, J=2.3 Hz, 1H); 6.94 (dd, J=2.5, 8.9 Hz, 2H); 4.88 (d, J=3.6 Hz, 1H); 4.70-4.62 (m, 2H); 4.51 (td, J=3.1, 10.9 Hz, 2H); 4.39 (dd, J=2.5, 14.7 Hz, 1H); 4.16-4.08 (m, 3H); 3.91 (s, 3H). $^{13}$C NMR (100 MHz, CDCl$_3$) δ: 167.9; 162.2; 156.8; 146.1; 134.6; 131.9; 131.6; 128.6; 123.7; 111.8; 101.1; 98.4; 71.2; 66.5; 66.4; 55.9; 44.6; 44.2. HRMS (ESI) m/z calc'd for C$_{23}$H$_{22}$N$_3$O$_7$ [M+H]$^+$: 452.1458; found: 452.1453.

1-(2-(5-amino-trans-1,3-dioxan-2-yl)-2-hydroxyethyl)-7-methoxyquinoxalin-2(1H)-one (37)

A mixture of alcohol 36 (0.38 g. 0.84 mmol, 1.0 equiv), ethanolamine (1.53 mL, 25.3 mmol, 30 equiv) and ethyl acetate (30 mL) was stirred at 80° C. overnight. The solvent was removed, the mixture was dissolved in 10% methanol in dichloromethane (100 mL) and washed with brine. Aqueous layer was extracted with 10% methanol in dichloromethane (4×25 mL) The combined organic layers dried over sodium sulfate, concentrated, and the crude product was purified by chromatography on silica gel with dichloromethane/methanol (9:1) to give the title compound as a white solid (0.17 g, 0.53 mmol, 63%). $^1$H NMR (300 MHz, DMSO-d$_6$) δ: 8.02 (s, 1H); 7.72 (d, J=8.8 Hz, 1H); 7.07 (d, J=2.5 Hz, 1H); 6.97 (dd, J=2.5, 8.9 Hz, 1H); 5.18 (d, J=5.9 Hz, 1H); 4.45 (d, J=4.2 Hz, 1H); 4.33 (dd, J=9.1, 14.0 Hz, 1H); 4.21 (dd, J=3.5, 14.1 Hz, 1H); 4.04-3.96 (m, 2H); 3.89-3.81 (m, 4H); 3.21 (t, J=10.7 Hz, 2H); 2.86-2.76 (m, 1H); 1.42 (br s, 2H). 13C NMR (100 MHz, DMSO-d$_6$) δ: 160.9; 154.9; 146.3; 135.0; 130.9; 127.9; 110.9; 101.4; 99.4; 72.69; 72.66; 68.5; 55.7; 44.3; 43.6. HRMS (ESI) m/z calc'd for C$_{15}$H$_{20}$N$_3$O$_5$ [M+H]$^+$: 322.1403; found: 322.1401.

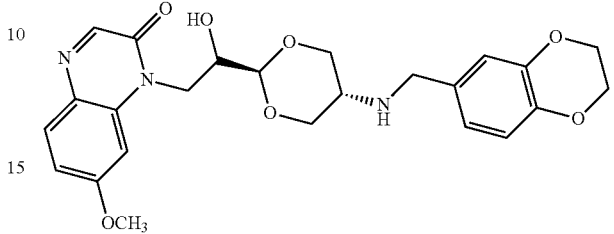

Example 66. [OSUAB-0076] 1-(2-(5-(((2,3-dihydrobenzo[b][1,4]dioxin-6-yl)methyl)amino)-trans-1,3-dioxan-2-yl)-2-hydroxyethyl)-7-methoxyquinoxalin-2(1H)-one The title compound was prepared from amine 37 and 2,3-dihydrobenzo[b][1,4]dioxine-6-carbaldehyde in 31% yield following the general method. $^1$H NMR (400 MHz, CD$_3$OD) δ: 7.99 (s, 1H); 7.70 (d, J=8.9 Hz, 1H); 7.08 (d J=1.9 Hz, 1H); 6.96 (dd, J=2.1, 8.9 Hz, 1H); 6.83 (s, 1H); 6.77 (s, 2H); 4.58 (d, J=3.4 Hz, 1H); 4.49 (dd, J=8.8, 14.2 Hz, 1H); 4.33-4.17 (m, 7H); 4.03-3.98 (m, 1H); 3.90 (s, 3H); 3.66 (s, 2H); 3.41 (t, J=10.6 Hz, 2H); 2.96-2.88 (m, 1H). $^{13}$C NMR (100 MHz, CD$_3$OD) δ: 163.5; 157.5; 146.8; 145.0; 144.4; 136.0; 133.7; 132.2; 129.8; 122.3; 118.23; 118.18; 113.3; 102.9; 100.0; 71.64; 71.61; 70.5; 65.61; 65.58; 56.4, 51.1, 50.5; 45.0. HRMS (ESI) m/z calc'd for C$_{24}$H$_{28}$N$_3$O$_7$ [M+H]$^+$: 470.1927; found: 470.1925.

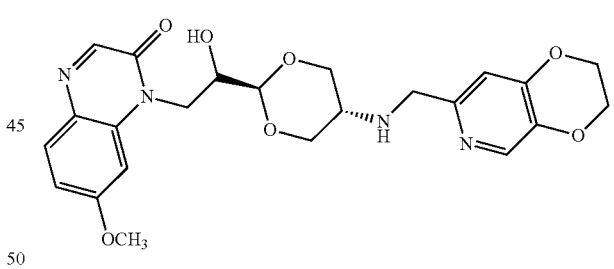

Example 67. [OSUAB-0077] 1-(2-(5-(((2,3-dihydro-[1,4]dioxino[2,3-c]pyridin-7-yl)methyl)amino)-trans-1,3-dioxan-2-yl)-2-hydroxyethyl)-7-methoxyquinoxalin-2(1H)-one The title compound was prepared from amine 37 and 2,3-dihydro-[1,4]dioxino[2,3-c]pyridine-7-carbaldehyde in 30% yield following the general method. $^1$H NMR (400 MHz, CD$_3$OD) δ: 8.00 (s, 2H), 7.72 (d, J=8.9 Hz, 1H); 7.12 (d, J=1.6 Hz, 1H); 6.99 (d, J=2.1 Hz, 1H); 6.97 (s, 1H); 4.60 (d, J=3.4 Hz, 1H); 4.52 (dd, J=8.9, 14.1 Hz, 1H); 4.42-4.28 (m, 5H); 4.27-4.16 (m, 2H); 4.07-4.0 (m, 1H); 3.92 (s, 3H); 3.78 (s, 2H); 3.42 (t, J=10.2 Hz, 1H); 2.94-2.87 (m, 1H). $^{13}$C NMR (100 MHz, CD$_3$OD) δ: 163.4; 157.5; 153.9; 152.7; 146.8; 142.2; 139.0; 136.0; 132.3; 129.8; 113.3; 112.2;

102.9; 100.0; 71.7; 70.5; 66.5; 65.4; 56.4; 52.0; 50.8; 45.0. HRMS (ESI) m/z calc'd for $C_{23}H_{27}N_4O_7[M+H]^+$: 471.1880; found: 471.1877.

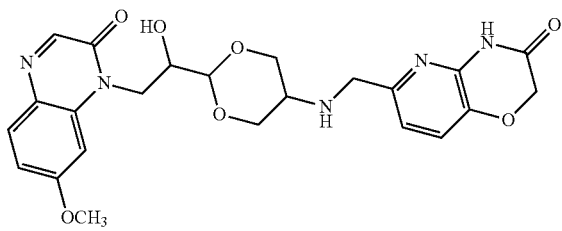 [SMILES: COc1ccc2ncc(=O)n(CC(O)C3OCC(NCc4ccc5c(n4)NC(=O)CO5)CO3)c2c1]

Example 68. [OSUAB-0078] 6-(((2-(1-hydroxy-2-(7-methoxy-2-oxoquinoxalin-1(2H)-yl)ethyl)-trans-1,3-dioxan-5-yl)amino)methyl)-2H-pyrido[3,2-b][1,4]oxazin-3(4H)-one The title compound was prepared from amine 37 and 3-oxo-3,4-dihydro-2H-pyrido[3,2-b][1,4]oxazine-6-carbaldehyde in 19% yield following the general method. $^1$H NMR (400 MHz, DMSO-$d_6$) δ: 11.18 (s, 1H); 8.03 (s, 1H); 7.72 (d, J=8.8 Hz, 1H); 7.32 (d, J=8.1 Hz, 1H); 7.07 (d, J=2.4 Hz, 1H); 7.02 (d, J=8.1 Hz, 1H); 6.98 (dd, J=2.5, 8.9 Hz, 1H); 5.20 (d, J=5.9 Hz, 1H); 4.62 (s, 2H); 4.50 (d, J=4.1 Hz, 1H); 4.32 (dd, J=9.3, 14.0 Hz, 1H); 4.23-4.12 (m, 3H); 3.89-3.82 (s, 4H), 3.71 (s, 2H); 3.31 (t, J=10.5 Hz, partially obscured by water, 1H); 2.82-2.75 (m, 1H); 2.15 (br, s, 1H). HRMS (ESI) m/z calc'd for $C_{23}H_{26}N_5O_7$ [M+H]$^+$: 484.1832; found: 484.1828.

Examples AB-0075, 0088, and 0089 can be prepared according to Scheme 7.

Scheme 7

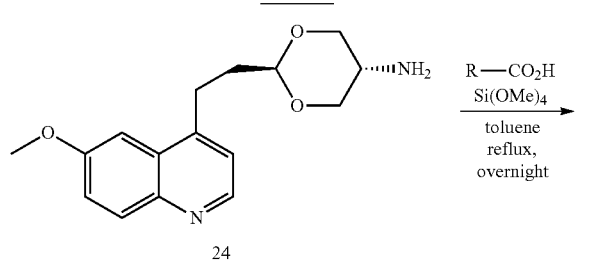

AB-0075, 0088, 0089

General procedure: The direct amidation was prepared according to literature (Braddock, D. C.; Lickiss, P. D.; Rowley, B. C.; Pugh, D.; Purnomo, T.; Santhakumar, G.; Fussell, S. *J., Org. Lett.* 2018, 20, 950-953) with slight modification. Amine 24 (0.043 g, 0.149 mmol, 1 equiv) and the requisite carboxylic acid (0.225 mmol, 1.5 equiv) were charged into a two-necked round bottomed flask with a cold finger. Toluene (1 mL) added by syringe. After adding tetramethylorthosilicate (45 uL, 0.302 mmol, 2 equiv) into the mixture, the mixture was stirred at room temperature for 10 minutes under $N_2$ atmosphere. Then, the mixture was heated to reflux overnight. The mixture was cooled down to room temperature, the solvent was removed. After diluting with DCM, the resulting solution was transferred to a separating funnel. Aqueous potassium carbonate (0.3M, 3 mL) was added, then solid sodium chloride was added until saturation. The aqueous phase was extracted with DCM. The combined organic phase was transferred to a separating funnel again, and the resulting solution was added aqueous hydrochloride solution (1M, 3 mL), then solid sodium chloride was added until saturation. The aqueous phase was extracted with DCM. The combined organic phase was dried and concentrated, the crude product was purified by chromatography on silica gel with hexane/ethyl acetate (gradient 0% to 100%) to give the desired compound.

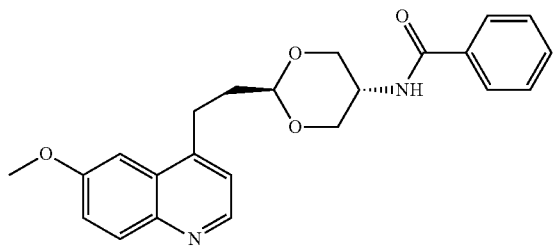 [SMILES: COc1ccc2nccc(CC[C@H]3OC[C@H](NC(=O)c4ccccc4)CO3)c2c1]

Example 69. [OSUAB-0075] N-(2-(2-(6-methoxyquinolin-4-yl)ethyl)-trans-1,3-dioxan-5-yl)benzamide The title compound was prepared from amine 24 and benzoic acid in 42% yield (95% purity with 5% unknown impurities) following the general method. $^1$H NMR (300 MHz, CDCl$_3$) δ: 8.66 (br s, 1H); 8.24 (s, 1H); 7.74 (dd, J=7.1, 1.8, 3H); 7.55-7.39 (m, 5H); 5.75 (d, J=8.3, 1H); 4.57 (t, J=4.6, 1H); 4.53-4.33 (m, 3H); 3.99 (s, 3H); 3.50 (t, J=10.7, 2H); 3.22 (d, J=8.0, 2H); 2.18-2.10 (m, 2H). HRMS (ESI) m/z calc'd for $C_{23}H_{24}N_2O_4$ [M+H]$^+$: 393.1814, found: 393.1813.

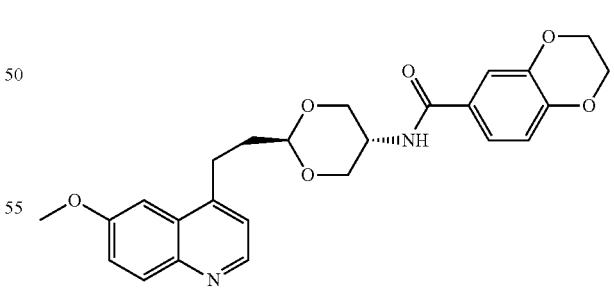

Example 70. [OSUAB-0088] N-(2-(2-(6-methoxyquinolin-4-yl)ethyl)-trans-1,3-dioxan-5-yl)-2,3-dihydrobenzo[b][1,4]dioxine-6-carboxamide The title compound was prepared from amine 24 and 2,3-dihydrobenzo[b][1,4]dioxine-6-carboxylic acid in 33% yield (88% purity with 12% unknown impurities) following the general method. ¹H NMR (300 MHz, CDCl₃) &: 8.67 (br s, 1H), 8.21 (d, J=8.9, 1H), 7.45-7.21 (m, partially obscured by solvent, 5H), 6.88 (d, J=8.4, 1H), 5.61 (d, J=8.3, 1H), 4.56 (t, J=4.7, 1H), 4.47-4.26 (m, 7H), 3.98 (s, 3H), 3.47 (t, J=10.6, 2H), 3.23 (t, J=8.0, 2H), 2.16-2.13 (m, 2H). HRMS (ESI) m/z calc'd for C₂₅H₂₇N₂O₆ [M+H]⁺: 451.1869; found: 451.1848.

7.38 (s, 2H), 6.11 (s, 1H), 4.58 (s, 1H), 4.54-4.41 (m, 1H), 4.33 (dd, J=10.5, 4.1, 2H), 3.99 (s, 3H), 3.57 (t, J=10.8, 2H), 3.26 (t, J=7.9, 2H), 2.20-2.09 (m, 2H). HRMS (ESI) m/z calc'd for C₂₃H₂₃Cl₂N₂O₄ [M+H]⁺: 461.1035; found: 461.1058.

Example AB-0083 can be prepared according to Scheme 8.

Scheme 8

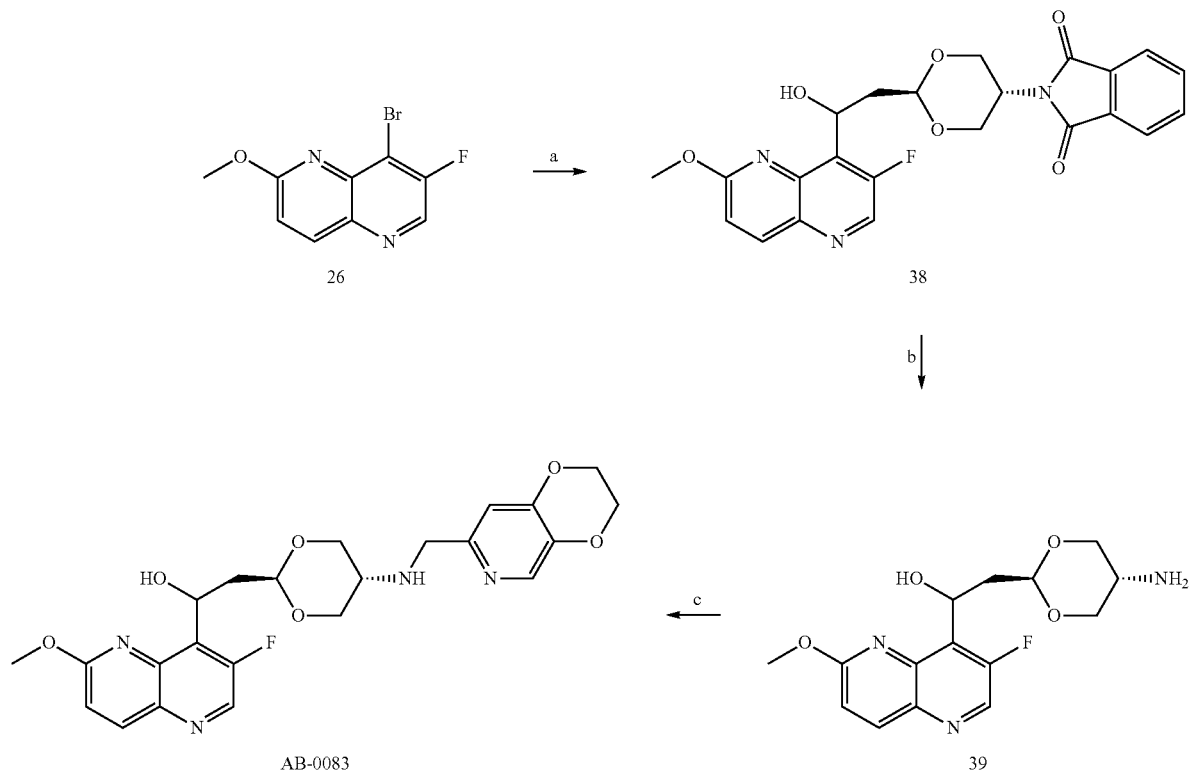

(a) i) n-hexyllithium, THF, -78° C., then ii) add to 31, THF, -78° C., to -20° C., 18%. (d) ethanolamine, ethyl acetate, 70° C., overnight, 66%. (e) RCHO, ZnCl₂, methanol, NaBH₃CN, room temp, overnight, 73%.

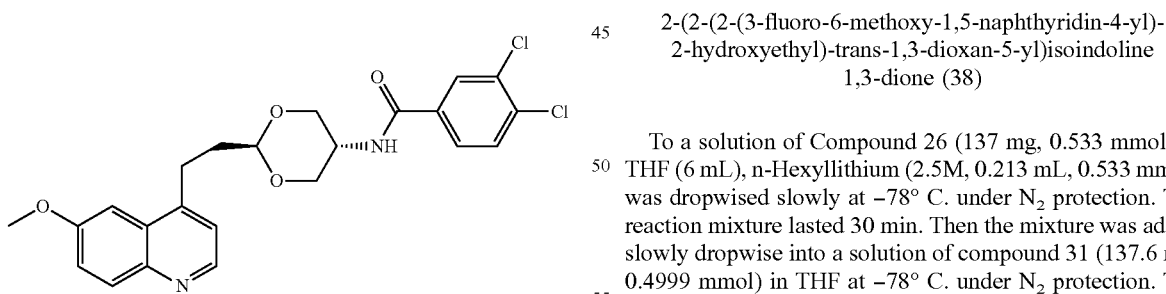

Example 71. [OSUAB-00891] 3,4-dichloro-N-(2-(2-(6-methoxyquinolin-4-yl)ethyl)-trans-1,3-dioxan-5-yl)benzamide The title compound was prepared from amine 24 and 3,4-dichlorobenzoic acid in 29% yield (90% purity with 10% unknown impurities) following the general method. ¹H NMR (300 MHz, CDCl₃) δ: 8.65 (s, 1H), 8.25 (d, J=9.1, 1H), 7.88 (s, 1H), 7.62 (d, J=8.3 Hz, 1H), 7.50-7.44 (m, 2H), 2-(2-(2-(3-fluoro-6-methoxy-1,5-naphthyridin-4-yl)-2-hydroxyethyl)-trans-1,3-dioxan-5-yl)isoindoline 1,3-dione (38)

To a solution of Compound 26 (137 mg, 0.533 mmol) in THF (6 mL), n-Hexyllithium (2.5M, 0.213 mL, 0.533 mmol) was dropwised slowly at −78° C. under N₂ protection. The reaction mixture lasted 30 min. Then the mixture was added slowly dropwise into a solution of compound 31 (137.6 mg, 0.4999 mmol) in THF at −78° C. under N₂ protection. The reaction mixture lasted 2 hours at −78° C., then the temperature was raised to −20° C. gradually. After 3 hours, the reaction was quenched by the addition of NH₄Cl solution (5 mL). Chromatography was performed on silica gel with hexane/ethyl acetate (1:1) to give the title compound as a white solid (40.4 mg, 0.0891 mmol, 18%). ¹H NMR (300 MHz, CDCl₃) &: 8.65 (s, 1H); 8.25 (d, J=9.2 Hz, 1H); 7.78 (ddd, J=31.3, 5.5, 3.1 Hz, 4H); 7.12 (d, J=9.1 Hz, 1H); 6.10 (d, J=10.4 Hz, 1H); 5.68-5.56 (m, 1H); 4.98 (dd, J=6.5, 3.8 Hz, 1H); 4.62 (ddd, J=15.7, 10.9, 4.7 Hz, 1H); 4.44 (td, J=10.7, 6.6 Hz, 2H); 4.15-3.95 (m, 5H); 2.61-2.48 (m, 1H); 2.29-2.16 (m, 1H).

2-(5-amino-trans-1,3-dioxan-2-yl)-1-(3-fluoro-6-methoxy-1,5-naphthyridin-4-yl)ethanol (39)

Compound 38 (40.2 mg, 0.0891 mmol) was suspended in ethyl acetate (2 mL), ethanolamine (0.081 mL, 1.34 mmol) was added and the mixture was heated to 70° C. overnight and then washed by brine. Chromatography was done on silica gel with methanol/dichloromethane (1:20) to give the title compound as a yellow oil (18.9 mg, 0.0585 mmol, 66%). $^1$H NMR (300 MHz, CDCl$_3$) δ: 8.62 (d, J=0.9 Hz, 1H); 8.22 (d, J=9.2 Hz, 1H); 7.09 (d, J=9.1 Hz, 1H); 5.57 (dd, J=8.7, 5.0 Hz, 1H); 4.68 (dd, J=6.6, 3.8 Hz, 1H); 4.18-3.97 (m, 5H); 3.22 (td, J=10.6, 6.2 Hz, 2H); 3.04 (ddd, J=15.1, 10.1, 4.7 Hz, 1H); 2.47 (ddd, J=13.8, 8.7, 3.8 Hz, 1H); 2.15 (ddd, J=13.9, 6.5, 5.0 Hz, 1H). $^{13}$C NMR (75 MHz, CDCl$_3$) δ: 161.88, 156.55, 153.12, 141.14, 140.89, 140.82, 138.76, 138.73, 138.39, 130.54, 130.38, 115.61, 115.58, 99.19, 73.49, 73.40, 64.88, 64.83, 54.27, 44.12, 42.90.

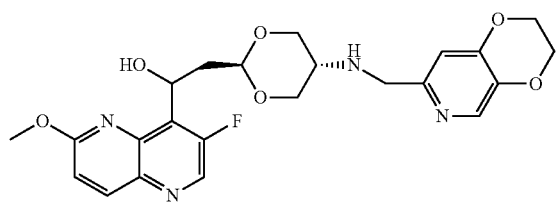 [SMILES: COc1ccc2ncc(F)c(C(O)C[C@H]3OC[C@H](NCc4cc5c(cn4)OCCO5)CO3)c2n1]

Example 72. [AB-0083] 2-(5-(((2,3-dihydro-[1,4]dioxino[2,3-c]pyridin-7-yl)methyl)amino)-trans-1,3-dioxan-2-yl)-1-(3-fluoro-6-methoxy-1,5-naphthyridin-4-yl)ethanol The title compound was prepared from amine 39 and 2,3-dihydro-[1,4]dioxino[2,3-c]pyridine-7-carbaldehyde in 73% yield following the general method. $^1$H NMR (300 MHz, CDCl$_3$) δ: 8.64 (d, J=1.0 Hz, 1H); 8.24 (d, J=9.1 Hz, 1H); 8.10 (s, 1H); 7.11 (d, J=9.1 Hz, 1H); 6.78 (s, 1H); 5.59 (dd, J=8.4, 4.7 Hz, 1H); 4.73 (dd, J=6.6, 3.8 Hz, 1H); 4.37-4.26 (m, 4H); 4.26-4.12 (m, 2H); 4.07 (s, 3H); 3.78 (s, 2H); 3.37 (td, J=10.6, 5.7 Hz, 2H); 3.02-2.89 (m, 1H); 2.31 (dddd, J=13.9, 11.5, 7.6, 4.4 Hz, 2H). $^{13}$C NMR (75 MHz, CDCl$_3$) δ: 161.88, 156.54, 153.11, 152.63, 150.26, 141.14, 140.91, 140.83, 140.24, 138.90, 138.76, 138.72, 138.39, 130.54, 130.37, 115.60, 115.57, 110.68, 99.51, 71.44, 71.35, 64.97, 64.88, 64.82, 64.02, 54.29, 51.88, 49.88, 42.98. HRMS (ESI) m/z calc'd for C$_{23}$H$_{26}$FN$_4$O$_6$: 473.1836; Found: 473.1838.

Example 73. NBTIs with Tricyclic LHS Moieties

Tricyclic NBTI's may be synthesized as shown in Scheme 9, 10, or 11.

Scheme 9

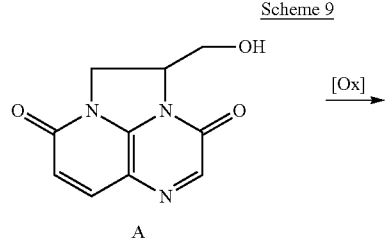

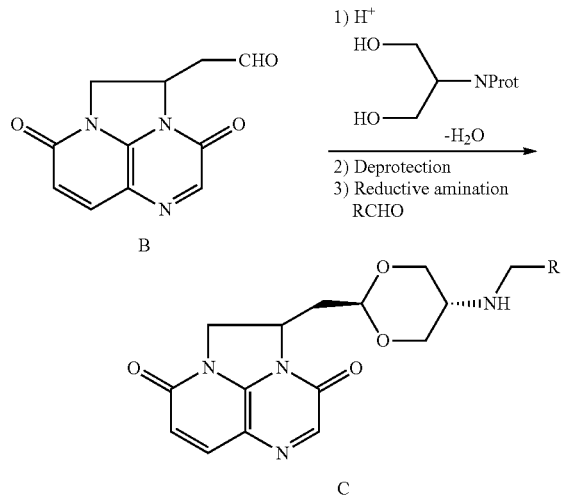

In Scheme 9, the alcohol A (WO2009/141398) can be oxidized to aldehyde B. Aldehyde B can be cyclized to a dioxane under dehydrating conditions, followed by N-deprotection, and reductive amination to afford compounds C.

Scheme 10

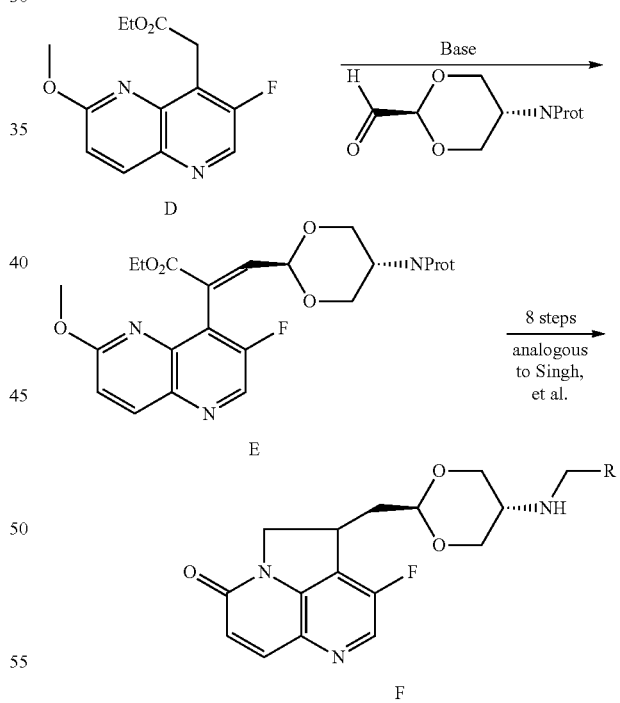

In Scheme 10, the ester D (Singh, S. B., et al. *Bioorg. Med. Chem. Lett.* 2015, 25, 1831) can be condensed with an appropriate N-protected aldehyde to afford alkene E. Additional steps analogous to those described in Singh, S. B. et al. can provide compounds F.

Alternatively, as in Scheme 11, alkene G (Miles, T. J., et al. *Bioorg. Med Chem. Lett.* 2013, 23, 5437) can be subjected to cross-metathesis with compound 21 and an appropriate metathesis catalyst to afford alkene H. Reduction of the alkene, deprotection of the phthalimide, and reductive amination can provide compounds F.

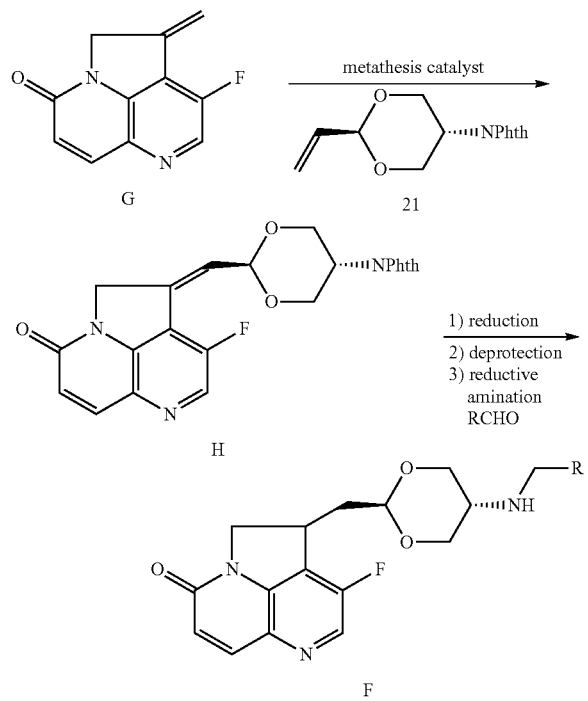

Scheme 11

Biological Activity of Examples 1-72

Minimum inhibitory concentrations were determined using the quality control strain *S. aureus* ATCC 29213 (Table 1) by the broth microdilution method according to guidelines of the Clinical and Laboratory Standards Institute (CLSI) (Cockerill, F. R.; et al., 2012, Methods for dilution antimicrobial susceptibility tests for bacteria that grow aerobically; approved standard-ninth edition. MA07-A9. Clinical and Laboratory Standard Institute, Wayne, Pa.). At a minimum, compounds were tested in triplicate, using both gepotidacin (WO/2016027249) and ciprofloxacin as positive controls. Published quality control ranges for gepotidacin and ciprofloxacin were used to validate each assay. MICs for selected compounds were also determined using a USA 300 strain of MRSA (Hidron, et al., *Lancet Infect. Dis.* 2009, 9:384-392). Vancomycin was used as an additional control.

Susceptibility to ciprofloxacin eroded considerably for the MRSA strain (ca. 64-fold increase in MIC). In contrast, MICs for the novel NBTIs showed no significant increases, highlighting the promise of NBTIs to tackle pre-existing forms of drug resistance.

A subset of analogs was used to assess the degree of inhibition of DNA gyrase or TopoIV (Inspiralis, Norwich, UK), both to establish the mechanism of action and to evaluate the relative balance of inhibitory activities (Table 1). A subset of compound was also assayed to determine the degree of inhibition of human topoisomerase II (Inspiralis, Norwich, UK)). As shown in Table 1, the described examples lacked significant inhibition of hTopoII at 100 µM concentration.

Assay Details

In all experiments, the activity of the enzymes was determined prior to the testing of the compounds and 1 unit (U) was defined as the amount of enzyme required to just fully supercoil, relax or decatenate the substrate (see explanation of gels). This amount of enzyme was initially used in determination of control inhibitor activity. These experiments were performed in duplicate.

For all assays the final DMSO concentration was 1%. 10 mM stocks of the compounds were serially diluted into 10% DMSO at 1 mM, 0.5 mM, 0.25 mM, 0.1 mM, 0.05 mM, 0.01 mM, 0.005 mM, 0.001 mM, 0.0005 mM, 0.0001 mM and 0.00005 mM. 3.0 µl of each dilution was added to a 30 µl assay.

Bands were visualised by ethidium staining for 20 minutes and destaining for 20 minutes. Gels were scanned using documentation equipment (GeneGenius, Syngene, Cambridge, UK) and % inhibition levels (where appropriate) were obtained with gel scanning software. (GeneTools, Syngene, Cambridge, UK)

*Staphylococcus aureus* gyrase supercoiling

1 U of DNA gyrase was incubated with 0.5 µg of relaxed pBR322 DNA in a 30 µl reaction at 37° C. for 30 minutes under the following conditions: 40 mM HEPES. KOH (pH 7.6), 10 mM magnesium acetate, 10 mM DTT, 2 mM ATP, 500 mM potassium glutamate and 0.05 mg/ml BSA.

Each reaction was stopped by the addition of 30 µl chloroform/iso-amyl alcohol (26:1) and 30 µl Stop Dye (40% sucrose (w/v), 100 mM Tris.HCl (pH 7.5), 10 mM EDTA, 0.5 µg/ml bromophenol blue), before being loaded on a 1.0% TAE gel run at 70V for 2 hours.

*Staphylococcus aureus* Topo IV Decatenation Assay

1 U of Topo IV was incubated with 200 ng kDNA DNA in a 30 µl reaction at 37° C. for 30 minutes under the following conditions: 50 mM Tris.HCl (7.5), 5 mM MgCl$_2$, 5 mM DTT, 1.5 mM ATP, 350 mM potassium glutamate and 0.05 mg/ml BSA.

Each reaction was stopped by the addition of 30 µl chloroform/iso-amyl alcohol (26:1) and 30 µl Stop Dye, before being loaded on a 1.0% TAE gel run at 70V for 2 hours.

Topoisomerase II (Alpha) Decatenation Assay

1 U of human topo II was incubated with 200 ng kDNA in a 30 µl reaction at 37° C. for 30 minutes under the following conditions: 50 mM Tris HCl (pH 7.5), 125 mM NaCl, 10 mM MgCl$_2$, 5 mM DTT, 0.5 mM EDTA, 0.1 mg/ml bovine serum albumin (BSA) and 1 mM ATP.

Each reaction was stopped by the addition of 30 µl chloroform/iso-amyl alcohol (26:1) and 30 µl Stop Dye, before being loaded on a 1.0% TAE gel run at 90V for 2 hours.

TABLE 1

| | Biological Activity of Example Compounds 1-72 | | | | |
|---|---|---|---|---|---|
| AB # | MIC 29213 (µg/mL) | MIC USA300 (µg/mL) | Gyrase IC50 (µM) | TopoIV Decat IC50 (µM) | hTopoII (% activity remaining at 100 µM) |
| 0002 | 4 | ND | 2.01 | >100 | 97.51 |
| 0003 | 8 | ND | ND | ND | ND |

TABLE 1-continued

Biological Activity of Example Compounds 1-72

| AB # | MIC 29213 (μg/mL) | MIC USA300 (μg/mL) | Gyrase IC50 (μM) | TopoIV Decat IC50 (μM) | hTopoII (% activity remaining at 100 μM) |
|---|---|---|---|---|---|
| 0006 | 8 | ND | ND | ND | ND |
| 0007 | 4 | ND | ND | ND | ND |
| 0009 | <=0.25, 0.5, 0.5 | 0.5 | ND | ND | ND |
| 0010 | 1, 2, 1 | 1 | ND | ND | ND |
| 0011 | 0.25, 0.5, 1, 1 | 0.5 | 0.1 | 13.8 | 84.18 |
| 0012 | <=0.25, 0.5, 1, 1, 1 | 0.5 | 0.28 | >100 | 93.22 |
| 0013 | 1, 2 | 2 | 0.36 | 50 | 95.12 |
| 0014 | 1, 1 | 2 | 0.33 | 25-50 | 93.81 |
| 0015 | <=0.25, 0.25 | 0.125 | 0.03 | 0.98 | 54.96 |
| 0016 | 0.125, <=0.25, 0.25 | 0.25, <=0.25, 0.25 | 0.09 | 7.98 | 77.43 |
| 0017 | 0.25 | 0.125 | ND | ND | ND |
| 0018 | <=0.25, 0.125 | 0.25 | 0.16 | 5.33 | 79.78 |
| 0019 | <=0.25, 0.25 | 0.5 | ND | ND | ND |
| 0020 | 0.5, 0.5 | 1 | 0.13 | 15.16 | 92.88 |
| 0021 | 0.5 | 0.5 | 0.59 | >100 | 91.14 |
| 0022 | 64 | ND | ND | ND | ND |
| 0023 | 8 | ND | 2.1 | >100 | 97.7 |
| 0024 | 64 | ND | ND | ND | ND |
| 0025 | >64 | ND | ND | ND | ND |
| 0026 | 64 | ND | ND | ND | ND |
| 0027 | >64 | ND | ND | ND | ND |
| 0028 | 64 | ND | ND | ND | ND |
| 0029 | 16 | ND | ND | ND | ND |
| 0030 | 2 | 1 | 0.95 | >100 | 97.82 |
| 0031 | 4 | | 1.53 | >100 | 98.74 |
| 0032 | >64 | ND | ND | ND | ND |
| 0033 | >64 | ND | ND | ND | ND |
| 0034 | 16 | ND | ND | ND | ND |
| 0035 | >64 | ND | ND | ND | ND |
| 0036 | >64 | ND | ND | ND | ND |
| 0037 | 32 | ND | ND | ND | ND |
| 0038 | >64 | ND | ND | ND | ND |
| 0039 | 64 | ND | ND | ND | ND |
| 0040 | >64 | ND | ND | ND | ND |
| 0041 | >64 | ND | ND | ND | ND |
| 0042 | 16 | ND | ND | ND | ND |
| 0043 | >64 | ND | ND | ND | ND |
| 0044 | 1 | 1 | ND | ND | ND |
| 0045 | 64 | ND | ND | ND | ND |
| 0046 | 0.5 | 1 | 0.6 | 100 | 88.33 |
| 0047 | >64 | ND | 13.3 | >100 | 88.38 |
| 0048 | 8 | ND | ND | ND | ND |
| 0049 | >64 | ND | ND | ND | ND |
| 0050 | 32 | ND | ND | ND | ND |
| 0051 | 1 | 1 | 0.42 | 50-100 | 93.73 |
| 0052 | 1 | 4 | 1.16 | >100 | 97.84 |
| 0055 | 0.5 | 1 | 0.78 | >100 | 99.06 |
| 0056 | 32 | ND | ND | ND | ND |
| 0057 | 1, 2 | 1 | 0.74 | >100 | 92.97 |
| 0058 | >64 | ND | ND | ND | ND |
| 0059 | <=0.5 | 0.25 | 0.17 | >100 | 95.72 |
| 0060 | 0.125 | 0.25 | 0.13 | 5.0-10 | 83.08 |
| 0061 | 0.125 | 0.25 | 0.42 | 61 | 69.61 |
| 0062 | 2 | 4 | 4.43 | >100 | 90.68 |
| 0069 | 8 | ND | ND | ND | ND |
| 0070 | 4 | ND | ND | ND | ND |
| 0071 | 1 | 2 | ND | ND | ND |
| 0075 | 16, 32 | ND | ND | ND | ND |
| 0076 | <=0.5, 0.125 | 1 | ND | ND | ND |
| 0077 | 1 | 2 | ND | ND | ND |
| 0078 | 4 | ND | ND | ND | ND |
| 0079 | 2 | 4 | ND | ND | ND |
| 0080 | 1 | 2 | ND | ND | ND |
| 0081 | 2 | 4 | ND | ND | ND |
| 0082 | 2 | 4 | ND | ND | ND |
| 0083 | 0.5 | 1 | ND | ND | ND |
| 0084 | 4 | ND | ND | ND | ND |
| 0085 | 2 | 4 | ND | ND | ND |
| 0088 | 8 | ND | ND | ND | ND |
| 0089 | <=0.5 | ND | ND | ND | ND |

ND = not determined;
multiple values provided when multiple MIC assays were conducted The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A Type II Topoisomerase inhibitor having Formula I:

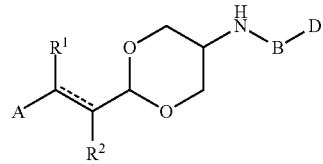

wherein
the dashed line represents a bond that is present or absent, and when the bond is present, $R^1$ and $R^2$ can be cis or trans;
A is a fused bicyclic aryl or bicyclic heteroaryl ring; having Formula II or III:

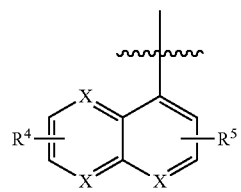

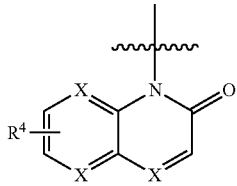

wherein each X is, independently, CH or N; or
A and $R^1$ together have Formula IX, X, XI, or XII

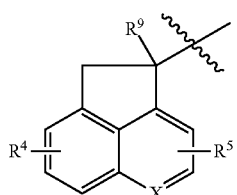

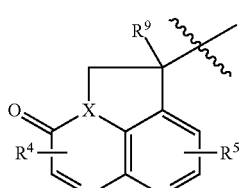

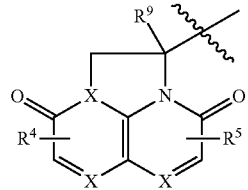

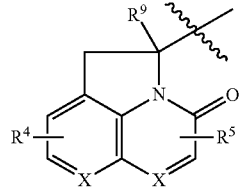

wherein each X is, independently, CH, N, or $CR^8$;
B is $C_1$-$C_6$ alkyl or $C_4$-$C_6$ cycloalkyl optionally substituted with one or more oxo, alkoxy, alkenyl, alkynyl, aryl, amino, carboxylic acid, halide, hydroxy, nitro or thiol;
D is a mono or bicyclic aryl or heteroaryl ring optionally substituted with alkyl, heteroalkyl, alkoxy, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;
$R^1$ and $R^2$ are, independently, chosen from H, OH, Cl, F, Br, I, CN, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, amino, carboxylic acid, halide, hydroxy, cyano, or nitro, silyl, sulfo-oxo, sulfonyl, sulfone, sulfoxide, or thiol, or $R^1$ is a $C_1$-$C_3$ alkyl or $C_2$-$C_3$ alkenyl, optionally substituted with $R^9$, also bound to A;
each $R^3$ is, independently, chosen from $C_1$-$C_6$ alkyl, $C_1$-$C_6$ cycloalkyl, aryl, heteroaryl, heterocycloalkyl, and heteroalkyl, any of which are optionally substituted with $C_1$-$C_6$ alkyl, $C_1$-$C_6$ alkoxyl, alkenyl, alkynyl, aryl, heteroaryl, aldehyde, amino, carboxylic acid, ester, ether, halide, hydroxy, ketone, cyano, nitro, silyl, sulfo-oxo, sulfonyl, sulfone, sulfoxide, or thiol;
each $R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, halide, hydroxy, ketone, cyano, nitro, or thiol;
each $R^8$ is Cl, F, CN, OH, $OCH_3$, $CH_3$, or $NH_2$; and
$R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with alkoxy, alkenyl, alkynyl, aryl, amino, carboxylic acid, halide, hydroxy, cyano, nitro, or thiol;
or a pharmaceutically acceptable salt thereof.

2. The inhibitor of claim 1, wherein $R^1$ and $R^2$ are, independently, chosen from H, F, CN, OH, and $NH_2$.

3. The inhibitor of claim 1, wherein $R^2$ is $NH_2$.

4. The inhibitor of claim 1, wherein $R^2$ is H or OH.

5. The inhibitor of claim 1, wherein A is the fused bicyclic aryl or bicyclic heteroaryl ring having Formula II:

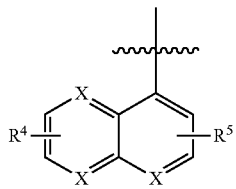

II

6. The inhibitor of claim 5, wherein $R^4$ and $R^5$ are, independently, chosen from H, Cl, F, Br, I, CN, OH, and unsubstituted $C_1$-$C_6$ alkyl or $C_1$-$C_6$ alkoxyl.

7. The inhibitor of claim 5, wherein $R^4$ and $R^5$ are, independently, chosen from H, Cl, F, OH, and methoxyl.

8. The inhibitor of claim 5, wherein $R^4$ and $R^5$ are, independently, chosen from F and methoxyl.

9. The inhibitor of claim 5, wherein two X's are N and the other X is CH.

10. The inhibitor of claim 5, wherein two X's are CH and the other X is N.

11. The inhibitor of claim 1, wherein A is the fused bicyclic aryl or bicyclic heteroaryl ring having Formula III:

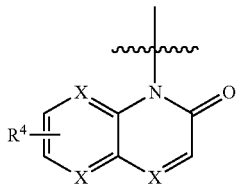

III

12. The inhibitor of claim 11, wherein $R^4$ is chosen from H, Cl, F, Br, I, OH, and unsubstituted $C_1$-$C_6$ alkyl or $C_1$-$C_6$ alkoxyl.

13. The inhibitor of claim 11, wherein $R^4$ is chosen from H, Cl, F, OH, and methoxyl.

14. The inhibitor of claim 11, wherein $R^4$ is chosen from F and methoxyl.

15. The inhibitor of claim 1, wherein A and $R^1$ together have Formula IX, X, XI, or XII

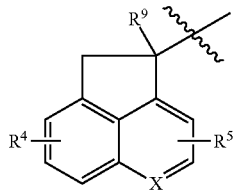

IX

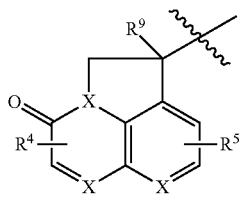

X

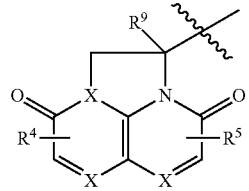

XI

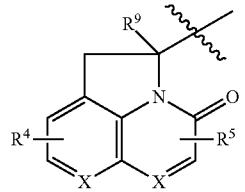

XII

16. The inhibitor of claim 15, wherein $R^4$ is H and $R^5$ is F.

17. The inhibitor of claim 1, wherein B is a $C_1$-$C_6$ alkyl, —C(═O)— or $C_4$-$C_6$ cycloalkyl.

18. The inhibitor of claim 1, wherein B is $CH_2$ or cyclobutyl.

19. The inhibitor of claim 1, wherein D is aryl or heteroaryl ring having Formula IV-VIII or XIII:

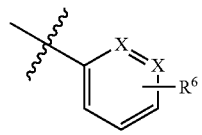

IV

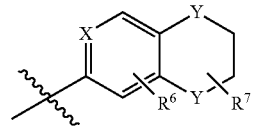

V

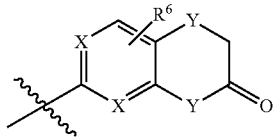

VI

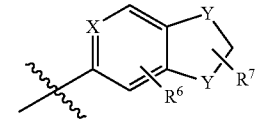

VII

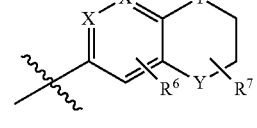

VIII

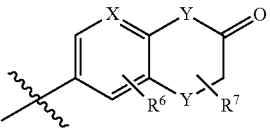

XIII wherein
each X is, independently, chosen from CH or N;
each Y is, independently, chosen from O, S, NH, or $CH_2$; and
$R^6$ and $R^7$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with alkoxy, alkenyl, alkynyl, aryl, amino, carboxylic acid, halide, hydroxy, cyano, nitro, or thiol.

20. The inhibitor of claim 19, wherein $R^6$ and $R^7$ are, independently, chosen from H, Cl, F, Br, I, CN, OH, and unsubstituted $C_1$-$C_6$ alkyl or $C_1$-$C_6$ alkoxyl.

21. The inhibitor of claim 19, wherein $R^6$ and $R^7$ are, independently, chosen from H, Cl, F, CN, OH, and methoxyl.

22. The inhibitor of claim 19, wherein $R^6$ and $R^7$ are both H.

23. The inhibitor of claim 19, wherein both Y are O.

24. The inhibitor of claim 19, wherein one Y is S and the other is O.

25. The inhibitor of claim 19, wherein one Y is NH and the other is O.

26. The inhibitor of claim 1, wherein the dashed line is a bond that is present.

27. The inhibitor of claim 1, wherein the dashed line is a bond that is absent.

28. The inhibitor of claim 1, wherein the stereochemistry of the dioxane is trans.

29. A method of treating an infection in a subject caused by resistant Gram-positive bacteria, comprising: administering a therapeutically effective amount of the inhibitor of claim 1 to the subject.

30. The method of claim 29, wherein the Gram-positive bacteria is Methicillin Resistant *S. aureus*.

31. A method of treating an infection in a subject caused by *Neisseria gonorrhoeae*, comprising: administering a therapeutically effective amount of the inhibitor of claim 1 to the subject.

32. The method of claim 29, wherein the infection is caused by *Enterococcus faecium*.

33. A method of treating an infection in a subject caused by *Mycobacterium*, comprising: administering a therapeutically effective amount of the inhibitor of claim 1 to the subject.

34. The inhibitor of claim 1, wherein $R^1$ is H or OH.

35. The inhibitor of claim 1, wherein the compound is selected from

AB-0141

AB-0143

AB-0147

AB-0288

AB-0158

-continued
AB-0214 (racemic)
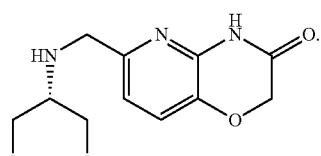
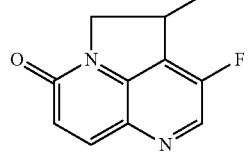
* * * * *

UNITED STATES PATENT AND TRADEMARK OFFICE
CERTIFICATE OF CORRECTION

PATENT NO. : 11,352,349 B2
APPLICATION NO. : 16/606044
DATED : June 7, 2022
INVENTOR(S) : Mark Mitton-Fry Page 1 of 1

It is certified that error appears in the above-identified patent and that said Letters Patent is hereby corrected as shown below:

On the Title Page

Column 2, item (57), Line 2 of the Abstract, delete second occurrence of "thereof" and insert -- thereof, --.

In the Claims

Claim 17, Column 102, Line 24, delete "—C(=O)—" and insert -- —C(=O)—, --.

Claim 36, Column 105, Lines 3-17, delete " 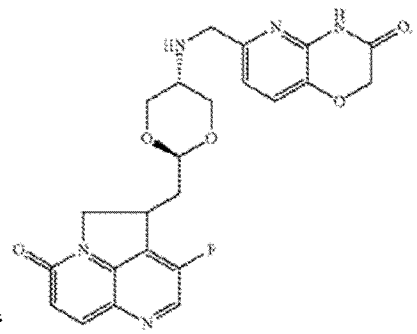 " and insert

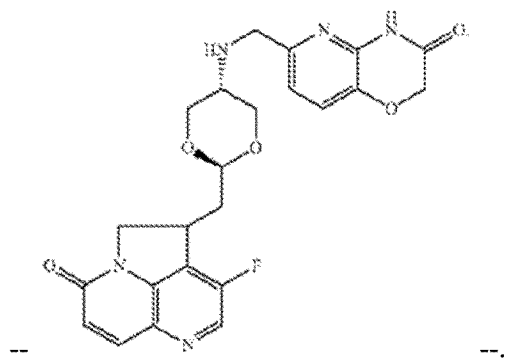

-- --.

Signed and Sealed this
Thirteenth Day of December, 2022

Katherine Kelly Vidal
*Director of the United States Patent and Trademark Office*